(12) United States Patent
Sharma et al.

(10) Patent No.: US 11,577,077 B2
(45) Date of Patent: *Feb. 14, 2023

(54) SYSTEMS AND METHODS FOR ELECTRICAL STIMULATION OF BIOLOGICAL SYSTEMS

(71) Applicant: EndoStim, Inc., Dallas, TX (US)

(72) Inventors: Virender K. Sharma, Paradise Valley, AZ (US); Shai Policker, Tenafly, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/528,997

(22) Filed: Aug. 1, 2019

(65) Prior Publication Data
US 2022/0072304 A1 Mar. 10, 2022

Related U.S. Application Data

(63) Continuation of application No. 15/639,590, filed on Jun. 30, 2017, now Pat. No. 10,406,356, which is a
(Continued)

(51) Int. Cl.
*A61N 1/36* (2006.01)
*A61B 5/03* (2006.01)
(Continued)

(52) U.S. Cl.
CPC ....... *A61N 1/36007* (2013.01); *A61N 1/3606* (2013.01); *A61N 1/36139* (2013.01);
(Continued)

(58) Field of Classification Search
CPC .... A61N 1/0517; A61N 1/36; A61N 1/36007; A61N 1/3606; A61N 1/36139;
(Continued)

(56) References Cited

U.S. PATENT DOCUMENTS

| | | | |
|---|---|---|---|
| 3,909,883 | A | 10/1975 | Fegen |
| 3,910,281 | A | 10/1975 | Kletschka |

(Continued)

FOREIGN PATENT DOCUMENTS

| | | |
|---|---|---|
| CN | 1476339 | 2/2004 |
| CN | 1494451 A | 5/2004 |

(Continued)

OTHER PUBLICATIONS

International Search Report for PCT/US2008/053780, dated Jun. 8, 2009.

(Continued)

*Primary Examiner* — Christopher A Flory
(74) *Attorney, Agent, or Firm* — Novel IP

(57) ABSTRACT

Systems and methods for the treatment of gastroesophageal reflux disease (GERD) include at least one electrically stimulating electrode coupled to a pulse generator. Individuals with GERD are treated by implanting a stimulation device within and/or proximate the patient's lower esophageal sphincter, gastric fundus, or other nearby gastrointestinal structures and applying electrical stimulation to the patient's lower esophageal sphincter and/or fundus, in accordance with certain predefined protocols. Electrical stimulation provided by the disclosed systems results in an increase in the length of the high pressure zone of the LES and/or modulation of the receptive relaxation response of the fundus to decrease gastric pressure, creating a longer barrier to the reflux of gastric contents or increasing functional lower esophageal pressure respectively, thereby treating GERD.

14 Claims, 29 Drawing Sheets

Related U.S. Application Data continuation of application No. 14/548,793, filed on Nov. 20, 2014, now Pat. No. 9,724,510, which is a continuation-in-part of application No. 14/500,856, filed on Sep. 29, 2014, now Pat. No. 9,561,367, which is a continuation of application No. 14/201,766, filed on Mar. 7, 2014, now Pat. No. 9,345,879, which is a continuation-in-part of application No. 14/175,927, filed on Feb. 7, 2014, now abandoned, and a continuation-in-part of application No. 13/934,040, filed on Jul. 2, 2013, now Pat. No. 8,798,753, said application No. 14/175,927 is a continuation-in-part of application No. 13/661,483, filed on Oct. 26, 2012, now abandoned, said application No. 14/201,766 is a continuation-in-part of application No. 13/041,063, filed on Mar. 4, 2011, now Pat. No. 8,712,529, and a continuation-in-part of application No. 13/041,114, filed on Mar. 4, 2011, now Pat. No. 8,712,530, said application No. 13/661,483 is a continuation of application No. 12/775,436, filed on May 9, 2010, now abandoned, said application No. 13/934,040 is a continuation of application No. 12/359,317, filed on Jan. 25, 2009, now Pat. No. 8,543,210, said application No. 12/775,436 is a continuation of application No. 11/539,645, filed on Oct. 9, 2006, now Pat. No. 7,738,961.

(60) Provisional application No. 61/906,812, filed on Nov. 20, 2013, provisional application No. 61/906,815, filed on Nov. 20, 2013, provisional application No. 61/448,849, filed on Feb. 21, 2011, provisional application No. 61/422,967, filed on Dec. 14, 2010, provisional application No. 61/414,378, filed on Nov. 16, 2010, provisional application No. 61/384,105, filed on Sep. 17, 2010, provisional application No. 61/371,146, filed on Aug. 5, 2010, provisional application No. 61/328,702, filed on Apr. 28, 2010, provisional application No. 61/318,843, filed on Mar. 30, 2010, provisional application No. 61/310,755, filed on Mar. 5, 2010, provisional application No. 61/023,535, filed on Jan. 25, 2008.

(51) Int. Cl.
*A61N 1/05* (2006.01)
*A61B 5/145* (2006.01)

(52) U.S. Cl.
CPC .............. *A61B 5/03* (2013.01); *A61B 5/14539* (2013.01); *A61N 1/0517* (2013.01); *A61N 1/3616* (2013.01); *A61N 1/36171* (2013.01); *A61N 1/36175* (2013.01)

(58) Field of Classification Search
CPC .............. A61N 1/3616; A61N 1/36171; A61N 1/36175; A61B 5/03; A61B 5/14539
See application file for complete search history.

(56) References Cited

U.S. PATENT DOCUMENTS

| | | | |
|---|---|---|---|
| 4,393,883 A | 7/1983 | Smyth | |
| 4,414,986 A | 11/1983 | Dickhudt | |
| 4,612,934 A | 9/1986 | Borkan | |
| 4,735,205 A | 4/1988 | Chachques | |
| 5,117,827 A | 6/1992 | Stuebe | |
| 5,188,104 A | 2/1993 | Wernicke | |
| 5,193,539 A | 3/1993 | Schulman | |
| 5,197,491 A | 3/1993 | Anderson | |
| 5,231,988 A | 8/1993 | Wernicke | |
| 5,263,480 A | 11/1993 | Wernicke | |
| 5,292,344 A | 3/1994 | Douglas | |
| 5,360,428 A | 11/1994 | Hutchinson, Jr. | |
| 5,423,872 A * | 6/1995 | Cigaina | A61N 1/36007 607/40 |
| 5,531,778 A | 7/1996 | Maschino | |
| 5,540,730 A | 7/1996 | Terry, Jr. | |
| 5,556,425 A | 9/1996 | Hewson | |
| 5,606,242 A | 2/1997 | Hull | |
| 5,633,573 A | 5/1997 | van Phuoc | |
| 5,649,902 A | 7/1997 | Yoon | |
| 5,674,205 A | 10/1997 | Pasricha | |
| 5,690,691 A | 11/1997 | Chen | |
| 5,697,375 A | 12/1997 | Hickey | |
| 5,709,224 A | 1/1998 | Behl | |
| 5,716,385 A * | 2/1998 | Mittal | A61N 1/36007 607/40 |
| 5,716,392 A | 2/1998 | Bourgeois | |
| 5,769,881 A | 6/1998 | Schroeppel | |
| 5,810,810 A | 9/1998 | Tay | |
| 5,836,994 A | 11/1998 | Bourgeois | |
| 5,861,014 A | 1/1999 | Familoni | |
| 5,861,044 A | 1/1999 | Crenshaw | |
| 5,882,340 A | 3/1999 | Yoon | |
| 5,893,883 A | 4/1999 | Torgerson | |
| 5,935,126 A | 8/1999 | Riza | |
| 5,995,872 A | 11/1999 | Bourgeois | |
| 6,006,755 A | 12/1999 | Edwards | |
| 6,026,326 A | 2/2000 | Bardy | |
| 6,041,258 A | 3/2000 | Cigaina | |
| 6,051,017 A | 4/2000 | Loeb | |
| 6,091,992 A | 7/2000 | Bourgeois | |
| 6,097,984 A * | 8/2000 | Douglas | A61N 1/36007 607/40 |
| 6,216,039 B1 | 4/2001 | Bourgeois | |
| 6,221,039 B1 | 4/2001 | Durgin | |
| 6,243,607 B1 | 6/2001 | Mintchev | |
| 6,254,598 B1 | 7/2001 | Edwards | |
| 6,285,897 B1 | 9/2001 | Kilcoyne | |
| 6,321,124 B1 | 11/2001 | Cigaina | |
| 6,360,130 B1 | 3/2002 | Duysens | |
| 6,381,495 B1 | 4/2002 | Jenkins | |
| 6,449,511 B1 | 9/2002 | Mintchev | |
| 6,510,332 B1 | 1/2003 | Greenstein | |
| 6,542,776 B1 | 4/2003 | Gordon | |
| 6,571,127 B1 | 5/2003 | Ben-Haim | |
| 6,587,719 B1 | 7/2003 | Barrett | |
| 6,591,137 B1 * | 7/2003 | Fischell | A61N 1/36007 607/40 |
| 6,606,523 B1 | 8/2003 | Jenkins | |
| 6,611,715 B1 | 8/2003 | Boveja | |
| 6,612,983 B1 | 9/2003 | Marchal | |
| 6,615,084 B1 * | 9/2003 | Cigaina | A61N 1/36007 607/116 |
| 6,678,561 B2 | 1/2004 | Forsell | |
| 6,684,104 B2 | 1/2004 | Gordon | |
| 6,735,477 B2 | 5/2004 | Levine | |
| 6,749,607 B2 | 6/2004 | Edwards | |
| 6,754,536 B2 | 6/2004 | Swoyer | |
| 6,760,626 B1 | 7/2004 | Boveja | |
| 6,820,019 B1 | 11/2004 | Kelly | |
| 6,826,428 B1 * | 11/2004 | Chen | A61N 1/36007 607/40 |
| 6,832,114 B1 | 12/2004 | Whitehurst | |
| 6,853,862 B1 | 2/2005 | Marchal | |
| 6,876,885 B2 | 4/2005 | Swoyer | |
| 6,879,859 B1 | 4/2005 | Boveja | |
| 6,879,861 B2 | 4/2005 | Benz | |
| 6,901,295 B2 * | 5/2005 | Sharma | A61N 1/36007 607/40 |
| 6,915,165 B2 | 7/2005 | Forsell | |
| 6,947,792 B2 | 9/2005 | Ben-Haim | |
| 6,952,613 B2 | 10/2005 | Swoyer | |
| 7,006,871 B1 | 2/2006 | Darvish | |
| 7,016,735 B2 | 3/2006 | Imran | |
| 7,054,689 B1 | 5/2006 | Whitehurst | |
| 7,054,690 B2 | 5/2006 | Imran | |
| 7,076,305 B2 | 7/2006 | Imran | |

(56) References Cited

U.S. PATENT DOCUMENTS

| | | |
|---|---|---|
| 7,076,306 B2 | 7/2006 | Marchal |
| 7,087,053 B2 | 8/2006 | Vanney |
| 7,114,502 B2 | 10/2006 | Schulman |
| 7,120,498 B2 * | 10/2006 | Imran .................. A61N 1/0517 607/40 |
| 7,127,295 B2 | 10/2006 | Evans |
| 7,146,216 B2 | 12/2006 | Bumm |
| 7,167,750 B2 * | 1/2007 | Knudson ................. A61N 1/05 607/40 |
| 7,177,693 B2 | 2/2007 | Starkebaum |
| 7,200,443 B2 | 4/2007 | Faul |
| 7,203,551 B2 | 4/2007 | Houben |
| 7,255,675 B2 | 8/2007 | Gertner |
| 7,263,405 B2 | 8/2007 | Boveja |
| 7,299,091 B2 | 11/2007 | Barrett |
| 7,310,557 B2 * | 12/2007 | Maschino ............. A61N 1/3686 607/40 |
| 7,340,306 B2 | 3/2008 | Barrett |
| 7,343,201 B2 | 3/2008 | Mintchev |
| 7,363,084 B2 | 4/2008 | Kurokawa |
| 7,444,183 B2 * | 10/2008 | Knudson ............. A61N 1/36071 607/40 |
| 7,477,994 B2 | 1/2009 | Sunshine |
| 7,499,752 B2 | 3/2009 | Maschino |
| 7,519,431 B2 | 4/2009 | Goetz |
| 7,519,433 B2 | 4/2009 | Foley |
| 7,558,629 B2 | 7/2009 | Keimel |
| 7,593,777 B2 | 9/2009 | Gerber |
| 7,599,736 B2 | 10/2009 | Dilorenzo |
| 7,620,454 B2 | 11/2009 | Dinsmoor |
| 7,664,551 B2 | 2/2010 | Cigaina |
| 7,676,270 B2 | 3/2010 | Imran |
| 7,702,394 B2 | 4/2010 | Imran |
| 7,702,395 B2 | 4/2010 | Towe |
| 7,702,934 B2 | 4/2010 | Lmran |
| 7,711,437 B1 | 5/2010 | Bornzin |
| 7,720,539 B2 | 5/2010 | Mintchev |
| 7,729,771 B2 * | 6/2010 | Knudson ............. A61N 1/36071 607/40 |
| 7,734,355 B2 * | 6/2010 | Cohen ................. A61N 1/36007 607/45 |
| 7,738,961 B2 * | 6/2010 | Sharma ............... A61N 1/36007 607/40 |
| 7,742,818 B2 * | 6/2010 | Dinsmoor ................ A61N 1/05 607/40 |
| 7,794,425 B2 | 9/2010 | Gobel |
| 7,809,442 B2 | 10/2010 | Bolea |
| 7,813,809 B2 | 10/2010 | Strother |
| 7,835,796 B2 | 11/2010 | Maschino |
| 7,848,802 B2 | 12/2010 | Goetz |
| 7,890,185 B2 | 2/2011 | Cohen |
| 7,899,540 B2 | 3/2011 | Maschino |
| 7,914,468 B2 | 3/2011 | Shalon |
| 7,941,221 B2 | 5/2011 | Foley |
| 7,957,807 B2 | 6/2011 | Starkebaum |
| 7,962,214 B2 | 6/2011 | Byerman |
| 7,983,755 B2 | 7/2011 | Starkebaum |
| 8,135,470 B2 | 3/2012 | Keimel |
| 8,155,758 B2 | 4/2012 | Roline |
| 8,160,709 B2 * | 4/2012 | Softer ................. A61N 1/36007 607/40 |
| 8,185,206 B2 | 5/2012 | Starkebaum |
| 8,282,561 B2 | 10/2012 | Towe |
| 8,380,321 B2 | 2/2013 | Goetz |
| 8,406,868 B2 | 3/2013 | Buschman |
| 8,423,134 B2 | 4/2013 | Buschman |
| 8,447,403 B2 | 5/2013 | Sharma |
| 8,447,404 B2 | 5/2013 | Sharma |
| 8,452,407 B2 | 5/2013 | Whitehurst |
| 8,467,874 B2 | 6/2013 | Chen |
| 8,467,884 B2 | 6/2013 | Chen |
| 8,521,292 B2 | 8/2013 | Wei |
| 8,538,532 B2 | 9/2013 | Starkebaum |
| 8,538,534 B2 | 9/2013 | Soffer |
| 8,543,210 B2 | 9/2013 | Sharma |
| 8,556,952 B2 * | 10/2013 | Shadduck ............. A61N 1/326 607/101 |
| 8,594,811 B2 | 11/2013 | Chen |
| 8,712,529 B2 | 4/2014 | Sharma |
| 8,712,530 B2 | 4/2014 | Sharma |
| 8,718,771 B2 | 5/2014 | Gandhi |
| 8,761,903 B2 | 6/2014 | Chen |
| 8,792,986 B2 | 7/2014 | Cigaina |
| 8,831,737 B2 | 9/2014 | Wesselink |
| 8,892,217 B2 | 11/2014 | Camps |
| 9,020,597 B2 * | 4/2015 | Sharma ................ A61N 1/0517 607/40 |
| 9,037,245 B2 | 5/2015 | Sharma |
| 9,061,147 B2 | 6/2015 | Sharma |
| 9,345,879 B2 | 5/2016 | Sharma |
| 9,498,619 B2 | 11/2016 | Goode |
| 9,724,510 B2 | 8/2017 | Sharma |
| 2001/0041831 A1 | 11/2001 | Starkweather |
| 2002/0103522 A1 | 8/2002 | Swoyer |
| 2002/0138075 A1 * | 9/2002 | Edwards ............. A61B 18/1233 606/41 |
| 2002/0161414 A1 * | 10/2002 | Flesler ..................... A61N 1/08 607/40 |
| 2002/0165589 A1 | 11/2002 | Imran |
| 2003/0009202 A1 | 1/2003 | Levine |
| 2003/0014086 A1 * | 1/2003 | Sharma ............... A61N 1/36007 607/40 |
| 2003/0028226 A1 | 2/2003 | Thompson |
| 2003/0055463 A1 | 3/2003 | Gordon |
| 2003/0078633 A1 | 4/2003 | Firlik |
| 2003/0120321 A1 | 6/2003 | Bumm |
| 2003/0144708 A1 | 7/2003 | Starkebaum |
| 2003/0195600 A1 | 10/2003 | Tronnes |
| 2004/0010290 A1 | 1/2004 | Schroeppel |
| 2004/0012088 A1 | 1/2004 | Fukasawa |
| 2004/0015201 A1 | 1/2004 | Greenstein |
| 2004/0024428 A1 | 2/2004 | Barrett |
| 2004/0039427 A1 | 2/2004 | Barrett |
| 2004/0044376 A1 * | 3/2004 | Flesler ............... A61N 1/36007 607/40 |
| 2004/0059393 A1 | 3/2004 | Policker |
| 2004/0073453 A1 | 4/2004 | Nenov |
| 2004/0088033 A1 | 5/2004 | Smits |
| 2004/0116977 A1 | 6/2004 | Finch |
| 2004/0138586 A1 | 7/2004 | Ganz |
| 2004/0147976 A1 | 7/2004 | Gordon |
| 2004/0167583 A1 | 8/2004 | Knudson |
| 2004/0172088 A1 | 9/2004 | Knudson |
| 2004/0186544 A1 | 9/2004 | King |
| 2004/0193229 A1 * | 9/2004 | Starkebaum ....... A61N 1/36007 607/40 |
| 2004/0215287 A1 | 10/2004 | Swoyer |
| 2004/0236381 A1 | 11/2004 | Dinsmoor |
| 2004/0236382 A1 | 11/2004 | Dinsmoor |
| 2004/0243182 A1 | 12/2004 | Cohen |
| 2005/0027328 A1 | 2/2005 | Greenstein |
| 2005/0049655 A1 | 3/2005 | Boveja |
| 2005/0065571 A1 * | 3/2005 | Imran .................. A61N 1/36007 607/41 |
| 2005/0070974 A1 | 3/2005 | Knudson |
| 2005/0075678 A1 | 4/2005 | Faul |
| 2005/0090873 A1 | 4/2005 | Imran |
| 2005/0131485 A1 | 6/2005 | Knudson |
| 2005/0131486 A1 | 6/2005 | Boveja |
| 2005/0137480 A1 | 6/2005 | Alt |
| 2005/0137643 A1 * | 6/2005 | Mintchev ........... A61N 1/36007 607/40 |
| 2005/0137644 A1 | 6/2005 | Boveja |
| 2005/0143787 A1 | 6/2005 | Boveja |
| 2005/0149141 A1 | 7/2005 | Starkebaum |
| 2005/0149142 A1 | 7/2005 | Starkebaum |
| 2005/0149146 A1 | 7/2005 | Boveja |
| 2005/0222637 A1 | 10/2005 | Chen |
| 2005/0222638 A1 | 10/2005 | Foley |
| 2005/0245788 A1 | 11/2005 | Gerber |
| 2005/0251219 A1 | 11/2005 | Evans |

(56) References Cited

U.S. PATENT DOCUMENTS

| | | | |
|---|---|---|---|
| 2006/0004304 A1* | 1/2006 | Parks | A61B 5/742 600/593 |
| 2006/0015162 A1 | 1/2006 | Edward | |
| 2006/0036293 A1 | 2/2006 | Whitehurst | |
| 2006/0041277 A1 | 2/2006 | Deem | |
| 2006/0047323 A1 | 3/2006 | Foley | |
| 2006/0064037 A1 | 3/2006 | Shalon | |
| 2006/0074459 A1* | 4/2006 | Flesler | A61N 1/306 607/40 |
| 2006/0089699 A1 | 4/2006 | Imran | |
| 2006/0095077 A1 | 5/2006 | Tronnes | |
| 2006/0106442 A1 | 5/2006 | Richardson | |
| 2006/0116736 A1 | 6/2006 | Dilorenzo | |
| 2006/0122660 A1 | 6/2006 | Boveja | |
| 2006/0149337 A1 | 7/2006 | John | |
| 2006/0167498 A1 | 7/2006 | Dilorenzo | |
| 2006/0200217 A1 | 9/2006 | Wessman | |
| 2006/0206160 A1 | 9/2006 | Cigaina | |
| 2006/0218011 A1 | 9/2006 | Walker | |
| 2006/0247717 A1 | 11/2006 | Starkebaum | |
| 2006/0247718 A1 | 11/2006 | Starkebaum | |
| 2006/0247719 A1 | 11/2006 | Maschino | |
| 2006/0247721 A1 | 11/2006 | Maschino | |
| 2006/0247722 A1* | 11/2006 | Maschino | A61N 1/36007 607/40 |
| 2006/0265021 A1 | 11/2006 | Herbert | |
| 2006/0270989 A1 | 11/2006 | McMichael | |
| 2007/0016274 A1* | 1/2007 | Boveja | A61N 1/06 607/101 |
| 2007/0049793 A1 | 3/2007 | Ignagni | |
| 2007/0060955 A1 | 3/2007 | Strother | |
| 2007/0060968 A1 | 3/2007 | Strother | |
| 2007/0060979 A1 | 3/2007 | Strother | |
| 2007/0066995 A1 | 3/2007 | Strother | |
| 2007/0067000 A1 | 3/2007 | Strother | |
| 2007/0100388 A1 | 5/2007 | Gerber | |
| 2007/0106337 A1* | 5/2007 | Errico | A61N 1/36085 607/40 |
| 2007/0106338 A1 | 5/2007 | Errico | |
| 2007/0114971 A1 | 5/2007 | Uesaka | |
| 2007/0142699 A1 | 6/2007 | Jandrall | |
| 2007/0142831 A1 | 6/2007 | Shadduck | |
| 2007/0142884 A1* | 6/2007 | Jandrall | A61B 18/1492 607/96 |
| 2007/0156182 A1 | 7/2007 | Castel | |
| 2007/0162084 A1 | 7/2007 | Chen | |
| 2007/0162085 A1 | 7/2007 | Dilorenzo | |
| 2007/0179542 A1 | 8/2007 | Prakash | |
| 2007/0185374 A1* | 8/2007 | Kick | A61B 17/00234 600/37 |
| 2007/0238942 A1 | 10/2007 | Baylor | |
| 2007/0239248 A1* | 10/2007 | Hastings | A61N 1/0573 607/126 |
| 2007/0244375 A1 | 10/2007 | Jenkins | |
| 2007/0255118 A1 | 11/2007 | Miesel | |
| 2007/0255335 A1 | 11/2007 | Herbert | |
| 2007/0255336 A1 | 11/2007 | Herbert | |
| 2007/0255352 A1 | 11/2007 | Roline | |
| 2007/0265662 A1 | 11/2007 | Ufford | |
| 2007/0265666 A1 | 11/2007 | Roberts | |
| 2007/0265668 A1 | 11/2007 | Reinke | |
| 2007/0265671 A1 | 11/2007 | Roberts | |
| 2007/0265674 A1 | 11/2007 | Olson | |
| 2007/0282410 A1 | 12/2007 | Cross | |
| 2007/0293910 A1 | 12/2007 | Strother | |
| 2007/0299481 A1 | 12/2007 | Syed | |
| 2008/0021512 A1 | 1/2008 | Knudson | |
| 2008/0039904 A1* | 2/2008 | Bulkes | A61N 1/37512 607/116 |
| 2008/0046062 A1 | 2/2008 | Camps | |
| 2008/0058836 A1 | 3/2008 | Moll | |
| 2008/0058891 A1 | 3/2008 | Ben-Haim | |
| 2008/0086179 A1* | 4/2008 | Sharma | A61N 1/36007 607/40 |
| 2008/0132968 A1 | 6/2008 | Starkebaum | |
| 2008/0147137 A1 | 6/2008 | Cohen | |
| 2008/0154191 A1 | 6/2008 | Gobel | |
| 2008/0183238 A1 | 7/2008 | Chen | |
| 2008/0195171 A1* | 8/2008 | Sharma | A61N 1/05 607/40 |
| 2008/0208355 A1 | 8/2008 | Stack | |
| 2009/0012421 A1 | 1/2009 | Bek | |
| 2009/0018617 A1 | 1/2009 | Skelton | |
| 2009/0018619 A1 | 1/2009 | Skelton | |
| 2009/0020406 A1 | 1/2009 | Nirmalakhandan | |
| 2009/0030475 A1 | 1/2009 | Brynelsen | |
| 2009/0069803 A1 | 3/2009 | Starkebaum | |
| 2009/0076498 A1 | 3/2009 | Saadat | |
| 2009/0088817 A1 | 4/2009 | Starkebaum | |
| 2009/0131993 A1 | 5/2009 | Rousso | |
| 2009/0132001 A1* | 5/2009 | Soffer | A61N 1/36007 607/40 |
| 2009/0187223 A1 | 7/2009 | Gross | |
| 2009/0192564 A1 | 7/2009 | Armstrong | |
| 2009/0204063 A1 | 8/2009 | Policker | |
| 2009/0210019 A1 | 8/2009 | Kim | |
| 2009/0264951 A1* | 10/2009 | Sharma | A61N 1/36007 607/40 |
| 2009/0281553 A1 | 11/2009 | Kalloo | |
| 2010/0004648 A1* | 1/2010 | Edwards | A61B 18/1477 606/41 |
| 2010/0010388 A1 | 1/2010 | Panken | |
| 2010/0049026 A1 | 2/2010 | Gerber | |
| 2010/0057085 A1 | 3/2010 | Holcomb | |
| 2010/0069789 A1 | 3/2010 | Hirota | |
| 2010/0076345 A1 | 3/2010 | Soffer | |
| 2010/0170812 A1 | 7/2010 | Odierno | |
| 2010/0198039 A1 | 8/2010 | Towe | |
| 2010/0228313 A1 | 9/2010 | Starkebaum | |
| 2010/0268495 A1 | 10/2010 | Armstrong | |
| 2010/0324432 A1 | 12/2010 | Bjoerling | |
| 2010/0324644 A1 | 12/2010 | Levi | |
| 2011/0004266 A1 | 1/2011 | Sharma | |
| 2011/0034967 A1 | 2/2011 | Chen | |
| 2011/0046653 A1 | 2/2011 | Addington | |
| 2011/0071589 A1 | 3/2011 | Starkebaum | |
| 2011/0213437 A9 | 9/2011 | Armstrong | |
| 2011/0224665 A1 | 9/2011 | Crosby | |
| 2011/0295335 A1 | 12/2011 | Sharma | |
| 2011/0295336 A1 | 12/2011 | Sharma | |
| 2011/0301662 A1 | 12/2011 | Bar-Yoseph | |
| 2011/0307023 A1 | 12/2011 | Tweden | |
| 2011/0307027 A1 | 12/2011 | Sharma | |
| 2011/0307028 A1 | 12/2011 | Sharma | |
| 2012/0232610 A1 | 9/2012 | Soffer | |
| 2012/0232615 A1 | 9/2012 | Barolat | |
| 2012/0259389 A1 | 10/2012 | Starkebaum | |
| 2012/0265103 A1 | 10/2012 | Policker | |
| 2012/0277619 A1 | 11/2012 | Starkebaum | |
| 2012/0296166 A1 | 11/2012 | Kim | |
| 2012/0310317 A1 | 12/2012 | Lund | |
| 2013/0030503 A1 | 1/2013 | Yaniv | |
| 2013/0035740 A1 | 2/2013 | Sharma | |
| 2013/0072928 A1* | 3/2013 | Schaer | A61B 8/4281 606/41 |
| 2013/0090551 A1 | 4/2013 | Sharma | |
| 2013/0178912 A1 | 7/2013 | Sharma | |
| 2013/0218229 A1 | 8/2013 | Sharma | |
| 2013/0231660 A1 | 9/2013 | Edwards | |
| 2013/0238048 A1 | 9/2013 | Almendinger | |
| 2014/0012348 A1 | 1/2014 | Starkebaum | |
| 2014/0018657 A1 | 1/2014 | Sharma | |
| 2014/0081366 A1 | 3/2014 | Bentley | |
| 2014/0088664 A1 | 3/2014 | Sharma | |
| 2014/0088666 A1 | 3/2014 | Goetz | |
| 2014/0107726 A1 | 4/2014 | Voznesensky | |
| 2014/0135886 A1* | 5/2014 | Cook | A61N 1/0456 607/136 |
| 2014/0194953 A1 | 7/2014 | Slavin | |
| 2014/0222106 A1 | 8/2014 | Sharma | |
| 2014/0228911 A1 | 8/2014 | Sharma | |
| 2014/0243593 A1 | 8/2014 | Goode | |
| 2014/0249594 A1 | 9/2014 | Sharma | |

(56) References Cited

U.S. PATENT DOCUMENTS

| | | | |
|---|---|---|---|
| 2014/0364678 A1 | 12/2014 | Harry | |
| 2015/0045786 A1* | 2/2015 | Edwards | A61B 18/1233 606/34 |
| 2015/0057718 A1 | 2/2015 | Sharma | |
| 2015/0119952 A1* | 4/2015 | Sharma | A61N 1/3606 607/40 |
| 2015/0224310 A1 | 8/2015 | Sharma | |
| 2015/0360037 A1 | 12/2015 | Hahn | |
| 2016/0001071 A1 | 1/2016 | Sharma | |
| 2016/0015392 A1 | 1/2016 | Gettman | |
| 2016/0045730 A1 | 2/2016 | Kim | |
| 2016/0059010 A1 | 3/2016 | Sharma | |
| 2017/0197028 A1 | 7/2017 | Goldsmith | |
| 2017/0224986 A1 | 8/2017 | Imran | |
| 2017/0348049 A1 | 12/2017 | Vrba | |
| 2018/0154135 A1 | 6/2018 | Goode | |

FOREIGN PATENT DOCUMENTS

| | | |
|---|---|---|
| CN | 102725021 | 10/2012 |
| CN | 105641805 | 6/2016 |
| CN | 105641805 A | 6/2016 |
| EP | 1004330 | 5/2000 |
| EP | 1004330 A1 | 5/2000 |
| WO | 199853878 | 12/1998 |
| WO | 9903532 | 1/1999 |
| WO | 9930776 | 6/1999 |
| WO | 0061223 A1 | 10/2000 |
| WO | 0061224 A1 | 10/2000 |
| WO | 2000061223 | 10/2000 |
| WO | 2000061224 | 10/2000 |
| WO | 0238217 A2 | 5/2002 |
| WO | 0243467 A2 | 6/2002 |
| WO | 2002043467 | 6/2002 |
| WO | 02089655 | 11/2002 |
| WO | 2002100481 A1 | 12/2002 |
| WO | 2005051486 A1 | 9/2005 |
| WO | 2007137026 | 11/2007 |
| WO | 2008117296 A1 | 10/2008 |
| WO | 2009009276 | 1/2009 |
| WO | 2009114008 A1 | 9/2009 |
| WO | 2010027963 | 3/2010 |
| WO | 2010135634 | 11/2010 |
| WO | 2012151449 | 11/2012 |
| WO | 2014032030 | 2/2014 |
| WO | 2015034867 | 3/2015 |
| WO | 2015077425 | 5/2015 |
| WO | 2015077435 | 5/2015 |

OTHER PUBLICATIONS

Summary of Neurostimulation Systems Features, Advanced Neuromodulation Systems (ANS) home page, accessed on May 31, 2007 at http://web.archive.org/web/20040211224857/www.ans-medical.com/patients/WhichSystemIsBest/SumOfNeurostimulation.html.

International Search Report for PCT/US2008/056479, dated Aug. 20, 2008.

International Search Report for PCT/US2011/027243, dated Jul. 8, 2011.

Christensen et al., 'Physiologic Specialization at Esophagogastric Junction in Three Species', American Journal of Physiology, vol. 225, No. 6, Dec. 1973, 1265-1270.

Cigaina, Valerio; Long-term Follow-Up of Gastric Stimulation for Obesity: The Mestre 8-Year Experience; Obesity Surgery; 14; 2004; S14-22.

Clarke et al,. 'An Endoscopic Implantable Device Stimulates the LES On-Demand By Remote Control in a Canine Model'; Gastrointestinal Endoscopy, vol. 63, No. 5; 2006, AB103, 759.

Clarke et al., 'An endoscopically implantable device stimulates the lower esophageal sphincter on demand by remote control: a study using a canine model', Endoscopy 2007; 39: 72-76.

Ellis, et al., 'The Prevention of Experimentally Induced Reflux by Electrical Stimulation of the Distal Esophagus', American Journal of Surgery, vol. 115, Apr. 1968, 482-487.

Gonzalez et al., 'Different Responsiveness of Excitatory and Inhibitory Enteric Motor Neurons in the Human Esophagus to Electrical Field Stimulation and to Nicotine', Am J Physiol Gastrointest Liver Physiol, 287:G299-G306, 2004.

International Search Report for PCT/US12/053576, dated Dec. 24, 2012.

International Search Report for PCT/US2007/068907, dated Aug. 7, 2008.

International Search Report for PCT/US2012/033695, dated Aug. 7, 2012.

International Search Report for PCT/US2012/036408, dated Aug. 17, 2012.

International Search Report for PCT/US2013/056520, dated Apr. 4, 2014.

International Search Report for PCT/US2014/053793, dated Mar. 27, 2015.

International Search Report for PCT/US2014/066565, dated Mar. 12, 2015.

International Search Report for PCT/US2014/066578, dated Mar. 19, 2015.

Jameison, GG et al. "Laparoscopic Nissen Fundoplication". Annals of Surgery, vol. 220. No. 2, p. 139 (1994).

Kahrilas et al., 'Impact of Fundoplication on Bolus Transit Across Esophagogastric Junction', American Physiological Society, 1998, 1386-1393.

Kamath et al., 'Neurocardiac and Cerebral Responses Evoked By Esophageal Vago-Afferent Stimulation in Humans: Effects of Varying Intensities', Cardiovascular Research, 40 (1998) 591-599.

Kantsevoy et al., 'An Endoscopically Implantable On-Demand Stimulator Is Successful in Increasing Lower Esophageal Sphincter Pressure in a Porcine Model'; Gastrointestinal Endoscopy, vol. 61, No. 5: 2005, AB79, 222.

Lund et al., 'Electrical Stimulation of Esophageal Smooth Muscle and Effects of Antagonists', American Journal of Physiology, vol. 217, No. 5, Nov. 1969, 1369-1374.

Sallam et al., 'Feasibility of gastric electrical stimulation by percutaneous endoscopic transgastric electrodes'; Gastrointestinal Endoscopy; vol. 68, No. 4; 2008, 754-759.

Sanmiguel et al., 'Effect of electrical stimulation of the LES on LES pressure in a canine model'; Am J Physiol Gastrointest Live Physiol; 295: 389-394; 2008.

Shellock, Frank G. 'RF Bion Microstimulator' MRISafety.com, http://www.mrisafety.com/SafetyInfov.asp?SafetyInfoID=254, Shellock R & D Services, Inc. and Frank G. Shellock, Ph.D., 4 pages, 2014.

Stein et al., 'Three-dimensional Imaging of the Lower Esophageal Sphincter in Gastroesophageal Reflux Disease,' Annual Meeting of the American Surgical Association, Apr. 11-13, 1991, 374-383.

Tam, WCE et al. "Delivery of radiofrequency energy to the lower esophageal sphincter and gastric cardia inhibits transient oesophageal sphincter relaxations and gastro-oesophageal reflux in patients with reflux disease". Gut, 52(4), 479-785 (2003).

Xing et al., 'Gastric Electrical Stimulation (GES) with Parameters for Morbid Obesity Elevates Lower Esophageal Sphincter (LES) Pressure in Conscious Dogs'; Obesity Surgery; 15; 2005; pp. 1321-1327.

Xing et al., 'Gastric Electrical Stimulation Significantly Increases Canine Lower Esophageal Sphincter Pressure'; Digestive Diseases and Sciences; vol. 50, No. 8 (Aug. 2005), pp. 1481-1487.

Xing et al., 'Gastric Electrical Stimulation Significantly Increases Canine Lower Esophageal Pressure' Gastroenterology 122: May Issue, A579, 2003. Presented as a poster at Digestive Disease Week in Orlando, FL on Monday, May 19, 2003.

International Search Report for PCT/US2015/061108, dated May 26, 2016.

International Search Report for PCT/US2018/025092, dated Jun. 27, 2018.

International Search Report for PCT/US2017/062298, dated Feb. 1, 2018.

(56) References Cited

OTHER PUBLICATIONS

International Search Report for PCT/US2019/016923, dated Jun. 7, 2019.

\* cited by examiner

- Lead Placement Combinations
  - AB
  - AB or CD
  - AC / BD Alternating
  - AB / CD Alternating
  - AB Vs. CD

SYSTEMS AND METHODS FOR ELECTRICAL STIMULATION OF BIOLOGICAL SYSTEMS

CROSS-REFERENCE

The present application is a continuation application of U.S. patent application Ser. No. 15/639,590, entitled "Systems and Methods for Electrical Stimulation of Biological Systems" and filed on Jun. 30, 2017, which is a continuation application of U.S. patent application Ser. No. 14/548,793, of the same title, filed on Nov. 20, 2014, and issued as U.S. Pat. No. 9,724,510 on Aug. 8, 2017, which relies on U.S. Provisional Patent Application No. 61/906,812, entitled "Systems and Methods for Increasing the Length of the Lower Esophageal Sphincter High Pressure Zone" and filed on Nov. 20, 2013 and U.S. Provisional Patent Application No. 61/906,815, entitled "Systems and Methods for Modulating the Receptive Relaxation of the Fundus" and filed on Nov. 20, 2013, for priority.

U.S. patent application Ser. No. 14/548,793 is also a continuation-in-part application of U.S. patent application Ser. No. 14/500,856, entitled "Device and Implantation System for Electrical Stimulation of Biological Systems" filed on Sep. 29, 2014, and issued as U.S. Pat. No. 9,561,367 on Feb. 7, 2017, which is a continuation application of U.S. patent application Ser. No. 14/201,766, ("'766 application") of the same title, filed on Mar. 7, 2014, and issued as U.S. Pat. No. 9,345,879 on May 24, 2016, which is a continuation-in-part application of U.S. patent application Ser. No. 14/175,927, of the same title and filed on Feb. 7, 2014, which is a continuation-in-part application of U.S. patent application Ser. No. 13/661,483, entitled "Methods and Systems for Treating the Gastrointestinal Tract" and filed on Oct. 26, 2012, which is a continuation of U.S. patent application Ser. No. 12/775,436, entitled "Method and Apparatus for Treatment of the Gastrointestinal Tract" and filed on May 6, 2010, which is a continuation application of U.S. patent application Ser. No. 11/539,645, of the same title, filed on Oct. 9, 2006, and issued as U.S. Pat. No. 7,738,961 on Jun. 15, 2010.

The '766 application is also a continuation-in-part application of U.S. patent application Ser. No. 13/041,063, entitled "Device and Implantation System for Electrical Stimulation of Biological Systems", filed on Mar. 4, 2011, and issued as U.S. Pat. No. 8,712,529 on Apr. 29, 2014, which relies on U.S. Provisional Patent Application No. 61/444,849, of the same title and filed on Feb. 21, 2011; 61/422,967, entitled "Methods and Systems for Improving the Operation of An Active Implantable Medical Device" and filed on Dec. 14, 2010; 61/414,378, entitled "Method and System for Implanting a Medical Device Into A Human Body and Electrically Stimulating Human Tissue", filed on Nov. 16, 2010; 61/384,105, entitled "Device and Implantation System for Electrical Stimulation of Biological Tissues" and filed on Sep. 17, 2010; 61/371,146, of the same title and filed on Aug. 5, 2010; 61/328,702, of the same title and filed on Apr. 28, 2010; 61/318,843, of the same title and filed on Mar. 30, 2010; and 61/310,755, of the same title and filed on Mar. 5, 2010, for priority.

The '766 application is also a continuation-in-part application of U.S. patent application Ser. No. 13/041,114, entitled "Device and Implantation System for Electrical Stimulation of Biological Systems", filed on Mar. 4, 2011, and issued as U.S. Pat. No. 8,712,530 on Apr. 29, 2014.

The '766 application is also a continuation-in-part application of U.S. patent application Ser. No. 13/934,040, entitled "Device and Implantation System for Electrical Stimulation of Biological Systems", filed on Jul. 2, 2013, and issued as U.S. Pat. No. 8,798,753 on Aug. 5, 2014, which is a continuation application of U.S. patent application Ser. No. 12/359,317, of the same title, filed on Jan. 25, 2009, and issued as U.S. Pat. No. 8,543,210 on Sep. 24, 2013, which relies on U.S. Provisional Patent Application No. 61/023,535, entitled "Device for Electrical Stimulation of Biological Systems" and filed on Jan. 25, 2008, for priority.

The '766 application is also related to U.S. patent application Ser. No. 13/041,098, entitled "Device and Implantation System for Electrical Stimulation of Biological Systems", filed on Mar. 4, 2011, and now issued as U.S. Pat. No. 8,447,403.

The '766 specification is also related to U.S. patent application Ser. No. 13/041,116, entitled "Device and Implantation System for Electrical Stimulation of Biological Systems", filed on Mar. 4, 2011, and now issued as U.S. Pat. No. 8,447,404.

Each of the above applications is hereby incorporated by reference in its entirety.

FIELD

The present specification relates generally to electrical stimulation of anatomical structures to treat biological conditions. More particularly, the present specification relates to electrical stimulation of the esophagus and/or stomach to increase the length of the lower esophageal sphincter (LES) high pressure zone and/or increase the receptive relaxation response of the fundus of the stomach for the treatment of gastroesophageal reflux disease (GERD).

BACKGROUND

Electrical stimulation of nerves and surrounding tissue is used to treat a variety of conditions. For example, electrical stimulation can be used to restore partial function to limbs or organs following traumatic injury. Electrical stimulation can also be used to reduce pain. Specifically, electrical stimulation can be used to treat disorders associated with the gastrointestinal (GI) system, such as, obesity and gastroesophageal reflux disease (GERD).

Gastro-esophageal reflux disease (GERD) is a common health problem and is expensive to manage in both primary and secondary care settings. This condition results from exposure of esophageal mucosa to gastric acid and bile as the gastro-duodenal content refluxes from the stomach into the esophagus. The acid and bile damages the esophageal mucosa resulting in heartburn, ulcers, bleeding, and scarring, and long term complications such as Barrett's esophagus (pre-cancerous esophageal lining) and adeno-cancer of the esophagus. Patients with GERD may only experience symptoms during the day, referred to as diurnal GERD, and may not experience any GERD symptoms at night, referred to as nocturnal GERD. Diurnal or daytime or upright GERD has been associated with tLESR, and may be diagnosed where a patient has symptoms of heartburn, regurgitation or both.

The severity of GERD increases progressively from postprandial to upright, to supine, to bipositional reflux. A structural defect as reflected by decreased LES pressure and length is also significantly less common with postprandial and upright reflux. The improved esophageal sensation associated with improved saliva production that neutralizes the refluxed acid and increased clearance of the refluxate aided by gravity results in lesser esophageal damage.

Lifestyle advice and antacid therapy are advocated as first line treatments for the disease. However, since most patients with moderate to severe cases of GERD do not respond adequately to these first-line measures and need further treatment, other alternatives, including pharmacological, endoscopic, and surgical treatments are employed.

The most commonly employed pharmacological treatment is daily use of H2 receptor antagonists (H2RAs) or proton-pump inhibitors (PPIs) for acid suppression. Since gastro-esophageal reflux disease usually relapses once drug therapy is discontinued, most patients with the disease, therefore, need long-term drug therapy. However, daily use of PPIs or H2RAs is not universally effective in the relief of GERD symptoms or as maintenance therapy. Additionally, not all patients are comfortable with the concept of having to take daily or intermittent medication for the rest of their lives and many are interested in nonpharmacological options for managing their reflux disease.

Several endoscopic procedures for the treatment of GERD have been tried. These procedures can be divided into three approaches: endoscopic suturing, wherein stitches are inserted in the gastric cardia to plicate and strengthen the lower esophageal sphincter; endoscopic application of energy to the lower esophagus; and, injection of bulking agents into the muscle layer of the distal esophagus. These procedures, however, are not without their risks, besides being technically demanding and involving a long procedure time. As a result, these procedures have largely been discontinued.

Open surgical or laparoscopic fundoplication is also used to correct the cause of the disease. However, surgical procedures are associated with significant morbidity and small but not insignificant mortality rates. Moreover, long-term follow-up with patients treated by surgery suggests that many patients continue to need acid suppressive medication. There is also no convincing evidence that fundoplication reduces the risk of esophageal adenocarcinoma in the long term.

Electrical stimulation is one methodology aimed at treating GERD. Electrical stimulation employs an implantable, pacemaker-like device to deliver low-level electrical stimulation to portions of the esophagus and/or stomach. For example, in U.S. Pat. No. 6,901,295, assigned to the applicant of the current invention, "A method and apparatus for electrical stimulation of the lower esophageal sphincter (LES) is provided. Electrode sets are placed in the esophagus in an arrangement that induce contractions of the LES by electrical stimulation of the surrounding tissue and nerves. The electrical stimulus is applied by a pulse generator for periods of varying duration and varying frequency so as to produce the desired contractions. The treatment may be short-term or may continue throughout the life of the patient in order to achieve the desired therapeutic effect. The stimulating electrode sets can be used either alone or in conjunction with electrodes that sense esophageal peristalsis. The electrode sets can be placed endoscopically, surgically or radiologically." The referenced invention relies on sensing certain physiological changes in the esophagus, such as changes in esophageal pH, to detect acid reflux. Once a change in esophageal pH is recognized, the system generates an electrical stimulation in an attempt to instantaneously close the LES and abort the episode of acid reflux. U.S. Pat. No. 6,901,295 is hereby incorporated by reference in its entirety.

While current electrical stimulation systems are effective in treating GERD, they do not address all of the anatomical factors involved in the cause of the disease. Particularly, patients suffering from GERD often exhibit a shortened LES high pressure zone. The LES high pressure zone is a segment of the LES in which the pressure is higher than the pressure in the immediately proximal and distal portions of the esophagus. The higher pressure in this zone helps to keep stomach contents from refluxing. A shortened zone presents less resistance to refluxing gastric acid. Lengthening the LES high pressure zone would create a longer barrier to refluxing stomach contents. Therefore, what is needed is an electrical stimulation system which acts to increase the length of the LES high pressure zone, thereby reducing the frequency and severity of GERD.

SUMMARY

The present specification discloses a system for increasing the length of a high pressure zone of a lower esophageal sphincter (LES) of a patient, said system comprising: at least one electrically stimulating electrode positioned proximate said LES; a waveform generator coupled to said at least one electrode; and, a controller configured to electrically stimulate an area proximate said LES to increase the length of said high pressure zone above a threshold level which reduces at least one of a frequency of occurrence or an intensity of gastroesophageal reflux symptoms in said patient.

In one embodiment, the at least one electrode is positioned within said LES. In another embodiment, the at least one electrode is positioned within a gastric cardia of said patient. In another embodiment, the at least one electrode is positioned in an area within 3 cm of said LES.

In one embodiment, the system comprises at least two electrodes wherein at least one first electrode is positioned within said LES and at least one second electrode is positioned within a gastric cardia of said patient. In another embodiment, the system comprises at least two electrodes wherein at least one first electrode is positioned within said LES and at least one second electrode is positioned in an area within 3 cm of said LES. In another embodiment, the system comprises at least two electrodes wherein at least one first electrode is positioned within a gastric cardia of said patient and at least one second electrode is positioned in an area within 3 cm of said LES.

In one embodiment, the system comprises at least three electrodes wherein at least one first electrode is positioned within said LES, at least one second electrode is positioned within a gastric cardia of said patient, and at least one third electrode is positioned in an area within 3 cm of said LES.

In one embodiment, the high pressure zone has a baseline length, defined as the length of the high pressure zone prior to stimulation, and the threshold level defines a length of the high pressure zone which is at least 10% greater than said baseline length.

In various embodiments, the controller causes the waveform generator to generate a pulse stream defined by a plurality of parameters comprising: a pulse width having a range of 30 μsec to 5 msec; a pulse amplitude having a range of 2 to 15 mAmp; an on period ranging from 1 second to 23 hours, 59 minutes, and 59 seconds; an off period ranging from 1 second to 23 hours, 59 minutes, and 59 seconds; a duty cycle ranging from 1 to 100%; and, a pulse frequency. In various embodiments, the pulse frequency has a range of 1-100 Hz or 1-59 cpm.

The present specification also discloses a system for increasing the length of a high pressure zone of a lower esophageal sphincter (LES) of a patient, said system comprising: at least one electrically stimulating electrode positioned proximate said LES; a waveform generator coupled to said at least one electrode; a controller configured to electrically stimulate an area proximate said LES to increase the length of said high pressure zone above a threshold level which reduces at least one of a frequency of occurrence or an intensity of gastroesophageal reflux symptoms in said patient; wherein an average pressure within said high pressure zone is greater than 5 mm Hg and wherein said high pressure zone has a baseline length prior to stimulation and said threshold level defines a length of said high pressure zone which is at least 10% greater than said baseline length.

In one embodiment, the said at least one electrode is positioned within said LES. In another embodiment, the at least one electrode is positioned within a gastric cardia of said patient or within 3 cm of said LES.

In one embodiment, the system further comprises at least one sensor for sensing at least one physiological parameter of said patient.

In one embodiment, the said at least one sensor is configured to measure any one or combination of LES high pressure zone length, LES pressure, esophageal pH, inclinometer data, temperature, or accelerometer data.

In one embodiment, the controller is configured to electrically stimulate said area proximate said LES based on data sensed by said at least one sensor.

In various embodiments, the controller causes the waveform generator to generate a pulse stream defined by a plurality of parameters comprising: a pulse width having a range of 30 μsec to 5 msec; a pulse amplitude having a range of 2 to 15 mAmp; an on period ranging from 1 second to 23 hours, 59 minutes, and 59 seconds; an off period ranging from 1 second to 23 hours, 59 minutes, and 59 seconds; a duty cycle ranging from 1 to 100%; and, a pulse frequency. In various embodiments, the pulse frequency has a range of 1-100 Hz or 1-59 cpm.

The present specification also discloses a method for increasing the length of a high pressure zone of a lower esophageal sphincter (LES) of a patient, said method comprising the steps of: providing an electrical stimulation system, said system comprising: at least one electrically stimulating electrode; a waveform generator coupled to said at least one electrode; and, a controller configured to operate said waveform generator to transmit an electrical current to said at least one electrode; implanting said at least one electrode within 3 cm of said LES or within a gastric cardia of said patient; and, operating said controller to cause said at least one electrode to electrically stimulate an area proximate said LES to increase the length of said high pressure zone above a threshold level which reduces at least one of a frequency of occurrence or an intensity of gastroesophageal reflux symptoms in said patient.

In one embodiment, referring to the method described above, the at least one electrode is positioned within said LES.

In one embodiment, referring to the method described above, an average pressure within said high pressure zone is greater than 5 mm Hg.

In one embodiment, referring to the method described above, the high pressure zone has a baseline length prior to stimulation and said threshold level defines a length of said high pressure zone which is at least 10% greater than said baseline length.

In one embodiment, referring to the method described above, the electrical stimulation system further comprises at least one sensor and the method further comprises the steps of: sensing at least one physiological parameter of said patient via said at least one sensor; and, modifying the operation of said controller to cause said at least one electrode to electrically stimulate an area proximate said LES based upon said at least one sensed physiological parameter.

In various embodiments, referring to the method described above, the controller causes the waveform generator to generate a pulse stream defined by a plurality of parameters comprising: a pulse width having a range of 30 μsec to 5 msec; a pulse amplitude having a range of 2 to 15 mAmp; an on period ranging from 1 second to 23 hours, 59 minutes, and 59 seconds; an off period ranging from 1 second to 23 hours, 59 minutes, and 59 seconds; a duty cycle ranging from 1 to 100%; and, a pulse frequency. In various embodiments, the pulse frequency has a range of 1-100 Hz or 1-59 cpm.

The present specification also discloses a system for modulating muscle tone of a gastric fundus and decreasing gastric pressure of a patient. There exists an effective, or functional, LES pressure which is a gradient between the actual LES pressure and the gastric pressure. Current electrical stimulation systems treat GERD by causing an increase in the actual LES pressure and therefore an increase in the functional LES pressure. However, functional LES pressure can also be increased by decreasing the gastric pressure. A normal human stomach includes a receptive relaxation response in the fundus, or upper portion, in response to food intake. The stomach is under neural control to maintain a constant pressure as a person eats. The muscles of the stomach relax during food accumulation so that the stomach can expand and pressure can remain constant. As such, the mechanical changes that occur in the walls of the fundus during this relaxation response can be considered a parameter in controlling post-prandial reflux. Therefore, what is needed is an electrical stimulation system to treat GERD which functions by providing stimulation in and/or proximate the fundus, thereby enhancing the normal receptive relaxation response and decreasing gastric pressure. The decreased gastric pressure results in an increased functional LES pressure and reduces the likelihood of a reflux event.

Accordingly, the present application discloses a system for modulating muscle tone of a gastric fundus and decreasing gastric pressure of a patient that comprises at least one electrically stimulating electrode positioned proximate said gastric fundus; a waveform generator coupled to said at least one electrode; and, a controller configured to electrically stimulate an area proximate said gastric fundus to decrease said gastric pressure below a threshold level which reduces at least one of a frequency of occurrence or an intensity of gastroesophageal reflux symptoms in said patient.

In one embodiment, the at least one electrode is positioned within said gastric fundus. In another embodiment, the at least one electrode is positioned within a lower esophageal sphincter (LES) of said patient. In another embodiment, the at least one electrode is positioned in an area within 3 cm of a lower esophageal sphincter (LES) of said patient.

In one embodiment, the system comprises at least two electrodes wherein at least one first electrode is positioned within said gastric fundus and at least one second electrode is positioned within a lower esophageal sphincter (LES) of said patient. In another embodiment, the system comprises at least two electrodes wherein at least one first electrode is positioned within said gastric fundus and at least one second electrode is positioned in an area within 3 cm of a lower esophageal sphincter (LES) of said patient. In another embodiment, the system comprises at least two electrodes wherein at least one first electrode is positioned within a lower esophageal sphincter (LES) of said patient and at least one second electrode is positioned in an area within 3 cm of said LES.

In one embodiment, the system comprises at least three electrodes wherein at least one first electrode is positioned within said gastric fundus, at least one second electrode is positioned within a lower esophageal sphincter (LES) of said patient, and at least one third electrode is positioned in an area within 3 cm of said LES.

In one embodiment, gastric pressure is equal to a baseline pressure prior to stimulation and said threshold level defines a gastric pressure which is at least 10% less than said baseline pressure.

In various embodiments, the controller causes the waveform generator to generate a pulse stream defined by a plurality of parameters comprising: a pulse width having a range of 30 μsec to 5 msec; a pulse amplitude having a range of 2 to 15 mAmp; an on period ranging from 1 second to 23 hours, 59 minutes, and 59 seconds; an off period ranging from 1 second to 23 hours, 59 minutes, and 59 seconds; a duty cycle ranging from 1 to 100%; and, a pulse frequency. In various embodiments, the pulse frequency has a range of 1-100 Hz or 1-59 cpm.

The present specification also discloses a system for modulating muscle tone of a gastric fundus and decreasing gastric pressure of a patient, said system comprising: at least one electrically stimulating electrode positioned proximate said gastric fundus; a waveform generator coupled to said at least one electrode; a controller configured to electrically stimulate an area proximate said gastric fundus to decrease said gastric pressure below a threshold level which reduces at least one of a frequency of occurrence or an intensity of gastroesophageal reflux symptoms in said patient; wherein said gastric pressure includes a baseline pressure prior to stimulation which is equal to approximately 10 mm Hg and said threshold level defines a gastric pressure which is at least 10% less than said baseline pressure.

In one embodiment, the at least one electrode is positioned within said gastric fundus. In another embodiment, the at least one electrode is positioned within a lower esophageal sphincter (LES) of said patient or within 3 cm of said LES.

In one embodiment, the system further comprises at least one sensor for sensing at least one physiological parameter of said patient.

In one embodiment, the at least one sensor is configured to measure any one or combination of gastric pressure, LES pressure, esophageal pH, inclinometer data, temperature, or accelerometer data.

In one embodiment, the controller is configured to electrically stimulate said area proximate said gastric fundus based on data sensed by said at least one sensor.

In various embodiments, the controller causes the waveform generator to generate a pulse stream defined by a plurality of parameters comprising: a pulse width having a range of 30 μsec to 5 msec; a pulse amplitude having a range of 2 to 15 mAmp; an on period ranging from 1 second to 23 hours, 59 minutes, and 59 seconds; an off period ranging from 1 second to 23 hours, 59 minutes, and 59 seconds; a duty cycle ranging from 1 to 100%; and, a pulse frequency. In various embodiments, the pulse frequency has a range of 1-100 Hz or 1-59 cpm.

The present specification also discloses a method for modulating muscle tone of a gastric fundus and decreasing gastric pressure of a patient, said method comprising the steps of: providing an electrical stimulation system, said system comprising: at least one electrically stimulating electrode; a waveform generator coupled to said at least one electrode; and, a controller configured to operate said waveform generator to transmit an electrical current to said at least one electrode; implanting said at least one electrode in a gastric fundus or within 3 cm of a lower esophageal sphincter (LES) of said patient; and, operating said controller to cause said at least one electrode to electrically stimulate an area proximate said gastric fundus to decrease said gastric pressure below a threshold level which reduces at least one of a frequency of occurrence or an intensity of gastroesophageal reflux symptoms in said patient.

In one embodiment, referring to the method described above, an average gastric pressure prior to stimulation is equal to approximately 10 mm Hg.

In one embodiment, referring to the method described above, the at least one electrode is positioned within said LES.

In one embodiment, referring to the method described above, gastric pressure is equal to a baseline pressure prior to stimulation and said threshold level defines a gastric pressure which is at least 10% less than said baseline pressure.

In one embodiment, referring to the method described above, the electrical stimulation system further comprises at least one sensor and the method further comprises the steps of: sensing at least one physiological parameter of said patient via said at least one sensor; and, modifying the operation of said controller to cause said at least one electrode to electrically stimulate an area proximate said gastric fundus based upon said at least one sensed physiological parameter.

In various embodiments, referring to the method described above, the controller causes the waveform generator to generate a pulse stream defined by a plurality of parameters comprising: a pulse width having a range of 30 μsec to 5 msec; a pulse amplitude having a range of 2 to 15 mAmp; an on period ranging from 1 second to 23 hours, 59 minutes, and 59 seconds; an off period ranging from 1 second to 23 hours, 59 minutes, and 59 seconds; a duty cycle ranging from 1 to 100%; and, a pulse frequency. In various embodiments, the pulse frequency has a range of 1-100 Hz or 1-59 cpm.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings.

DETAILED DESCRIPTION

Figure 1:
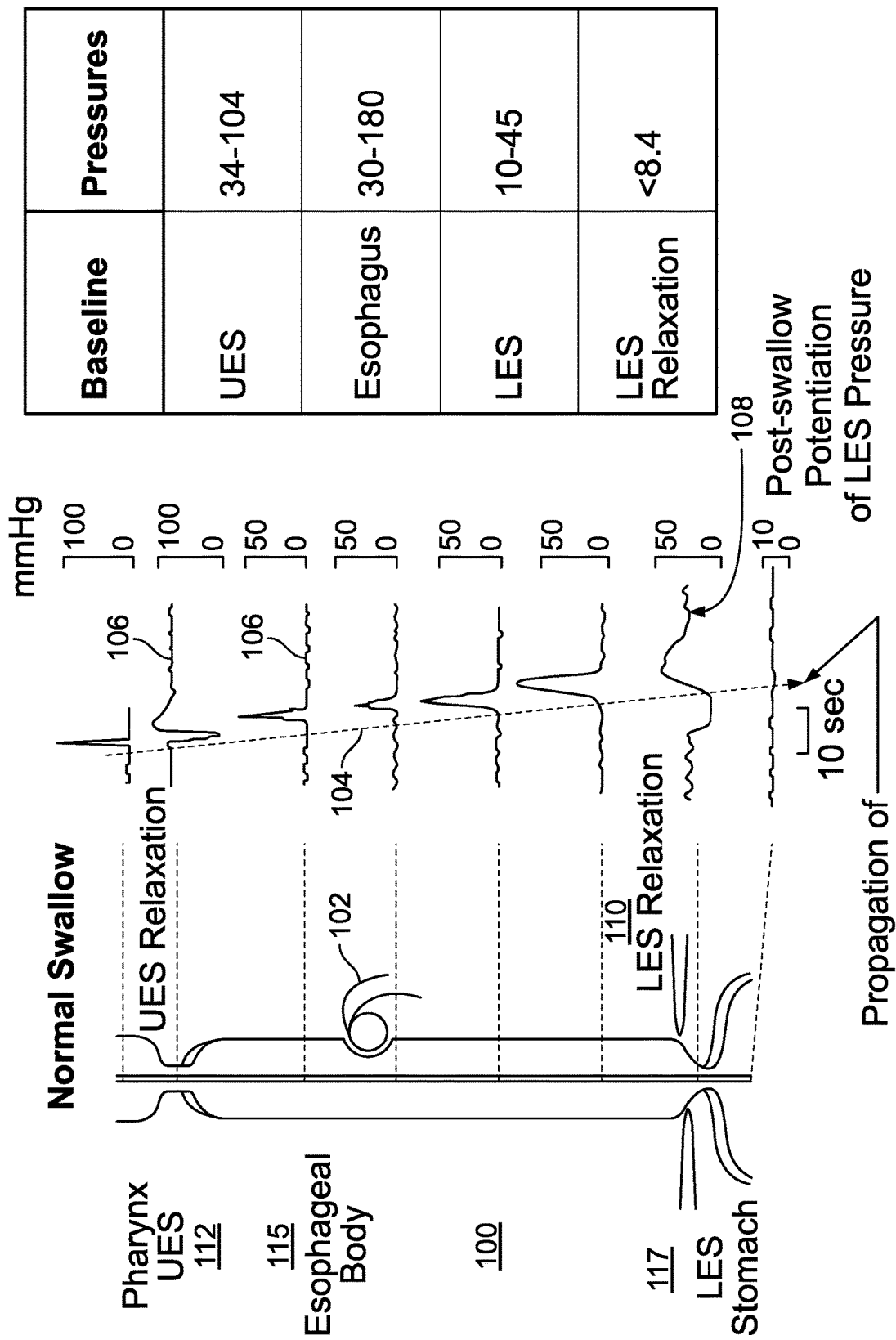
FIG. 1 is a graph depicting the physiology, including pressure measurements, of a normal swallow.

The present specification discloses programmable implantable electro-medical devices for the treatment of gastro-esophageal reflux disease (GERD). The present specification discloses systems and methods for treating gastroesophageal reflux disease (GERD) in a patient by electrically stimulating a portion of the lower esophagus and/or stomach to cause an increase in the length of the high pressure zone of the lower esophageal sphincter (LES). In one embodiment, the systems and methods of the present specification increase the length of the high pressure zone of the LES without changing the manometric maximum pressure in the region of the LES. In other words, the stimulation provided by the systems enhances the length of the high pressure zone but does not change overall pressure.

In one embodiment, the systems for increasing the length of the LES high pressure zone provide electrical stimulation in the LES. In another embodiment, the systems provide electrical stimulation to the gastric cardia. In another embodiment, the systems provide electrical stimulation both in the LES and to the gastric cardia. In another embodiment, the systems provide electrical stimulation to an area proximate the LES. In one embodiment, the area proximate the LES is within 3 cm of the LES. In another embodiment, the systems provide electrical stimulation both in the LES and to an area proximate the LES. In another embodiment, the systems provide electrical stimulation to both the gastric cardia and an area proximate the LES. In yet another embodiment, the systems provide electrical stimulation in the LES, to the gastric cardia, and to an area proximate the LES. In other embodiments, the systems for increasing the length of the LES high pressure zone provide electrical stimulation to other gastrointestinal structures, including but not limited to, any portion of the stomach.

With regards to the present specification, the high pressure zone of the lower esophageal sphincter (LES) is defined as a portion of the esophagus proximate the LES of a patient wherein the intra-esophageal pressure measures greater than the intra-esophageal pressure of the esophagus immediately proximal and distal to said portion. Pressures averaging over 5 mm Hg are considered to be in the high pressure zone. The average length of the LES is approximately 3 to 5 cm and includes a high pressure zone that is typically greater than 1 cm in length (for example, 1 to 5 cm). In a patient suffering from GERD, this high pressure zone is typically shortened. The systems of the present specification targeted at increasing the length of the LES high pressure zone enhance said high pressure zone in diseased patients by increasing its length while not necessarily increasing the overall maximum pressure within the zone. In one embodiment, the systems targeted at increasing the length of the LES high pressure zone increase the length of said high pressure zone of the LES by at least 10% compared to a baseline length before stimulation. For example, a patient has an LES with a high pressure zone measuring 2 cm in length wherein the pressure is over 5 mm Hg with a maximum of 10 mm Hg. Using various systems and methods of the present specification, the length of the LES having a pressure greater than 5 cm is increased to 3 cm while the maximum pressure remains at 10 mm Hg. Therefore, the length of the high pressure zone has been enhanced while the overall pressure remains unchanged.

Electrical stimulation of the anatomical structures proximate the LES results in activation of additional muscle fibers proximal and distal to the high pressure zone, causing these muscles to contract and thereby narrow the lumen of the esophagus. Pressure increases above 5 mm Hg in these constricted portions of the esophagus, resulting in an increase in the length of the high pressure zone. As such, various systems and methods of the present specification act to treat GERD by creating a longer barrier (longer high pressure zone) in the esophagus to prevent the reflux of acidic gastric contents.

The present specification also discloses systems and methods for treating gastroesophageal reflux disease (GERD) in a patient by electrically stimulating a portion of the lower esophagus and/or stomach to cause an increase in the receptive relaxation response of the fundus of the stomach. The increase in the relaxation response of the fundus leads to mechanical changes in the wall of the fundus, resulting in an increase in gastric size and volume and a decrease in gastric pressure. The decrease in gastric pressure translates to an increase in functional lower esophageal sphincter (LES) pressure, where functional LES pressure is defined as the relationship between actual LES pressure and actual gastric pressure, or a gastroesophageal pressure gradient. The increase in functional LES pressure treats GERD by creating a stronger barrier at the gastroesophageal junction (GEJ), preventing the reflux of gastric contents into the esophagus.

In one embodiment, the systems for increasing the relaxation response of the fundus provide electrical stimulation in the LES. In another embodiment, the systems provide electrical stimulation to the fundus of the stomach. In another embodiment, the systems provide electrical stimulation both in the LES and to the fundus. In another embodiment, the systems provide electrical stimulation to an area proximate the LES. In one embodiment, the area proximate the LES is within 3 cm of the LES. In another embodiment, the systems provide electrical stimulation both in the LES and to an area proximate the LES. In another embodiment, the systems provide electrical stimulation to both the fundus and an area proximate the LES. In yet another embodiment, the systems provide electrical stimulation in the LES, to the fundus, and to an area proximate the LES. In other embodiments, the systems for increasing the relaxation response of the fundus provide electrical stimulation to other gastrointestinal structures, including but not limited to, any portion of the stomach.

Providing electrical stimulation to the anatomical areas in and around the fundus of the stomach to enhance receptive relaxation can have a number of beneficial effects upon the gastrointestinal tract with regards to acid reflux. For example, in one embodiment, stimulation produces changes in post-prandial gastric geometry. These changes in geometry include an increase in gastric size and volume resulting in a decrease in gastric pressure. Normal gastric pressure averages approximately 10 mm Hg, which varies with breathing. In one embodiment, the systems and methods of the present specification targeted at increasing the relaxation response of the fundus cause a decrease in average gastric pressure to below 10 mm Hg. In one embodiment, the systems and methods targeted at increasing the relaxation response of the fundus cause a decrease in average gastric pressure by at least 10% compared to a baseline gastric pressure before stimulation. The functional LES pressure, as described above, is a pressure gradient relating the actual LES pressure to the actual gastric pressure. As the actual gastric pressure decreases, the functional LES pressure increases while the actual LES pressure remains the same. An increase in functional LES pressure results in fewer reflux events as the gastric contents must travel against a greater pressure gradient to enter back into the esophagus. In one embodiment, the systems and methods targeted at increasing the relaxation response of the fundus cause an increase in the functional LES pressure by at least 10%.

In one embodiment, electrical stimulation is applied after a patient eats to provide relief from post-prandial reflux. In this embodiment, the electrical stimulation enhances the receptive relaxation already occurring as a result of the contact of ingested food with stretch receptors on the stomach wall. In one embodiment, electrical stimulation is applied during fasting and during sleep times. Gastric wall relaxation in this embodiment occurs only as a result of the electrical stimulation and helps prevent reflux events not associated with eating. In one embodiment, a diabetic patient receives electrical stimulation in accordance with the systems and methods of the present specification. In this embodiment, the electrical stimulation acts to restore the receptive relaxation of the fundus which has become deficient in the diabetic patient.

In one embodiment, modulating (reducing) the tone of the fundus through electrical stimulation provided by the systems and methods of the present specification reduces the number of transient lower esophageal sphincter relaxation (tLESR) events. In one embodiment, the systems and methods of the present specification targeted at increasing the relaxation response of the fundus reduce the number of tLESR events by at least 10%. In another embodiment, modulating (reducing) the tone of the fundus through electrical stimulation provided by the systems and methods of the present specification does not affect the number of tLESR events but rather reduces the likelihood that reflux will occur during a tLESR event. This occurs as a result of decreasing gastric pressure and increasing functional LES pressure. Although the LES relaxes and actual LES pressure decreases for a short period of time, the decrease in gastric pressure resulting from the reduction in gastric tone as provided by said systems is great enough to prevent reflux. In other words, in one embodiment, the decrease in actual gastric pressure is greater than the decrease in actual LES pressure such that functional LES pressure is still increased, thereby preventing reflux. In one embodiment, the systems and methods targeted at increasing the relaxation response of the fundus reduce the likelihood of reflux during a tLESR event by at least 10%. In another embodiment, modulating (reducing) the tone of the fundus through electrical stimulation provided by the systems and methods of the present specification reduces the number of tLESR events and reduces the likelihood that reflux will occur during a tLESR event.

In one embodiment, the systems and methods of the present specification targeted at increasing the relaxation response of the fundus modulate acid pocket geometry within the gastroesophageal junction (GEJ). Acid pockets form within the GEJ of patients having GERD. Acid pockets form in a patient with GERD as the pressure gradient at the GEJ approaches zero. Approximately equal LES pressure and gastric pressure push against one another at the GEJ, trapping acid in small pockets in and around the GEJ in patient with GERD. As gastric pressure increases while LES pressure decreases or remains constant, the functional LES pressure decreases and the acid pockets are pushed up into the esophagus, resulting in esophageal acid exposure. Persons without GERD have no acid pockets. Acid pockets are defined by their length. Therefore, any pocket formation of acid having a length greater than 0 mm in the GEJ is considered an acid pocket in a GERD patient. In one embodiment, the systems and methods of the present specification targeted at increasing the relaxation response of the fundus reduce the occurrence of acid pockets by decreasing gastric pressure and increasing functional LES pressure thereby preventing the formation of acid pockets. In one embodiment, the occurrence of acid pockets in the GEJ is reduced by at least 10%. In one embodiment, the systems and methods targeted at increasing the relaxation response of the fundus reduce the size of acid pockets in the GEJ. As functional LES pressure is increased by some of the systems and methods of the present specification, acid pockets have less time to form in the GEJ. Therefore, the acid pockets that do form are smaller in size. In one embodiment, the systems and methods targeted at increasing the relaxation response of the fundus reduce the size of acid pockets in the GEJ by at least 10%.

In one embodiment, the systems and methods of the present specification targeted at increasing the relaxation response of the fundus control the content of the post-prandial reflux. In one embodiment, the systems and methods targeted at increasing the relaxation response of the fundus reduce the amount of acid in the reflux. In one embodiment, the amount of acid in the reflux is reduced by at least 10%.

In various embodiments, the efficacy of the above described therapy is determined by any one or combination of patient symptom reporting, esophageal pH monitoring, and esophageal impedance sensing. In various embodiments, changes in gastric geometry are determined using single-photon emission computed tomography (SPECT), magnetic resonance imaging (MRI), ultrasound, barostat, and assessment of intragastric pressure.

The systems and methods of the present specification targeted at increasing the relaxation response of the fundus are configured to achieve any one or combination of the following objectives: modulate muscle tone of the fundus, change gastric geometry, increase gastric size and/or volume, decrease gastric pressure, and increase functional LES pressure (defined as the relationship between actual LES pressure and actual gastric pressure), all with the goal of reducing at least one of a frequency of occurrence or an intensity of gastroesophageal reflux symptoms in said patient.

In various embodiments, the systems of the present specification employ stimulators, including macrostimulators or microstimulators, which can be implanted with minimal invasiveness in the gastrointestinal system. Specifically, these devices can be beneficial for deep implant locations for which there is a natural orifice access providing closer proximity than from outside the body. It should further be appreciated that the devices are capable of stimulating all smooth muscle, not limited to gastrointestinal (GI) smooth muscles and that the devices can additionally be used to deliver stimulation to the proximal stomach or area adjacent to the proximal stomach for treating various diseases that can be affected by gastric stimulation such as GERD, gastric motility problems and diabetes. The present application further incorporates by reference U.S. Pat. No. 6,901,295, PCT Patent Application Number PCT/US08/56479, and U.S. patent application Ser. Nos. 12/030,222, 11/539,645, 12/359,317, and 13/041,063 in their entirety.

The systems and methods disclosed herein can be used to achieve a plurality of different therapeutic objectives, including: treatment of GERD; normalizing a patient's LES function; treatment of hypotensive LES; increase resting or baseline LES pressure, aperistalsis of the esophagus; treating a patient to normalize esophageal pH, wherein said normalization is achieved when a patient has an esophageal pH value of less than 4 for a period of time no greater than 5%, 10%, or 15% of a 24 hour period or some fraction thereof; treating a patient to normalize esophageal pH when in the supine position, wherein said normalization is achieved when a patient has an esophageal pH value of less than 4 for a period of time no greater than 3% of a 24 hour period; treating a patient to prevent damage to the patient's lower esophageal sphincter caused by acid reflux; treatment of supine position induced diurnal GERD; treatment of activity-induced diurnal GERD; prevention of supine position induced diurnal GERD; prevention of activity-induced diurnal GERD; treating a patient to mitigate damage to the patient's lower esophageal sphincter caused by acid reflux; treating a patient to stop progression of damage to the patient's lower esophageal sphincter caused by acid reflux; treating a patient to minimize transient relaxations of the patient's lower esophageal sphincter; modifying or increasing LES pressure; modifying or increasing esophageal body pressure; modifying or improving esophageal body function; modifying or improving esophageal sensation induced by the refluxate; modifying or improving the volume of refluxate; modifying or improving the clearance of the refluxate; reducing incidents of heartburn; modifying or improving esophageal acid exposure; increasing lower esophageal tone; detecting when a patient swallows; detecting when a patient is eating; treating a gastrointestinal condition of a patient; treating a patient to minimize the patient's consumption of certain solids or liquids; reducing patient symptoms associated with diurnal gastrointestinal condition of a patient; treating a patient to minimize the patient's consumption of certain solids or liquids; reducing patient symptoms associated with GERD wherein such reduction is measured by an improvement in a patient quality of life survey and wherein said improvement is calculated by having a patient provide a first set of responses to said quality of life survey prior to treatment and having a patient provide a second set of responses to said quality of life survey after said treatment and comparing the first set of responses to said second set of responses; treating a patient for any of the above-listed therapeutic objectives with the additional requirement of avoiding tissue habituation, tissue fatigue, tissue injury or damage, or certain adverse reactions, including, but not limited to, chest pain, difficulty in swallowing, pain associated with swallowing, heartburn, injury to surrounding tissue, or arrhythmias. In various embodiments, the systems and methods disclosed herein can be used for treating a patient for any of the above-listed therapeutic objectives wherein said treatment effectuates a partial or complete closure at the gastric cardia without impeding normal swallow function in the patient. In other words, the gastric cardia is capable of opening for normal biological events while being stimulated.

The disclosed treatment methods may be practiced within, and devices may be implanted within, a plurality of anatomical regions to achieve one or more of the therapeutic objectives described above, including increasing the length of the LES high pressure zone and increasing the receptive relaxation response of the fundus to cause a decrease in gastric pressure with an increase in functional LES pressure (gastroesophageal gradient). Treatment sites, or implantation sites, include: the lower esophageal sphincter; within 3 cm above and 3 cm below the LES; proximate to the LES; in the vicinity of the LES; the esophageal body; the upper esophageal sphincter (UES); within, proximate to, or in the vicinity of the gastro-esophageal junction; the esophagus, including esophageal body, LES, and UES; proximate to the esophagus; in the vicinity of the esophagus; at or within the stomach, including the gastric cardia; nerves supplying the LES or gastro-esophageal junction; nerves supplying the esophageal body; nerves supplying the UES; or nerves supplying the esophagus, including the esophageal body, LES, and UES.

Additionally, it should be appreciated that a therapy which requires a lower amount of energy increases the long-term functionality of a stimulation device. Furthermore, accurate implantation of electrodes is imperative for improved efficacy and safety of these devices. Submucosa of organ systems, such as the area within the gastrointestinal tract between the muscularis mucosa and muscularis propria (two high impedance layers), have a relatively lower electrode-tissue interface impedance (referred to as impedance herein) and are therefore desirable locations for lead implantation and improved efficacy of stimulation. In addition, the loose connective tissue of the submucosa provides an improved environment for tunneling and creating pockets for lead implantation and microstimulator implantation. In one embodiment, the macrostimulator, microstimulator or their respective electrodes are implanted in the submucosa proximate to the LES, esophagus, or stomach to cause adjacent smooth muscle contraction using electrical field stimulation. Additional stimulator structures and/or electrodes may be placed in the adjacent muscularis or serosa and used in combination with the aforementioned macrostimulator or microstimulator. In another embodiment, the stimulator or electrodes are implanted in the gastrointestinal submucosa to cause gastrointestinal muscle contraction using electrical field stimulation. Additional stimulator structures and/or electrodes may be placed or proximate to in the adjacent gastrointestinal muscularis mucosa, gastrointestinal serosa, or gastrointestinal nerves.

Treatment Methodologies

The present invention is directed toward multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In one embodiment, any stimulator device, including a macrostimulator or microstimulator, is programmed to implement one or more treatment protocols disclosed herein. It should be appreciated that the treatment methods described below are implemented in a stimulator, such as a macrostimulator or microstimulator, having a plurality of electrodes, or at least one electrode, including, but not limited to, unipolar or bipolar electrodes, an energy source, such as a battery or capacitor, and a memory, whether local to the stimulator or remote from the stimulator and adapted to transmit data to the stimulator, which stores a plurality of programmatic instructions wherein said instructions, when executed by the macro/microstimulator, execute the stimulation therapies, as described below.

embodiment, a plurality of electrodes in electrical communication with a microstimulator is implanted predominantly in the submucosal layer, if done endoscopically, and in the muscularis layer if done laparoscopically.

In various embodiments, the stimulation parameters, which are effectuated through an electrical pulse that can be of any shape, including square, rectangular, sinusoidal or saw-tooth, may comprise any of the variable ranges detailed in the table below.

TABLE 1

| Pulse Type | Pulse Width | Pulse Frequency | Pulse Amplitude | On Cycle | Off Cycle |
| --- | --- | --- | --- | --- | --- |
| Short Pulse | 1-999 μsec | 1-100 Hz | Low (1-999 μAmp) Intermediate (1-50 mAmp) and any values therein | 0-24 hrs | 0-24 hrs |
| Intermediate Pulse | 1-250 msec | 1-100 Hz | Low (1-999 μAmp) Intermediate (1-50 mAmp) and any values therein | 0-24 hrs | 0-24 hrs |
| Intermediate Pulse | 1-250 msec | 1-59 cpm | Low (1-999 μAmp) Intermediate (1-50 mAmp) and any values therein | 0-24 hrs | 0-24 hrs |
| Long Pulse | 251 msec-1 sec | 1-59 cpm | Low (1-999 μAmp) Intermediate (1-50 mAmp) and any values therein | 0-24 hrs | 0-24 hrs |

The present specification discloses GERD treatment systems and methods that permit a patient, with one or more implanted stimulator systems as described above, to engage in a swallow that causes liquid, food mass, food mass mixed with liquid, or any bolus of matter greater than 1 cc to pass through the patient's esophagus (collectively referred to as a wet swallow or bolus swallow; wet swallow and bolus swallow shall be used interchangeably) while concurrently having one or more gastrointestinal anatomical structures, such as the upper esophagus, upper esophageal sphincter, esophagus, lower esophageal sphincter, the distal esophagus, the stomach, the gastric cardia, gastric fundus, and/or the vagus nerve, or any of the other anatomical structures described herein, be subjected to electrical stimulation.

The prior art has conventionally taught that stimulation of gastrointestinal structures, particularly the esophagus and lower esophageal sphincter, must cease when a patient engages in a swallow. It has now been unexpectantly determined that, if stimulated appropriately, such stimulation need not cease during, concurrent with, or in response to a patient engaging in a wet swallow. The stimulation protocols, described below, are effectuated through the stimulation devices described herein and by the patent documents incorporated herein by reference. Such devices generally include any device for electrical stimulation of one or more structures in the esophagus and for use in the treatment of GERD, comprising a pulse generator providing electrical stimulation, a power source for powering the pulse generator, one or more stimulating electrodes operatively coupled or connected to the pulse generator wherein the electrode sets are adapted to be positioned within or adjacent to one or more anatomical structures described herein. Preferably, the stimulating electrodes are designed to be implanted predominantly in the submucosal layer or the muscularis layer of the esophagus. In one embodiment, a plurality of electrodes in electrical communication with a macrostimulator is implanted predominantly in the muscularis propria. In one In some embodiments, the stimulation parameters used to increase the length of the high pressure zone of the LES and/or increase the relaxation response of the fundus include a pulse amplitude with a range of 3-20 mAmp, a pulse width with a range of 100 μsec-1 msec, a pulse frequency with a range of 2 Hz-100 kHz, and a range of 3-24 sessions per day. In one embodiment, the stimulation parameters used to increase the length of the high pressure zone of the LES and/or increase the relaxation response of the fundus include a pulse amplitude of 5-6 mAmp, a pulse width of 215 μsec, a pulse frequency of 20 Hz, and 6-12 sessions per day. In other embodiments, the stimulation parameters used to increase the length of the high pressure zone of the LES and/or increase the relaxation response of the fundus include: a pulse width having a range of 30 μsec to 5 msec; a pulse amplitude having a range of 2 to 15 mAmp; an on period ranging from 1 second to 23 hours, 59 minutes, and 59 seconds; an off period ranging from 1 second to 23 hours, 59 minutes, and 59 seconds; a duty cycle ranging from 1 to 100%; and, a pulse frequency. In some embodiments, the pulse frequency has a range of 1-100 Hz or 1-59 cpm.

In various embodiments, the present specification discloses a method for treating GERD by electrically stimulating a lower esophageal sphincter or nerve supplying the LES, an esophageal smooth muscle or a nerve supplying the esophageal smooth muscle, the gastric cardia or a nerve supplying the gastric cardia, and/or an area proximate the LES that causes an increase in the length of the high pressure zone of the LES and/or an increase in the relaxation response of the fundus without affecting, preventing, prohibiting, or otherwise hindering a bolus swallow induced relaxation of the lower esophageal sphincter or bolus swallow induced esophageal body motility. In these embodiments, because electrical stimulation need not be inhibited, there is no need to sense for the bolus swallow in order to trigger a cessation of electrical stimulation and, therefore, a stimulator need not be programmed to sense for the bolus swallow, to modify stimulation in response to a bolus swallow (even if the stimulation device has sensing capabilities), or to be otherwise responsive to a bolus swallow. In one embodiment, the present specification discloses a method for treating GERD by electrically stimulating a lower esophageal sphincter or nerve supplying the LES, an esophageal smooth muscle or a nerve supplying the esophageal smooth muscle, the gastric cardia or a nerve supplying the gastric cardia, and/or an area proximate the LES that causes an increase in the length of the high pressure zone of the LES without necessarily increasing the overall maximum pressure within the esophagus.

These stimulation processes normalizes lower esophageal sphincter function because they increase the length of the high pressure zone of the LES and/or increase the relaxation response of the fundus while not prohibiting or preventing a natural bolus swallow. These processes also a) do not affect gastric distension induced relaxation of the lower esophageal sphincter, b) improve the post bolus swallow augmentation of the LES pressure, and c) improve the esophageal body function, among other therapeutic benefits, as described above.

Having eliminated the need to dynamically control the electrical stimulation based on swallow sensing, the system can be allowed to engage in automated "on/off" duty cycles that can range from 1 second to 24 hours. During the "on" period, stimulation is preferably applied for a long enough period to enable recruitment of adequate nerves and/or muscle fibers to achieve the desired pressure, function or effect. The desired "on" period is patient specific and is preferably calculated based on the time required to increase the LES high pressure zone to a length at least 10% greater than baseline plus additional time to maintain the length enhancement (maintenance time) or to decrease gastric pressure by at least 10% plus additional time to maintain the reduced gastric pressure (maintenance time). In one embodiment, the maintenance time ranges from 1 second to 12 hours. While sensors are not required, in one embodiment, the "on" period can be determined, or triggered by, sensors that sense changes in the LES, such as LES pressure changes, or changes in the esophagus. Those sensing electrodes sense one or more of changes in gastrointestinal muscle tone or impedance, peristaltic activity, esophageal peristalsis, esophageal pH, esophageal pressure, esophageal impedance, esophageal electrical activity, gastric peristalsis, gastric electrical activity, gastric chemical activity, gastric hormonal activity, gastric temperature, gastric impedance, electrical activity, gastric pH, blood chemical and hormonal activity, vagal or other gastrointestinal neural activity and salivary chemical activity and can be preferably positioned in or adjacent one or more of the esophagus, the stomach, the small intestine, the colon, the vagus or other gastrointestinal nerves and the vascular system.

The "off" period is preferably set in order to prevent development of tolerance or muscle fatigue, to improve device functionality, and to optimize energy consumption from the battery. The desired "off" period ranges from 1 second to 24 hours. The desired "off" period is patient specific and calculated based on the time required to change the LES high pressure zone length from its therapeutic value to the baseline value plus optional additional time to maintain the baseline length (relaxation time) or for the gastric pressure to return to its pre-treatment value plus optional additional time to maintain the baseline pressure (relaxation time). In one embodiment, the relaxation time ranges from 1 second to 12 hours. While sensors are not required, in one embodiment, the "off" period can be determined, or triggered by, sensors that sense changes in the LES, such as pressure, or changes in the esophagus. Those sensing electrodes sense one or more of changes in gastrointestinal muscle tone or impedance, peristaltic activity, esophageal peristalsis, esophageal pH, esophageal pressure, esophageal impedance, esophageal electrical activity, gastric peristalsis, gastric electrical activity, gastric chemical activity, gastric hormonal activity, gastric temperature, gastric impedance, gastric pH, blood chemical and hormonal activity, vagal or other gastrointestinal neural activity and salivary chemical activity and can be preferably positioned in or adjacent one or more of the esophagus, the stomach, the small intestine, the colon, the vagus or other gastrointestinal nerves and the vascular system.

Accordingly, in various embodiments, stimulation can be provided for a first period to generate an increase in the length of the LES high pressure zone of a first threshold level, then the stimulation can be lowered or removed while still maintaining the increase in the length of the LES high pressure zone at or above the first threshold level of high pressure zone length, thereby treating GERD and other gastrointestinal indications. Stimulation of greater than a first threshold level of LES high pressure zone length can be delivered within a time period of less than a first time period, thereby treating certain gastrointestinal indications. In one embodiment, the present specification discloses a treatment method in which stimulation, such as at or under 30 mAmp, 15 mAmp, 10 mAmp, 8 mAmp, or any increment therein, is applied to achieve an increase in LES high pressure zone length of less than a first threshold level and, concurrently, wet swallows are still enabled without terminating or decreasing the stimulation. In one embodiment, the present specification discloses a treatment method in which stimulation, such as at or under 30 mAmp, 15 mAmp, 10 mAmp, 8 mAmp, or any increment therein, is applied and then terminated, after which the length of the LES high pressure zone increases beyond a first threshold level and, concurrently, wet swallows are still enabled. It should be appreciated that the stimulation parameters can be presented in terms of total energy applied. For example, the current stimulation parameters can be replaced, throughout this specification, with preferred energy levels, such as at or under 6 millicoulombs (mC), 3 mC, 1 mC, 0.08 mC, or any increment therein.

In other embodiments, stimulation can be provided for a first period to generate a decrease in gastric pressure of a first threshold level, then the stimulation can be lowered or removed while still maintaining the decrease in gastric pressure at or below the first threshold level, thereby treating GERD and other gastrointestinal indications. Stimulation of greater than a first threshold level of gastric pressure can be delivered within a time period of less than a first time period, thereby treating certain gastrointestinal indications. In one embodiment, the present specification discloses a treatment method in which stimulation, such as at or under 30 mAmp, 15 mAmp, 10 mAmp, 8 mAmp, or any increment therein, is applied to achieve a decrease in gastric pressure of less than a first threshold level and, concurrently, wet swallows are still enabled without terminating or decreasing the stimulation. In one embodiment, the present specification discloses a treatment method in which stimulation, such as at or under 30 mAmp, 15 mAmp, 10 mAmp, 8 mAmp, or any increment therein, is applied and then terminated, after which gastric pressure decreases beyond a first threshold level and, concurrently, wet swallows are still enabled. It should be appreciated that the stimulation parameters can be presented in terms of total energy applied. For example, the current stimulation parameters can be replaced, throughout this specification, with preferred energy levels, such as at or under 6 millicoulombs (mC), 3 mC, 1 mC, 0.08 mC, or any increment therein.

It should further be appreciated that the treatment methodologies disclosed herein adjust for, take advantage of, account for, or otherwise optimally use a delayed, or latent, pressure response from the LES in response to electrical stimulation. Conventionally, the prior art has taught that the LES instantaneously responds, either by contracting or relaxing, to the application of, or removal of, electrical stimulation. In the present treatment methodologies, the LES has a delayed or latent response to electrical stimulation, thereby resulting in a gradual increase in the length of the LES high pressure zone and/or a gradual decrease in gastric pressure after the application of electrical stimulation and a sustained increased length of the LES high pressure zone and/or decrease in gastric pressure after electrical stimulation is terminated, at least for certain stimulation parameters. Accordingly, a desired normalization of LES function can be achieved well in advance of an expected GERD triggering event, such as eating, sleeping, napping, laying down, being in a supine position, bolus swallowing, or engaging in physical activity, by applying electrical stimulation before the GERD triggering event and then terminating the stimulation prior to, during, or after the GERD triggering event. Multiple embodiments of the present specification take advantage of this delayed response by stimulating the LES in a manner that does not cause immediate contraction of the musculature or an immediate increase in LES high pressure zone length or immediate decrease in gastric pressure. For example, in one embodiment, stimulation is directed to the LES at a level of no more than 6 mC repeated on a regular basis, for example 20 times a second, for a specific period of time, for example 30 minutes. This results in lengthening of the LES high pressure zone and/or a decrease in gastric pressure that does not occur until after the initial 5 minutes of stimulation and that continues once stimulation has been terminated. In one embodiment, stimulation is directed to the LES at a level of no more than 6 mC repeated on a regular basis, for example 20 times a second, for a specific period of time, for example 30 minutes. This results in contraction of the LES and an increase in the length of the LES high pressure zone and/or a decrease in gastric pressure that does not occur until after the initial stimulation has been initiated and that continues or persists once stimulation has been terminated.

In these stimulation methodologies, a sub-threshold stimulation that does not generate an instantaneous LES or esophageal function response is applied for a predefined duration of time to achieve a therapeutic response. In one embodiment, sub-threshold stimulation means that an applied stimulation does not substantially instantaneously achieve contraction of the LES. Sub-threshold stimulation may have stimulation parameters of less than 20 mAmp, less than 10 mAmp, or less than 8 mAmp. In one embodiment, a threshold or above threshold stimulation means that an applied stimulation substantially instantaneously achieves contraction of the LES and may have stimulation parameters of greater than 20 mAmp, greater than 10 mAmp, or greater than 8 mAmp. Sub-threshold stimulation has multiple advantages, including improved device functionality, improved energy transfer in a wireless microstimulator, improved patient safety, decreased patient adverse symptoms or side effects and decreased tolerance and/or fatigue.

Referring to FIG. 1, a normal esophageal pressure profile 100 is shown. With deglutition, the peristaltic wave follows immediately after the upper esophageal sphincter (UES) relaxation, producing a lumen-occluding contraction of the esophageal circular muscle. The contraction wave migrates aborally at a speed that varies along the esophagus. The peristaltic velocity averages about 3 cm/sec in the upper esophagus, then accelerates to about 5 cm/sec in the mid-esophagus, and slows again to approximately 2.5 cm/sec distally. The duration and amplitude of individual pressure waves also varies along the esophagus. The duration of the wave is shortest in the proximal esophagus (approximately 2 seconds) and longest distally (approximately 5 to 7 seconds). Peak pressures average 53±9 mmHg in the upper esophagus, 35±6 mmHg in the mid-portion, and 70±12 mmHg in the lower esophagus. These parameters can be influenced by a number of variables including bolus size, viscosity, patient position (e.g., upright vs. supine), and bolus temperature. For instance, a large bolus elicits stronger peristaltic contractions that migrate distally at a slower rate than a small bolus. The peristaltic velocity is also slowed by outflow obstruction or increases in intra-abdominal pressure. Warm boluses tend to enhance, whereas cold boluses inhibit, the amplitude of peristaltic contractions.

Accordingly, bolus 102 propagates through the UES 112, esophageal body 115, and LES 117 over a period of approximately, and typically, ten seconds. As the bolus 102 moves through the esophagus, portions of the UES 112, esophageal body 115, and LES 117 experience an increase in pressure. In a normal person, the baseline pressure range for the UES 112 is between 34 and 104 mmHg, for the esophagus 115 is between 30 and 180 mmHg, and for the LES 117 is between 10 and 45 mmHg. At the point of LES relaxation 110, which occurs to permit the bolus to pass through into the stomach, the LES pressure decreases to below approximately 8.4 mmHg. Notably, in a normal patient, post-swallow, the LES pressure increases, after having decreased for the swallow, and then remains at a higher baseline pressure level than just immediately prior to the swallow.

In various embodiments, the presently disclosed systems and methods return an abnormally functioning LES to a state of normalcy, post-stimulation or post initiation of stimulation. The treatment methodology comprises implanting a stimulation device, as described herein, and electrically stimulating the device to cause an increase in the length of the LES high pressure zone and/or an increase in functional LES pressure by decreasing actual gastric pressure through modulation of the tone of the fundus, in accordance with any of the stimulation methodologies described herein. After stimulation is terminated, one or more of the following functional parameters, characteristic of an abnormally functioning LES, achieves normal physiological range: a) LES basal pressure (respiratory minima) returns to a range of 15-32 mmHg, b) LES basal pressure (respiratory mean) returns to a range of 10-43 mmHg, c) LES residual pressure returns to a range of less than 15 mmHg, d) LES percent relaxation returns to a range of greater than 40%, e) LES duration of contraction returns to a range of 2.9 seconds to 5.1 seconds (3 cm above the LES), 3 seconds to 5 seconds (8 cm above the LES), or 2.8 seconds to 4.2 seconds (13 cm above the LES), f) lower esophageal acid exposure during 24-hour pH-metry returns to a range of pH<4 for less than 10%, and preferably less than 5%, of total or less than 8% or preferably less than 3% of supine time, and/or g) esophageal reflux events return to less than 100 per 24 hour period or reduce by 50% as documented by impedance pH monitoring, i) normal bolus swallows return with complete bolus transit, defined as detection of bolus exit in all 3 of the distal impedance channels and/or j) esophageal pH returns to a range equal to twice the normal, as defined in the table below or any normative standards for the measuring device.

TABLE 2

Catheter-based dual-probe (distal and proximal) esophageal pH monitoring

| Variable | Normal | |
| --- | --- | --- |
| | Proximal (%) | Distal (%) |
| Time pH < 4.0 (%) | | |
| Total period | <0.9 | <4.2 |
| Upright period | <1.2 | <6.3 |
| Recumbent period | <0.0 | <1.2 |

Distal = 5 cm above manometric defined proximal border of the LES.
Proximal = 20 cm above manometric defined proximal border of the LES.
Catheter free distal esophageal pH monitoring

| Variable | Normal Distal (%) |
| --- | --- |
| Time pH < 4.0 (%) | |
| Total period | <5.3 |
| Upright period | <6.9 |
| Recumbent period | <6.7 |

Distal = 6 cm above endoscopic defined gastroesophageal junction

Accordingly, the presently disclosed systems and methods modify one or more of the aforementioned functional parameters characteristic of an abnormally functioning LES or the esophagus to that of a normally or improved functioning LES or the esophagus, even after stimulation is terminated. By transforming an abnormally functioning LES or the esophagus to a normally or improved functioning LES or the esophagus, esophageal reflux, GERD, esophageal motility disorders or esophageal neural, muscular or neuromuscular disorders, can be effectively treated.

In another embodiment, the presently disclosed systems and methods modify an abnormally functioning LES or the esophagus to provide for an adequately functioning LES or esophagus post-stimulation. The treatment methodology comprises implanting a stimulation device, as described herein, and electrically stimulating the tissue to cause an increase in the length of the LES high pressure zone and/or an increase in functional LES pressure by decreasing actual gastric pressure through modulation of the tone of the fundus, in accordance with any of the stimulation methodologies described herein. After stimulation is terminated, one or more of the following functional parameters, characteristic of an abnormally functioning LES, returns to a physiological range sufficient to prevent esophageal reflux, GERD, esophageal motility disorders or esophageal neural, muscular or neuromuscular disorders: a) LES basal pressure, b) LES residual pressure, c) LES percent relaxation, d) LES duration of contraction, e) distal esophageal pH, f) esophageal reflux events, and g) esophageal body function. Accordingly, the present invention modifies physiological parameters characteristic of an abnormally functioning LES, relative to the patient's pre-treatment state, to that of an adequately functioning LES, even after stimulation is terminated. By transforming an abnormally functioning LES to an adequately functioning LES, esophageal reflux, GERD, esophageal motility disorders or esophageal neural, muscular or neuromuscular disorders can be effectively mitigated.

In another embodiment, the present specification enhances the length of the high pressure zone of an abnormally functioning LES and/or decreases gastric pressure post-stimulation. The treatment methodology comprises implanting a stimulation device, as described herein, and electrically stimulating the tissue to cause an increase length of the LES high pressure zone and/or an increase in functional LES pressure by decreasing actual gastric pressure through modulation of the tone of the fundus, in accordance with any of the stimulation methodologies described herein. After stimulation is terminated, in some embodiments, LES high pressure zone baseline length is increased, relative to the patient's pre-treatment state, by at least 5%, preferably 10%. After stimulation is terminated, in some embodiments, gastric pressure is decreased, relative to the patient's pre-treatment state, by at least 5%, preferably 10%. Accordingly, the presently disclosed methods and systems enhance the length of the high pressure zone of an abnomial functioning LES and/or decrease gastric pressure, even after stimulation is terminated. By doing so, esophageal reflux, GERD, esophageal motility disorders or esophageal neural, muscular or neuromuscular disorders can be effectively mitigated.

In another embodiment, the presently disclosed systems and methods improve, post-stimulation, at least one of a) esophageal body pressure, b) esophageal body contractility, c) esophageal body motility, d) esophageal body bolus transit, or e) esophageal body peristalsis, resulting in improved esophageal acid clearance after a reflux event, decreasing esophageal acid exposure time, and minimizing damage from exposure of esophageal mucosa to gastroduodenal refluxate. The treatment methodology comprises implanting a stimulation device, as described herein, and electrically stimulating the tissue to cause an increase in the length of the LES high pressure zone and/or an increase in functional LES pressure by decreasing actual gastric pressure through modulation of the tone of the fundus, in accordance with any of the stimulation methodologies described herein. After stimulation is terminated, at least one of a) esophageal body pressure, b) esophageal body contractility, c) esophageal body motility, e) esophageal body bolus transit, or f) esophageal body peristalsis improves and remains in an improved state while the stimulator is off.

In another embodiment, the presently disclosed systems and methods achieve any of the aforementioned therapeutic objectives by providing or implanting a stimulation device adapted to be implanted within the patient's lower esophageal sphincter, wherein the patient's esophagus has a function, and treating the patient by applying electrical stimulation, wherein the stimulation causes an improvement in esophageal function. Esophageal function may include any one of esophageal pressure, bolus transit, esophageal perception, esophageal accommodation or esophageal clearance of the refluxate.

In another embodiment, the presently disclosed systems and methods achieve any of the aforementioned therapeutic objectives by providing or implanting a stimulation device adapted to be implanted within the patient's lower esophageal sphincter, wherein the patient's esophagus has a function, and treating the patient by applying electrical stimulation, wherein the stimulation causes a non-instantaneous or delayed improvement in esophageal function. Esophageal function may include any one of esophageal pressure, bolus transit, esophageal perception, esophageal accommodation or esophageal clearance of the refluxate.

Figure 2A:
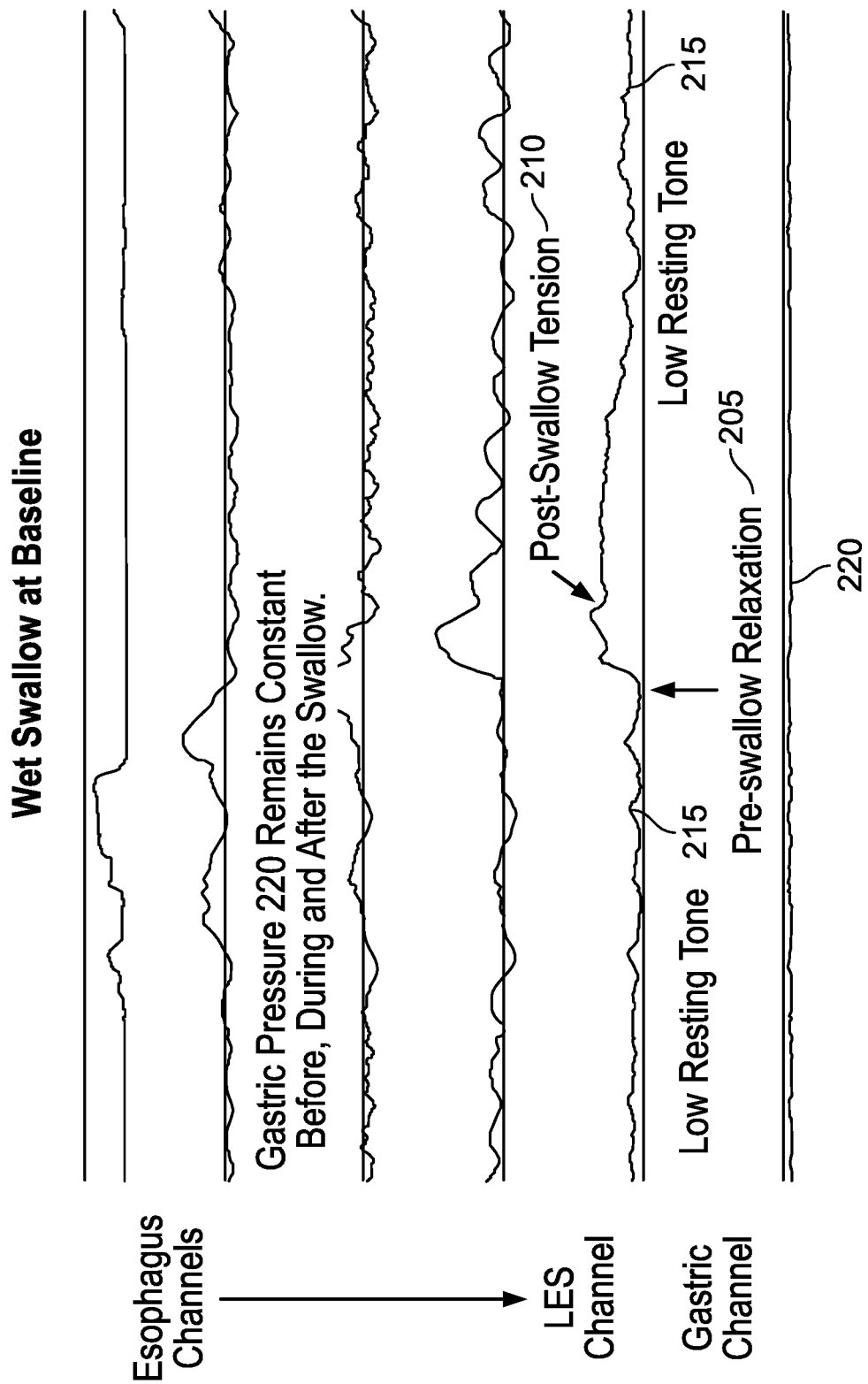
FIG. 2A is a graph depicting a wet swallow at baseline for a GERD patient.

FIG. 2A is a graph depicting a wet swallow at baseline for a GERD patient. In a typical GERD patient, the LES relaxes prior to a swallow 205. Post-swallow, the LES pressure increases 210, which can be observed for a short duration following the swallow, and then reverts to a resting tone 215. Gastric pressure 220 remains constant before, during, and after the swallow. In the absence of stimulation, gastric pressure 220 is under only neural control, and is designed to remain constant as the stomach expands and contracts with the ingestion and passage of food, respectively. It should be appreciated that the resting tone 215 of the LES in the GERD patient is too low to prevent reflux. The constant gastric pressure level 220 overcomes the low resting pressure 215 of the esophagus, causing reflux of gastric material into the esophagus.

Figure 2B:
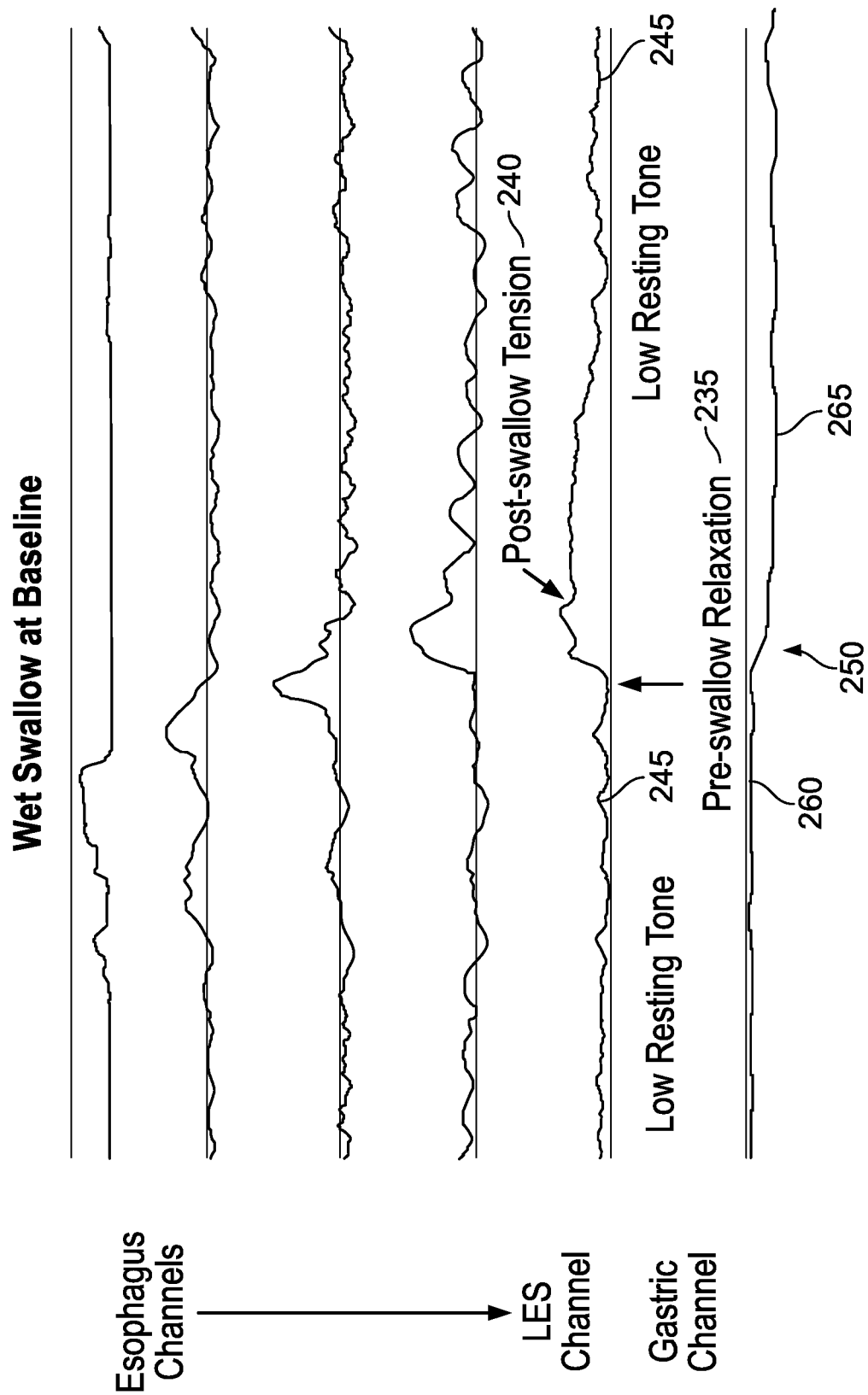
FIG. 2B is a graph depicting one embodiment of an improved wet swallow with stimulation.

FIG. 2B is a graph depicting one embodiment of an improved wet swallow with stimulation targeted at increasing the receptive relaxation response of the fundus. Again, in the typical GERD patient, the LES relaxes prior to a swallow 235. Post-swallow, the LES pressure increases 240, which can be observed for a short duration following the swallow, and then reverts to a resting tone 245. The low resting tone 245 of the abnormally functioning LES is not enough to prevent reflux. However, with stimulation 250, the gastric pressure decreases from its constant level 260 to a reduced level 265. The reduced gastric level 265 continues for a short time even after stimulation has ceased. The decrease in gastric pressure 265 is sufficient to result in an increase in functional LES pressure or the gastroesophageal pressure gradient, even with a low LES resting pressure 245. In other words, the decrease in gastric pressure 245 provided by the systems and methods of the present specification targeted at increasing the receptive relaxation response of the fundus is greater than the decrease in LES resting pressure 245 of the abnormally functioning LES. The relative higher pressure above the GEJ prevents gastric contents from refluxing into the esophagus.

Figure 2C:
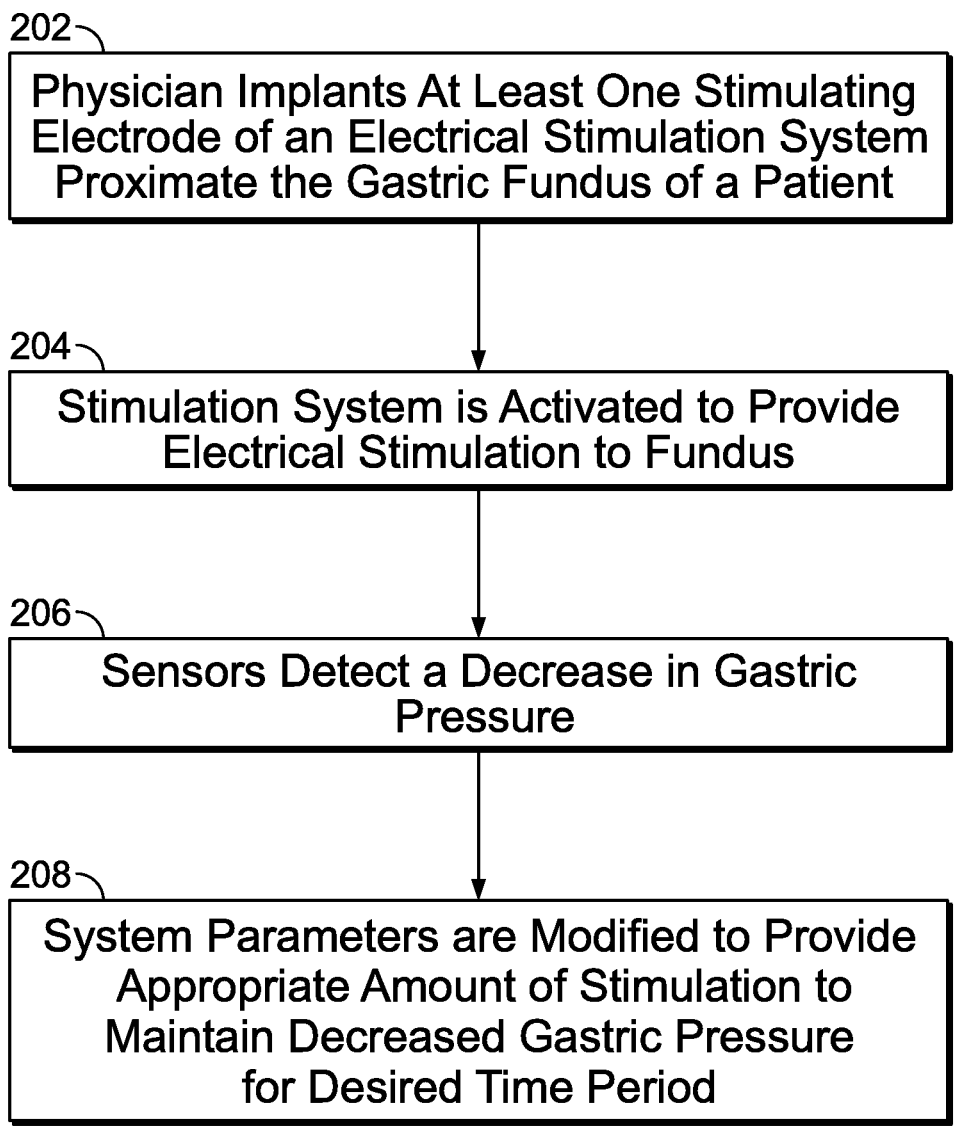
FIG. 2C is a flow chart illustrating the steps involved in one embodiment of a method of treating a patient with GERD by decreasing gastric pressure through electrical stimulation.

FIG. 2C is a flow chart illustrating the steps involved in one embodiment of a method of treating a patient with GERD by decreasing gastric pressure through electrical stimulation. At step 202, a physician implants at least one stimulating electrode of an electrical stimulation system in accordance with the various embodiments of the present specification proximate the gastric fundus of a patient. The system is then activated at step 204 to provide electrical stimulation to the fundus. Optionally, in one embodiment, a plurality of sensors positioned in the stomach detects decrease in gastric pressure at step 206. Optionally, at step 208, the system parameters are modified to provide an appropriate amount of stimulation to maintain the decrease in gastric pressure for a desire period of time in accordance with various treatment protocols of the present specification.

Figure 3A:
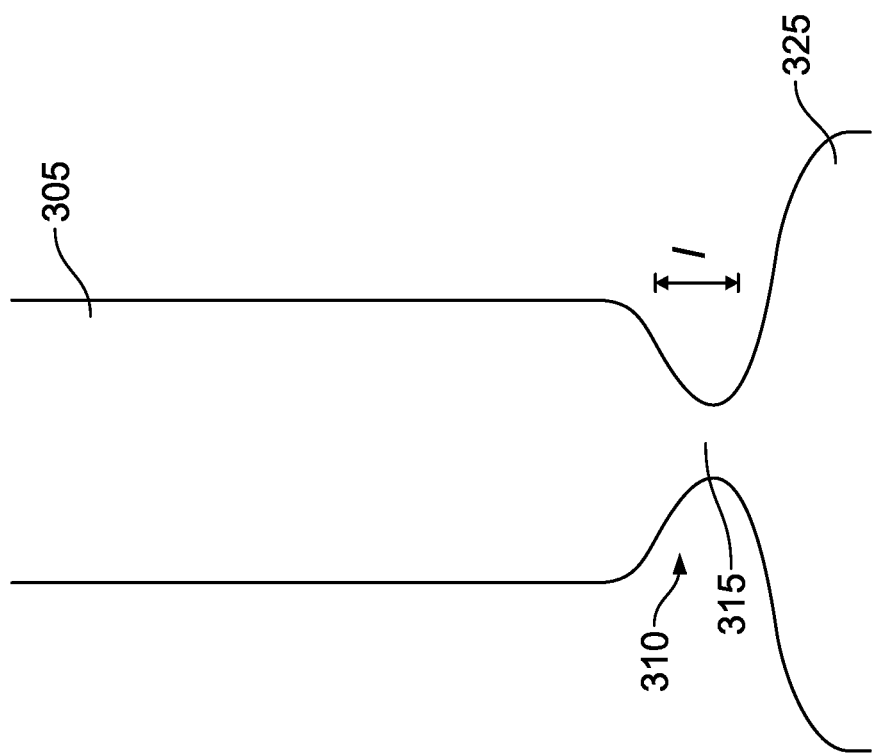
FIG. 3A is an illustration of the distal portion of an esophagus of a patient with gastroesophageal reflux disease (GERD)

FIG. 3A is an illustration of the distal portion of an esophagus 305 of a patient with gastroesophageal reflux disease (GERD). The patient's LES 310 does not function properly, allowing the reflux of gastric contents from the stomach 325 up into the esophagus 305. Referring to FIG. 3, the patient suffering from GERD has a shortened length 1 of the high pressure zone 315 of the LES 310. A patient with GERD can have a high pressure zone 315 with a length 1 less than 1 cm. This results from insufficient contraction of the circular muscle of the LES 310. The shortened high pressure zone 315 is inadequate in preventing gastroesophageal reflux.

Figure 3B:
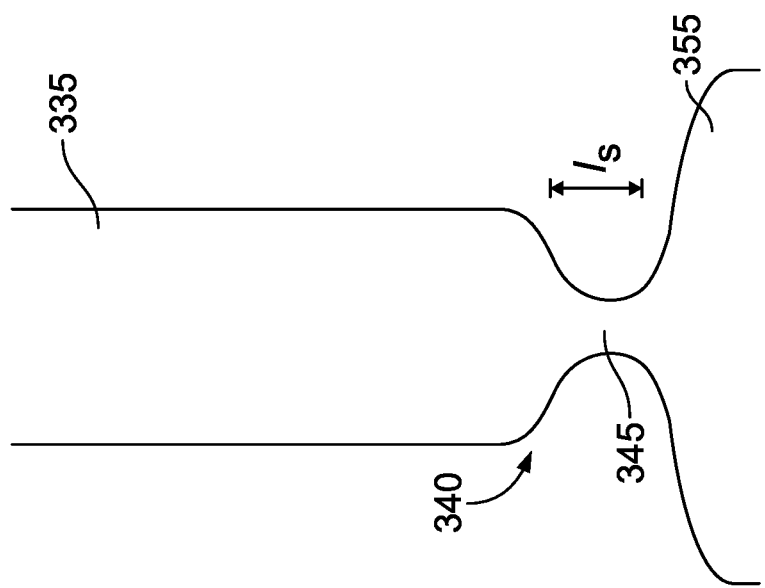
FIG. 3B is an illustration of the distal portion of an esophagus receiving stimulation targeted at increasing the length of the LES high pressure zone, in accordance with one embodiment of the present specification.

FIG. 3B is an illustration of the distal portion of an esophagus 335 receiving stimulation targeted at increasing the length of the LES high pressure zone 345, in accordance with one embodiment of the present specification. Electrical stimulation results in the recruitment of additional muscle fibers in the LES 340. A greater portion of the LES 340 contracts, resulting in an enhancement, or increase, in the length $l_s$, of the high pressure zone 345. In one embodiment, the length $l_s$ of a high pressure zone of an LES receiving stimulation represents an increase in length of at least 10% in relation to the length 1 of FIG. 3A of a high pressure zone of an LES prior to treatment. The longer high pressure zone 345 functions as a longer barrier to the reflux of gastric contents from the stomach 355 up into the esophagus 335, thereby effectively treating GERD.

Figure 3C:
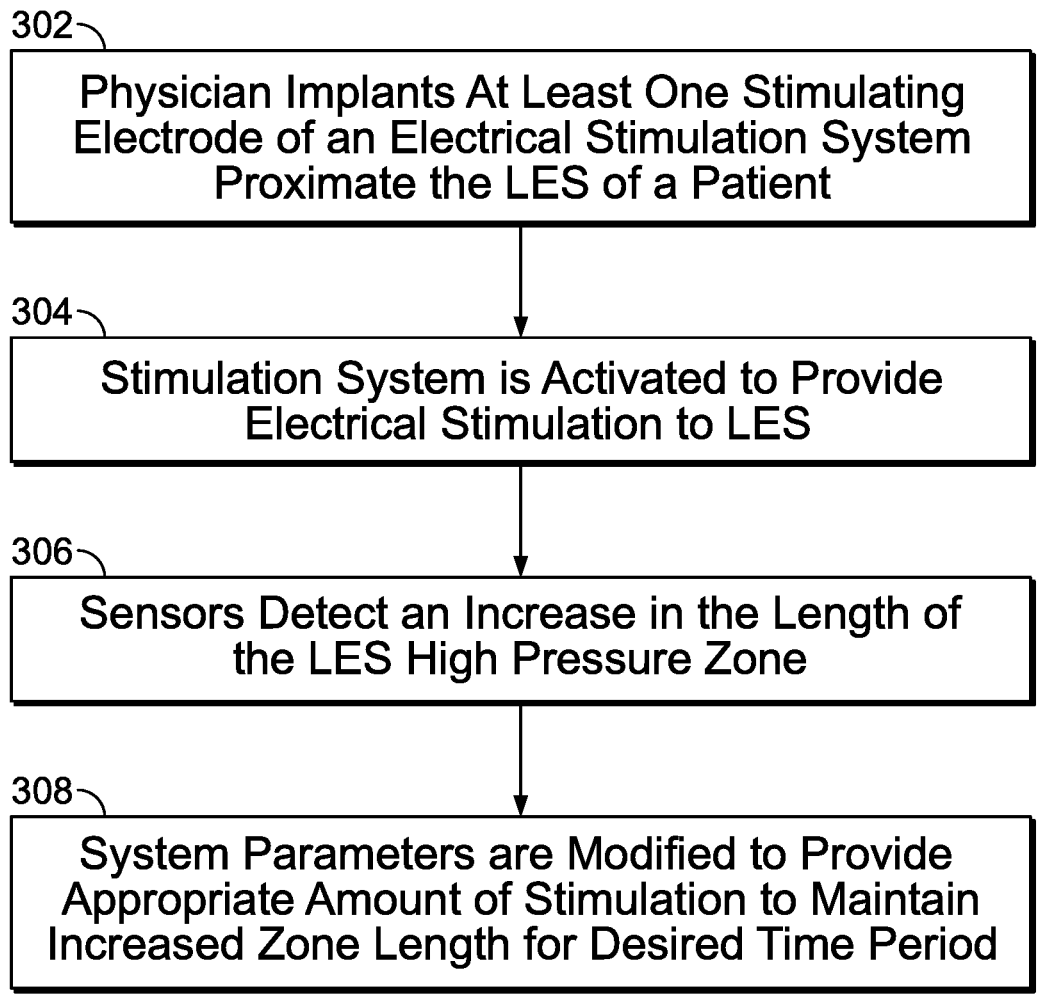
FIG. 3C is a flow chart illustrating the steps involved in one embodiment of a method of treating a patient with GERD by increasing the length of the LES high pressure zone through electrical stimulation.
Figure 4:
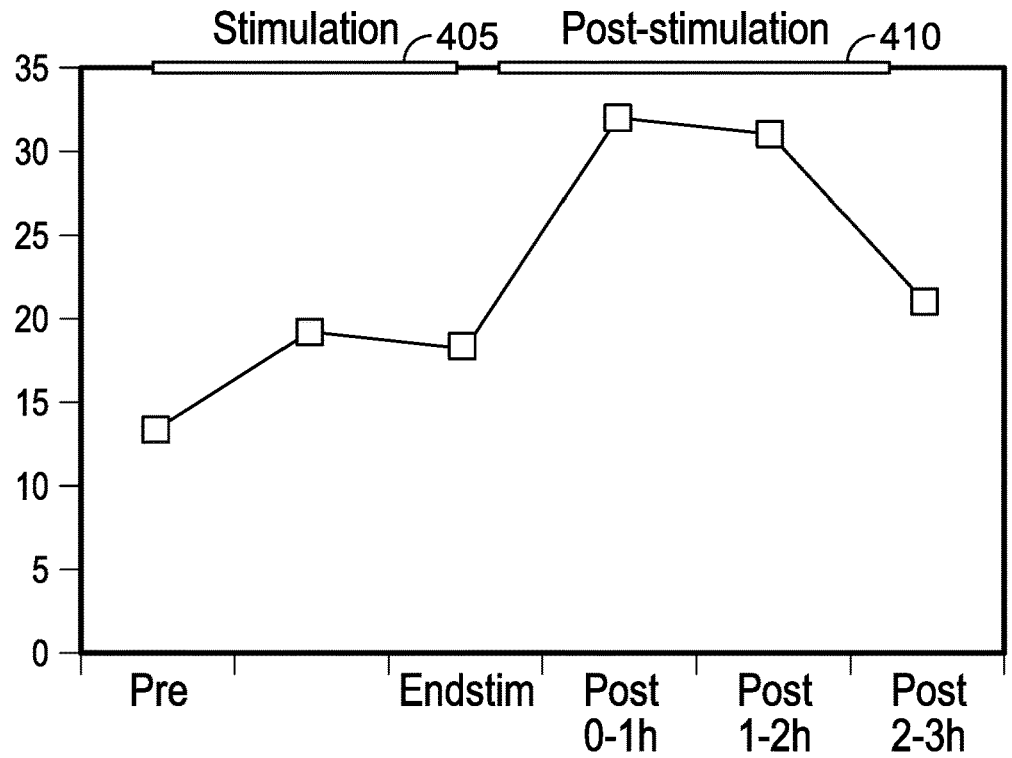
FIG. 4 is a graph depicting one exemplary pressure profile, both during stimulation and post-stimulation.
Figure 5:
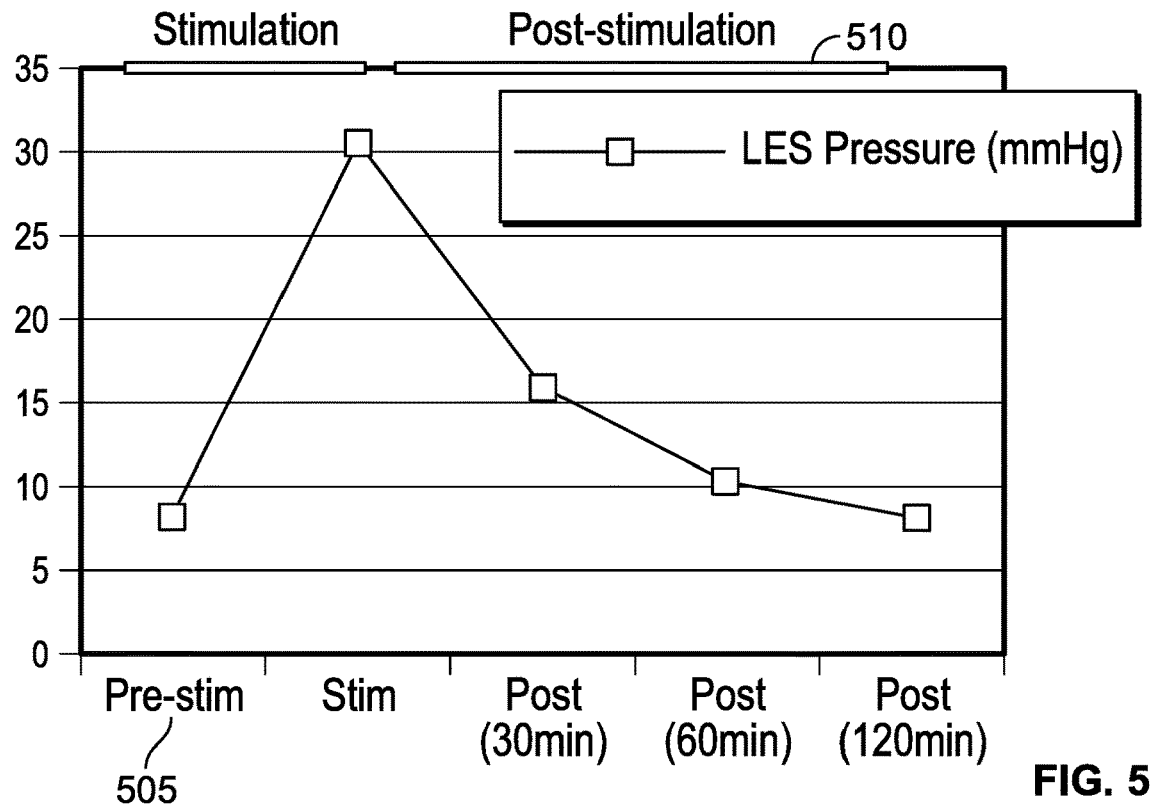
FIG. 5 is a graph depicting another exemplary pressure profile, both during stimulation and post-stimulation.
Figure 6:
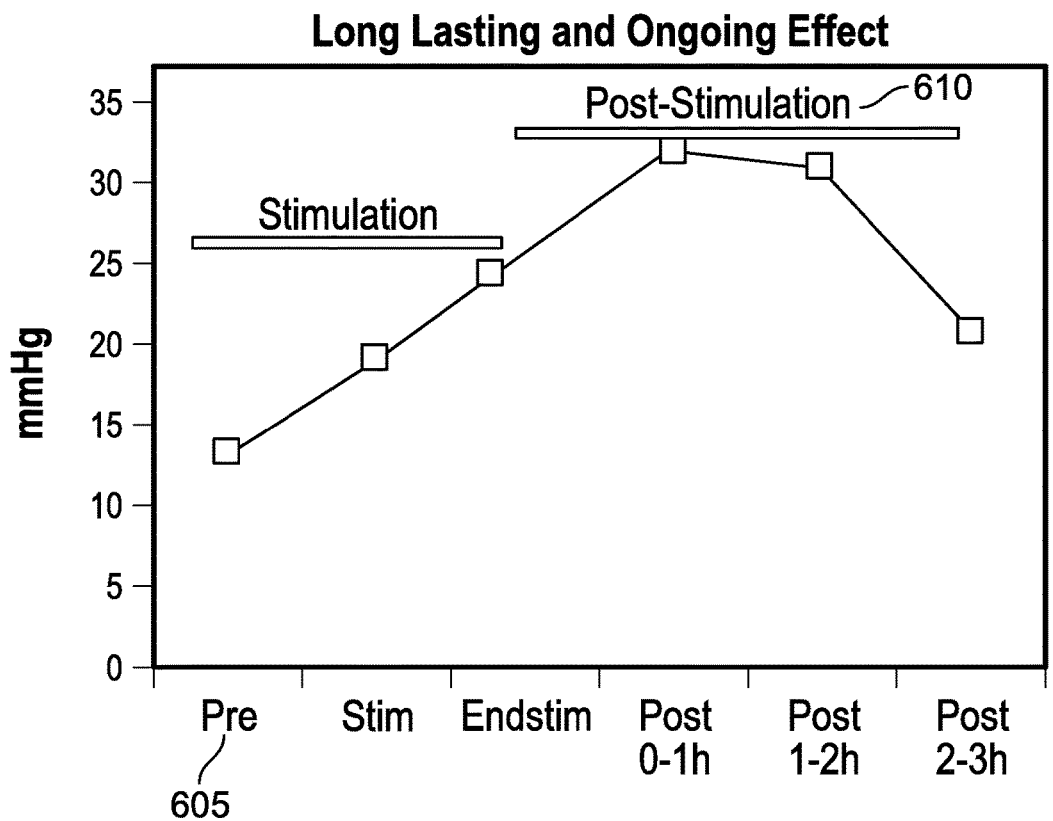
FIG. 6 is a graph depicting another exemplary pressure profile, both during stimulation and post-stimulation.

FIG. 3C is a flow chart illustrating the steps involved in one embodiment of a method of treating a patient with GERD by increasing the length of the LES high pressure zone through electrical stimulation. At step 302, a physician implants at least one stimulating electrode of an electrical stimulation system in accordance with various embodiments of the present specification proximate the LES of a patient. The system is then activated at step 304 to provide electrical stimulation to the LES. Optionally, in one embodiment, a plurality of sensors positioned in the esophagus detects an increase in the length of the LES high pressure zone at step 306. Optionally, at step 308, the system parameters are modified to provide an appropriate amount of stimulation to maintain the increase in length of the LES high pressure zone for a desire period of time in accordance with various treatment protocols of the present specification.

Figure 7:
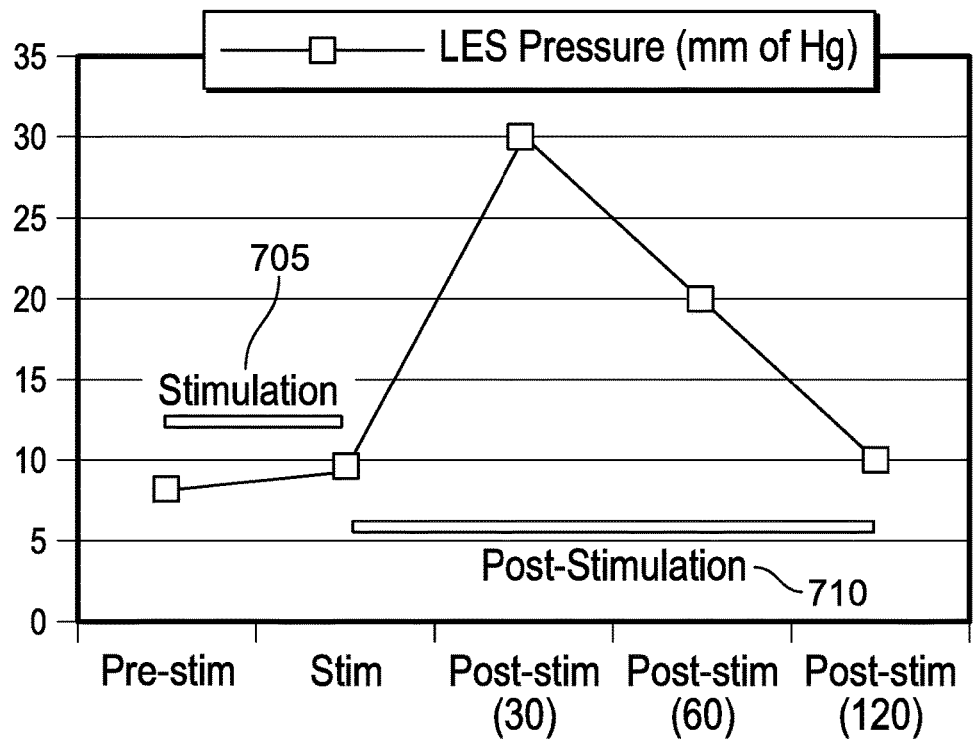
FIG. 7 is a graph depicting yet another exemplary pressure profile, both during stimulation and post-stimulation.

Referring to FIGS. 4-7, the presently disclosed methods and systems enable different post-stimulation residual effects, including an increase in LES pressure post-stimulation 410 followed by a decrease in LES pressure down to a stimulation state 405 over a period of 2 to 3 hours (FIG. 4), a slow decrease in LES pressure post-stimulation 510 back to a pre-stimulation LES pressure level 505 over a period of 1 to 2 hours (FIG. 5), a continued increase in LES pressure post-stimulation 610 followed by a decrease in LES pressure which still remains above a pre-stimulation state 605 after a period of 2 to 3 hours (FIG. 6), and minimal to no increase in LES pressure during stimulation 705 and a continued increase in LES pressure post-stimulation 710 followed by a decrease in LES pressure which still remains above a pre-stimulation state after a period of 2 to 3 hours (FIG. 7).

In one embodiment, the present specification encompasses a method for controlling muscle action using electrical stimulation by a modulated electrical signal having carrier frequency in the range of 2 KHz-100 KHz and an on-off modulating signal having an "on" duration in the range of 5 µs to 500 msec and, in particular, 200 µs.

In one embodiment, a pacemaker lead, such as a modified Medtronic 6416 200 cm, is secured to the LES in a submucosal tunnel using endoclips along the body of the lead and exteriorized nasally. Stimulation is applied using a 200 µsec to 3 msec pulse with a pulse amplitude of 1 mAmp to 15 mAmp, more preferably 5 mAmp to 10 mAmp, pulse frequency of preferably less than 1 msec, more preferably 200 µs, and a pulse width of 200 µsec. In various embodiments, the length of the patient's LES high pressure zone is increased by at least 5%, and more preferably by at least 10%. In various embodiments, gastric pressure is decreased by at least 5%, and more preferably by at least 10%. Additionally, in various embodiments, transient LES relaxation is improved by at least 5%, LES function is improved by at least 5%, esophageal body pressure is improved by at least 5%, esophageal body function is improved by at least 5%, symptoms of GERD are improved by at least 5%, esophageal acid exposure is improved by at least 5%, quality of life is improved by at least 5%, caloric intake is improved by at least 5%, and/or weight is improved by at least 5%.

These improvements are achieved without any affect on patient's swallow function, adverse symptoms, or cardiac rhythm disturbances. These improvements are also achieved by avoiding continuous electrical stimulation, which yields problems of muscle fatigue, build up of tolerance, tissue damage, and excessively high requirements for local energy storage, such as capacitor size or battery life.

In another embodiment, the stimulator may be operated using a pulse having a frequency of 20 Hz (1-100 Hz), a pulse amplitude of 1 µAmp-1 Amp, more preferably 1-20 mAmp, and a pulse width of 1 µsec-1 msec, and more preferably 100-500 µsec. The stimulator may also be stimulated using a pulse having a frequency of 20 Hz (1-100 Hz), a pulse amplitude of 1-20 mA (1 µAmp-1 Amp), and a pulse width of 1-50 msec (500 µsec-100 msec). The stimulator may also be stimulated using a pulse having a frequency of 5 cpm (1-100 cpm), a pulse amplitude of 1-20 mAmp (1 µAmp-1 Amp), and a pulse width of 100-500 msec (1 msec-1 sec).

In certain applications, there is an advantage to combining neural stimulation with direct muscle stimulation. Such applications include, for example, gastric stimulation for gastroparesis where a combined effect on gastric muscle and neural modulation can be synergistic in improving both gastric emptying rates and symptoms associated with gastroparesis. Another example can be the treatment of chronic reflux disease where both high frequency and low frequency pulses can have desirable effects on maintaining adequate lower esophageal sphincter tone or function while modulating the perception of symptoms associated with GERD.

In certain applications where an implantable electrode or a leadless device is used for delivering electrical stimulation, it is technically more feasible to apply lower pulse width (having higher frequency components) than signals having wider pulse duration. The reason is that irreversible electrochemical effects occur when the total charge transfer through the electrode-tissue interface at any given time increases above a certain threshold. In these cases, electrolysis occurs which releases metal ions into the tissue, damages the electrode, and causes dangerous pH changes in the local tissue. This has negative effects on the electrode longevity and on the tissue and should be avoided especially in chronic applications where stimulation of the same site using the same electrode or device is planned for an extended period of time.

Some methods for overcoming the problems of using long pulse durations were developed that attempt to enhance the capacitance of the electrode-tissue interface so as to increase the threshold for irreversible effects, thereby increasing the maximal pulse width that can be used chronically. Electrode capacitance can be increased in various ways, such as by enhancing effective electrode surface area by coating (e.g. coating with iridium-oxide or titanium nitride), by changing the electrode material, and/or by geometrical changes in the electrode shape. These methods, however, have some undesirable consequences, such as a significant increase in the manufacturing cost of the electrode and/or making the electrode unsuitable for specific implantation procedures. It is therefore useful to minimize the use of long pulse durations.

Furthermore, it should be noted that the use of square wave pulses, which is very common in conventional electrical stimulation systems, contains energy in frequency bands that are higher than the base rate of the pulse width. In general, when a square wave is used then most of the energy is delivered in the base rate and a portion of the energy is delivered in frequencies that are multiples (harmonics) of such base rate. Consequently, when a wide pulse width is delivered at a low frequency rate, some energy is also delivered in higher bands (multiples of the base rate) and also multiples of the reciprocal value of the pulse width. The practical effect, however, of these higher frequency components (or harmonics) is relatively small since only a small portion of the energy is delivered in these bands. It should further be appreciated that some frequencies, especially very high ones, are not absorbed in most tissues and can therefore be used as carriers to lower frequency signals that modulate them. Accordingly, high frequencies can be used to transfer or carry energy to the tissue without any physiological effect. Recovery of the low frequency signal is performed using a demodulator.

In light of the above, in one embodiment, a combination of low and high frequency signals (e.g. a waveform including both a high frequency component and a low frequency component) are delivered through an electrode or a leadless stimulating device with the purpose of applying two separate effects to the stimulated tissue and positively impacting LES high pressure zone length and functional LES pressure. The low frequency signal will be modulated on a high frequency carrier known to be neutral to muscle tone whereas the low frequency signal will be demodulated by the tissue itself and deliver a separate impact on the tissue, which is known to occur with a direct muscle stimulation using low frequency signals. The signal is designed to have a zero net charge delivered to the tissue over durations shorter than 1 ms thereby allowing flexibility in electrode design far more than what would be required if using a long pulse duration directly.

Figure 8:
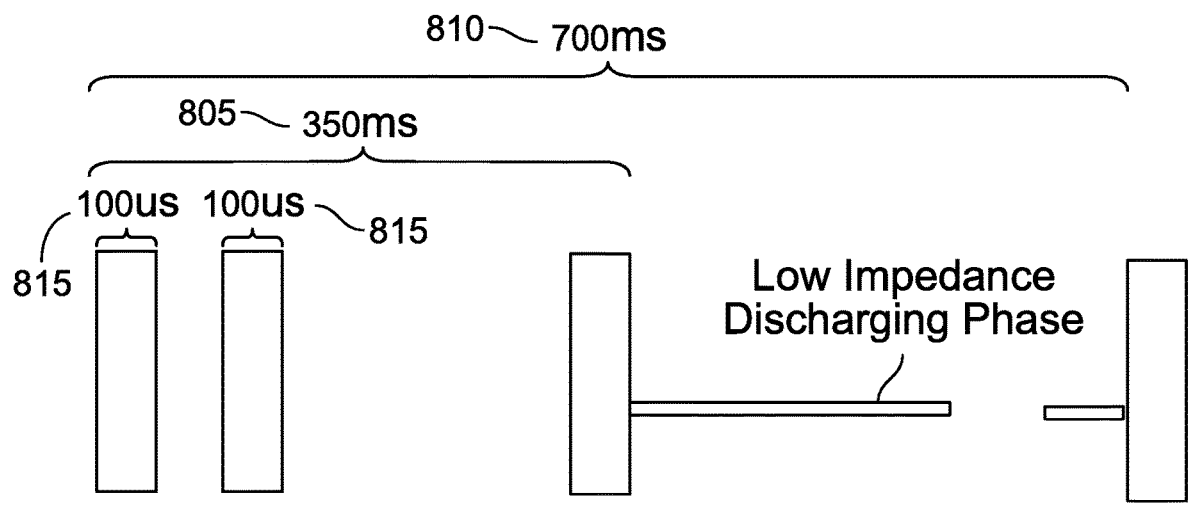
FIG. 8 is a schematic of modulated pulse trains in accordance with one embodiment of the present specification.

In one embodiment, referring to FIG. 8, the modulation is achieved by pulse trains having a base high frequency and duration equal to the desired long pulse width. Here, the stimulation train does not have a net zero charge; therefore, in order to discharge the electrode-tissue capacitance, a 350 msec time period 805 can be deployed, using a low impedance pathway switched by the stimulation device. Alternatively, a single negative discharging pulse can be applied once every 700 msec cycle 810. The low impedance connection can also preferably be applied following each of the 100 µsec pulses 815 thereby minimizing the maximal net charge accumulated on the electrode-tissue capacitance. There are several advantages of this waveform configuration: 1) the longest pulse duration applied is 100 µsec thereby relaxing the demands on a chronically implantable electrode capacitance that would have been required for a 350 msec pulse duration; 2) a train duration of 350 msec adds a low frequency component which is known to have a direct positive effect on muscle tone; 3) there is a reduced energy requirement from the device, resulting from the lower total pulse durations; and 4) the total stimulation result is optimized by a combination of two different frequency bands, each controlling the muscle through an independent physiological mechanism.

In another embodiment, the present invention encompasses an apparatus comprising a housing, pulse generator capable of generating square waves in the frequency range of 2 KHz-100 KHz, conductive tissue interface, means for fixation of conductive tissue interface to muscle tissue, programmable control unit capable of delivering said pulse generator output to the tissue intermittently whereas each "on" duration can be programmable in the range of 5 µsec to 500 msec and an "off" duration programmable in the same or different range. Optionally, the muscle tissue is the LES, stomach, esophagus, or UES. Optionally, the carrier frequency is in the range of 40 KHz-60 KHz and "on" duration is 300-400 msec. Optionally, the signal structure may be triggered by other timing mechanisms, including various patient-specific attributes, activities, and states. Optionally, a control unit, which is separate from a microstimulation device, includes a demodulator and a pulse generator for the high frequency carrier, transmits energy to the microstimulator to power the pulse generator, and includes modulation information using a different carrier frequency. Optionally, the stimulation device comprises multiple leads output and alternates a modulation signal between two or more stimulation locations where, while one location has an "on" state, the other location has an "off" state, and vice-versa.

In another embodiment, the stimulator may be stimulated using an "on" phase and an "off" phase, wherein the on phase is between 1 minute and 1 hour and the off phase is between 1 minute and 1 hour. Preferably, both the on and off phases are between 5 and 30 minutes. In another embodiment, the stimulator or microstimulator may be stimulated using a combination of a low frequency pulse and an intermediate or high frequency pulse. In one embodiment, the low frequency pulses are delivered for a duration that is 1% to 1000% of the intermediate or high pulse duration.

In another embodiment, the stimulator may be stimulated using an "on" phase and an "off" phase, wherein the on phase is between 1 second and 24 hours and the off phase is between 1 second and 24 hours. Preferably, the off phase is longer than the on phase. In this embodiment, the stimulator or microstimulator may be stimulated using a combination of a low frequency pulse and an intermediate or high frequency pulse. In one embodiment, the low frequency pulses are delivered for a duration that is 1% to 1000% of the intermediate or high pulse duration. In another embodiment a combination of same frequency pulse with varying amplitude can be used. For example, a patient can receive intermittent or continuous stimulation at a lower amplitude with one or more sessions of stimulation at a higher amplitude wherein the higher amplitude is at least twice the lower amplitude.

It should be appreciated that, wherever stimulation parameters are described, the stimulation may be initiated by "ramping up" to the stated stimulation levels or may be terminated by "ramping down" to an off state. The ramp up and ramp down can be as slow or as fast as required to effectuate the required therapy.

In one embodiment, the programmed duty cycle, pulse frequency, pulse width, pulse amplitude of the stimulator and corresponding electrode configuration are configured to trigger secretion of neurokinin A (NKA) or a similar peptide. The configuration of the frequency and amplitude is set to efficiently achieve a clinically significant secretion with minimal energy. The session duration can make use of the long degradation time of NKA and be configured to turn off stimulation following the expected accumulation of sufficient NKA secretion. Electrode configuration, as further described below, can be adapted so that the desired optimal session duration will alternate in different regions using implantation of electrodes in different regions of the LES. The configuration of the stimulation to impact local NKA level can be designed to achieve the required pressure curve as described in FIGS. 4-7.

It should further be noted that, because the stimulation device enables the therapeutically effective treatment of a plurality of ailments, as described above, at currents below 15 mAmp, one can avoid subjecting the patient to physical pain, sensation, or discomfort. The present system can achieve the therapeutic goals and effectively operate by delivering lower stimulation levels for longer periods of time, such as by delivering 3 mAmp for 10 minutes rather than 15 mAmp for 5 minutes. The pulse frequency can be 20 Hz and the stimulation can be delivered less than five times per day, such as three times per day.

In one embodiment, the presently disclosed systems and methods achieve any of the aforementioned therapeutic objectives by providing or implanting a stimulation device, such as a macrostimulator or microstimulator, adapted to be implanted within or proximate the patient's lower esophageal sphincter, esophagus, upper esophageal sphincter, stomach, gastric fundus, or gastric cardia and adapted to apply electrical stimulation to the patient's lower esophageal sphincter or gastric fundus; and programming, using, or operating said stimulation device, wherein said programming, use, or operation defines, uses, or is dependent upon a plurality of stimulation parameters that determine the application of electrical stimulation to the patient's lower esophageal sphincter or gastric fundus and wherein said stimulation parameters are selected, derived, obtained, calculated, or determined, at least in part, to account for a latent, delayed, time-delayed, or future response of the patient's lower esophageal sphincter or gastric fundus.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia and to apply electrical stimulation to the patient's lower esophageal sphincter or gastric fundus, wherein said lower esophageal sphincter or gastric fundus exhibits a latent, delayed, time-delayed, or future response to applied electrical stimulation; and treating said patient by applying electrical stimulation based upon derived from, or dependent upon said latent, delayed, time-delayed or future response.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia and to apply electrical stimulation to the patient's lower esophageal sphincter or gastric fundus; and initiating, activating, beginning, or starting said electrical stimulation prior to a pre-defined or fixed time wherein said pre-defined or fixed time is associated with a GERD triggering event and wherein said initiation occurs prior to said pre-defined or fixed time by a minimum period, such as at least 5 minutes, 10 minutes, 15 minutes, 30 minutes, 1 hour, 2 hours, 3 hours, 12 hours, 24 hours, or any time increment therein.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia and adapted to apply electrical stimulation to the patient's lower esophageal sphincter or gastric fundus; and initiating, activating, beginning, or starting said electrical stimulation prior to a pre-defined or fixed time wherein said pre-defined or fixed time is associated with a GERD triggering event and wherein said initiation occurs prior to said pre-defined or fixed time by a minimum period, such as at least 5 minutes, 10 minutes, 15 minutes, 30 minutes, 1 hour, 2 hours, 3 hours, 12 hours, 24 hours, or any time increment therein; and terminating said electrical stimulation after said pre-defined or fixed time has passed.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia and adapted to apply electrical stimulation to the patient's lower esophageal sphincter or gastric fundus; and programming, using, or operating said stimulation device, wherein said programming, use, or operation defines, uses, or is dependent upon a plurality of stimulation parameters that determine the application of electrical stimulation to the patient's lower esophageal sphincter or gastric fundus and wherein said stimulation parameters are selected, derived, obtained, calculated, or determined, at least in part, to treat GERD without inhibiting, hindering, stopping, or preventing the patient from swallowing.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia and treating said patient by applying electrical stimulation while the patient swallows, during periods of esophageal motility, or during esophageal peristalsis.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia and treating said patient by applying electrical stimulation in accordance with a preset period wherein said preset period is not dependent upon, influenced by, modified by, lengthened by, or shortened by a physiological state of a patient.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia and treating said patient by applying electrical stimulation in accordance with a preset period wherein said preset period is not dependent upon, influenced by, modified by, lengthened by, or shortened by the patient swallowing, esophageal motility, esophageal peristalsis, or being in a feeding state.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia and treating said patient by applying electrical stimulation that is not dependent upon, influenced by, modified by, lengthened by, or shortened by a physiological state, biological parameter, sensed physiological or biological parameters of a patient.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia and treating said patient by applying electrical stimulation that is not dependent upon, influenced by, modified by, lengthened by, or shortened by the patient swallowing, esophageal motility, esophageal peristalsis, or being in a feeding state.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, wherein said lower esophageal sphincter has a high pressure zone having a length and said stomach has a gastric pressure, and treating said patient by applying sufficient electrical stimulation to increase said length of said high pressure zone or decreasing said gastric pressure but not to inhibit, hinder, stop, or prevent swallowing, esophageal motility, esophageal peristalsis, or being in a feeding state.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, wherein the lower esophageal sphincter has a function, and treating the patient by applying sufficient electrical stimulation to improve said function but not to inhibit, hinder, stop, or prevent swallowing, esophageal motility, or esophageal peristalsis or dissuade a patient from being in a feeding state.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, wherein said lower esophageal sphincter has a pressure; and treating said patient by applying electrical stimulation, wherein said stimulation causes an increase in said pressure of at least 5% only after an elapsed period of time of at least one minute.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, wherein said lower esophageal sphincter has a high pressure zone having a length; and treating said patient by applying electrical stimulation, wherein said stimulation causes an increase in said length of said high pressure zone of at least 5%, and more preferably by at least 10% only after an elapsed period of time of at least one minute.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, wherein said patient has a stomach having a gastric pressure; and treating said patient by applying electrical stimulation, wherein said stimulation causes a decrease in said gastric pressure of at least 5%, and more preferably by at least 10% only after an elapsed period of time of at least one minute.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, wherein said lower esophageal sphincter has a high pressure zone having a length; and treating said patient by applying electrical stimulation, wherein said stimulation improves or normalizes lower esophageal function, or enhances or increases said length of said high pressure zone to a normal physiological range only after an elapsed period of time or only after a delay of at least one minute.

In one embodiment, the presently disclosed systems and methods achieve any of the aforementioned therapeutic objectives by providing or implanting a stimulation device adapted to be implanted within or proximate the patient's gastric fundus, esophagus, upper esophageal sphincter, stomach, gastric fundus, or gastric cardia, wherein stomach has a gastric pressure; and treating said patient by applying electrical stimulation, wherein said stimulation improves or normalizes lower esophageal function or decreases said gastric pressure below a normal physiological range only after an elapsed period of time or only after a delay of at least one minute.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, wherein said lower esophageal sphincter has a high pressure zone having a length and said stomach has a gastric pressure; and treating said patient by applying electrical stimulation, wherein said stimulation causes a non-instantaneous or delayed increase in said length of said high pressure zone or a decrease in said gastric pressure.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, wherein the lower esophageal sphincter has a function, and treating the patient by applying electrical stimulation, wherein the stimulation causes a non-instantaneous or delayed improvement in the function.

In one embodiment, the presently disclosed methods and devices achieve any of the aforementioned therapeutic objectives by providing or implanting a stimulation device adapted to be implanted within the patient's lower esophageal sphincter, esophagus, upper esophageal sphincter, stomach, gastric fundus, or gastric cardia, wherein said lower esophageal sphincter has a pressure; and treating said patient by applying electrical stimulation, wherein said stimulation causes a non-instantaneous or delayed increase in said pressure and wherein said non-instantaneous or delayed increase in the pressure normalizes LES function, normalizes LES pressure, increases LES pressure to a normal physiological range, or increases LES pressure by at least 3%.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, wherein said lower esophageal sphincter has a high pressure zone having a length; and treating said patient by applying electrical stimulation, wherein said stimulation causes a non-instantaneous or delayed increase in said length of said high pressure zone and wherein said non-instantaneous or delayed increase said length of said high pressure zone normalizes LES function, normalizes LES pressure, increases LES pressure to a normal physiological range, or increases LES pressure by at least 3%.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, wherein said stomach has a gastric pressure; and treating said patient by applying electrical stimulation, wherein said stimulation causes a non-instantaneous or delayed decrease is said gastric pressure and wherein said non-instantaneous or delayed decrease in gastric pressure normalizes LES function, normalizes functional LES pressure, increases functional LES pressure to a normal physiological range, or increases functional LES pressure by at least 3%.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, wherein said lower esophageal sphincter has a high pressure zone having a length and said stomach has a gastric pressure; and treating said patient by applying electrical stimulation, wherein said stimulation causes a gradual increase in said length of said high pressure zone or a gradual decrease in said gastric pressure.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, wherein said lower esophageal sphincter has a high pressure zone having a length and said stomach has a gastric pressure; and treating said patient by applying electrical stimulation, wherein said stimulation causes an increase in said length of said high pressure zone or a decrease in said gastric pressure after said electrical stimulation is terminated.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, wherein said lower esophageal sphincter has a high pressure zone having a length and said stomach has a gastric pressure; and treating said patient by applying electrical stimulation having a first level, wherein said stimulation causes an increase in said length of said high pressure zone or a decrease in said gastric pressure after said electrical stimulation is decreased from said first level.

In one embodiment, the presently disclosed systems and methods achieve any of the aforementioned therapeutic objectives by enhancing the length of the high pressure zone, decreasing gastric pressure, or improving the function of the patient's lower esophageal sphincter.

In one embodiment, the presently disclosed systems and methods achieve any of the aforementioned therapeutic objectives, wherein said patient has a lower esophageal sphincter and a stomach and wherein said lower esophageal sphincter has a high pressure zone having a length and said stomach has a gastric pressure, by increasing the length of the high pressure zone of the patient's lower esophageal sphincter or decreasing said gastric pressure through the application of electrical stimulation to the lower esophageal sphincter, esophagus, upper esophageal sphincter, stomach, gastric fundus, or gastric cardia, or areas proximate thereto.

In one embodiment, the presently disclosed systems and methods achieve any of the aforementioned therapeutic objectives, wherein said patient has a lower esophageal sphincter and a stomach and wherein said lower esophageal sphincter has a high pressure zone having a length and said stomach has a gastric pressure, by increasing the length of said high pressure zone of the patient's lower esophageal sphincter or decreasing said pressure through the application of electrical stimulation to the lower esophageal sphincter, esophagus, upper esophageal sphincter, stomach, gastric fundus, or gastric cardia or areas proximate thereto, and wherein said increase in length of said high pressure zone or said decrease in pressure does not inhibit or otherwise hinder the patient's ability to swallow.

In one embodiment, the presently disclosed systems and methods achieve any of the aforementioned therapeutic objectives by modifying the pressure or function of the patient's lower esophageal sphincter.

In one embodiment, the presently disclosed systems and methods achieve any of the aforementioned therapeutic objectives by modifying the pressure or function of the patient's lower esophageal sphincter through the application of electrical stimulation to the lower esophageal sphincter or areas proximate thereto.

In one embodiment, the presently disclosed systems and methods achieve any of the aforementioned therapeutic objectives by enhancing the length of the high pressure zone, decreasing gastric pressure, or modifying the function of the patient's lower esophageal sphincter through the application of electrical stimulation to the lower esophageal sphincter, esophagus, upper esophageal sphincter, stomach, gastric fundus, or gastric cardia, or areas proximate thereto.

In one embodiment, the presently disclosed systems and methods achieve any of the aforementioned therapeutic objectives by enhancing the length of the high pressure zone, decreasing gastric pressure, or modifying the function of the patient's lower esophageal sphincter through the application of electrical stimulation to the lower esophageal sphincter, esophagus, upper esophageal sphincter, stomach, gastric fundus, or gastric cardia, or areas proximate thereto and wherein said increase in length of said high pressure zone or said decrease in gastric pressure does not inhibit or otherwise hinder the patient's ability to swallow.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, and treating said patient by applying electrical stimulation in accordance with at least one "on" period, wherein said "on" period is between 1 second and 24 hours and is not triggered by, substantially concurrent to, or substantially simultaneous with an incidence of acid reflux, and at least one "off" period, wherein said "off" period is greater than 1 second.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, and treating said patient by applying electrical stimulation, wherein a pulse amplitude from a single electrode pair ranges from greater than or equal to 1 mAmp to less than or equal to 8 mAmp.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, and treating said patient by applying electrical stimulation having a pulse duration of approximately 200 μsec.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, and treating said patient by applying electrical stimulation having a pulse duration of approximately 1 msec.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, and treating said patient by applying electrical stimulation having a pulse energy level of <10 mAmp, pulse duration of <1 second, and/or pulse frequency of <50 Hz.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, and treating said patient by applying electrical stimulation having a pulse energy level of 1 mAmp to 10 mAmp (preferably 1 mAmp), pulse duration in a range of 50 μsec to 1 msec (preferably 215 μsec), a pulse frequency of 5 Hz to 50 Hz (preferably 20 Hz), pulse on time in a range of 10 minutes to 120 minutes (preferably 30 minutes), and/or pulse off time in a range of 10 minutes to 24 hours. In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, and treating said patient by applying electrical stimulation to increase LES pressure above a baseline or threshold LES pressure, wherein said LES pressure remains above said baseline or threshold LES pressure after termination of electrical stimulation.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, and treating said patient by applying electrical stimulation to increase the length of the LES high pressure zone above a baseline or threshold high pressure zone length, wherein said length of said LES high pressure zone remains above said baseline or threshold high pressure zone length after termination of electrical stimulation.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, and treating said patient by applying electrical stimulation to decrease gastric pressure below a baseline or threshold pressure level, wherein said gastric pressure remains below said baseline or threshold pressure level after termination of electrical stimulation.

In one embodiment, the presently disclosed systems and methods achieve any of the aforementioned therapeutic objectives by providing or implanting a stimulation device adapted to be implanted within or proximate the patient's lower esophageal sphincter, esophagus, upper esophageal sphincter, stomach, gastric fundus, or gastric cardia, and treating said patient by applying electrical stimulation to increase LES tone above a threshold LES tone, wherein said LES tone remains above said threshold LES tone after termination of electrical stimulation.

In one embodiment, the presently disclosed systems and methods achieve any of the aforementioned therapeutic objectives by providing or implanting a stimulation device adapted to be implanted within or proximate the patient's gastric fundus, esophagus, upper esophageal sphincter, stomach, gastric fundus, or gastric cardia, and treating said patient by applying electrical stimulation to decrease fundus tone below a threshold fundus tone, wherein said fundus tone remains below said threshold fundus tone after termination of electrical stimulation.

In one embodiment, the presently disclosed systems and methods provide a macrostimulator programmed, adapted to, or configured to perform any of the aforementioned methods or treatment protocols.

In one embodiment, the presently disclosed system and methods provide a macrostimulator comprising at least one electrode, an energy source, and a pulse generator in electrical communication with the at least one electrode and energy source, wherein said pulse generator is programmed, adapted to, or configured to perform any of the aforementioned methods or treatment protocols.

In one embodiment, the presently disclosed systems and methods provide a microstimulator programmed, adapted to, or configured to perform any of the aforementioned methods or treatment protocols.

In one embodiment, the presently disclosed systems and methods provide a microstimulator comprising at least one electrode, an energy source, and a pulse generator in electrical communication with the at least one electrode and energy source, wherein said pulse generator is programmed, adapted to, or configured to perform any of the aforementioned methods or treatment protocols.

Such treatment methods may be combined, directed toward any of the aforementioned therapeutic objectives, and/or implemented through stimulating any of the aforementioned anatomical areas. The treatment methods may be further modified by using specific stimulation parameters, open loop data processes, closed loop data processes, the patient's physical position and degree of activity, the patient's eating state, timing, quantity or content thereof, certain physiological parameters sensed by the device, including LES pressure, gastric pressure, or anti-habituation methods to prevent anatomical habituation to a specific set of stimulation parameters. Additionally, because the device can operate on a time-based schedule and not necessarily on physiological triggers (although a physiological trigger can be an optional embodiment), stimulation schedules can be tailored to user behavior and/or routine. For example, stimulation therapy can be delivered or stimulation energy can be transmitted at times that are most convenient and least disruptive to the patient's activities of daily living, such as only scheduling stimulation while the patient is sleeping, relaxing, or watching TV and scheduling stimulation only after mealtimes. Such additional embodiments are described below.

Open Loop Programming

In one optional embodiment, the stimulation parameters, including pulse width, pulse frequency, pulse amplitude, ramp rates, and/or duty cycle, can be modified by a physician using data sensed by, stored within, or transmitted from the stimulation device, data sensed by, stored within, or transmitted from a sensor implanted in the patient, and/or data captured by an external computing device used by a patient. A stimulator device having a local memory, or a transmitter capable of communicating sensed information to a remotely located memory or memory external to the patient, captures a plurality of sensed data, as discussed in greater detail below. Concurrently, a patient controlled computing device, such as a laptop, personal computer, mobile device, or tablet computer, which is external to the patient is used by the patient to store data input by the patient relevant to evaluating, monitoring, and adjusting the operation of the stimulator. Both the stimulator captured data and patient inputted data is then transmitted to a physician controlled device, as described below, to enable the physician to properly evaluate, monitor, and modify the stimulation parameters.

In one embodiment, the patient-controlled computing device comprises a plurality of programmatic instructions that, when executed, generate a display which prompts a user for, and is capable of receiving input from the user, information regarding the user's food intake, the timing of such food intake, exercise regimen, degree and extent of physical symptoms, incidents of acid reflux, when the user sleeps, when the user lays down, type of food being consumed, quantity of food, among other variables. This data can be captured and stored locally and/or transmitted to a remote server for access by a physician. If accessed remotely by a physician, the physician can transmit alerts back to the patient, via a network in communication with the computing device or conventional communication systems, such as email, text messaging or phone, to confirm dose amounts, patient state information, or provide for therapy adjustment.

In one embodiment, the stimulator captured data includes what stimulation parameters were used and when, the sensed LES pressure profile within the high pressure zone, including the percentage or amount of time the LES high pressure zone was lengthened beyond a certain threshold level, such as greater than 10%, or beyond a $2^{nd}$ threshold level, such as greater than 20%, the occurrence of t-LESRs, esophageal pH, supine events, degree of physical movement, among other variables.

In another embodiment, the stimulator captured data includes what stimulation parameters were used and when, the sensed gastric pressure profile, including the percentage or amount of time the gastric pressure was decreased beyond a certain threshold level, such as greater than 10%, or beyond a $2^{nd}$ threshold level, such as greater than 20%, the occurrence of t-LESRs, esophageal pH, supine events, degree of physical movement, among other variables.

The patient-inputted data, when combined with the stimulator captured data, can provide a holistic view of the patient's condition and the efficacy of a stimulation regimen. In particular, as patient symptoms are mapped to stimulation parameters and analyzed in relation to food or drink intake, sleep, and exercise regimens, a physician will be able to determine how best to modify the stimulation parameters, including duty cycle, stimulation initiation times or triggers, stimulation termination times or triggers, pulse width, pulse amplitude, duty cycle, ramp rates, or pulse frequency, to improve patient treatment. As further discussed below, the physician will receive both the patient-captured and stimulation device captured data into a diagnostic terminal that can be used to process the information and transmit new stimulation parameters, if necessary, to the stimulation device. For example, the physician can modify the stimulation parameters in a manner that would lower the incidents of reported acid reflux, generalized pain, pain while swallowing, generalized discomfort, discomfort while swallowing, or lack of comfort during sleeping or physical exercise. The physician can also modify the stimulation parameters, including the initiation and termination of stimulation, to better match one or more GERD triggering events, such as eating, sleeping, lying down, or engaging in physical activity. The physician can also modify the stimulation parameters, including the initiation and termination of stimulation, to better match the patient's personal work or vacation schedule.

Additionally, alerts can be created that can be either programmed into the patient-controlled device or stimulation device which serve to notify the patient of a device malfunction, a recommendation to take a drug, a recommendation to come back for a checkup, among other variables. Those alerts can also be transmitted, via a computing network, to the physician. Furthermore, external data sources, such as demographic data or expert protocols, can be integrated into the physician system to help the physician improve the diagnostic and evaluation process and optimize the programmed set of stimulation parameters.

It should further be appreciated that, as the patient controlled device and stimulator device accumulate data that maps the therapeutic regimen against the patient's activities and symptoms, the patient controlled device will be able to determine, and therefore inform the patient of, patterns which tend to increase or decrease the incidents of GERD, including types of food, quantity of food, timing of eating, among other variables.

Closed Loop Programming

In one optional embodiment, the stimulation parameters, including pulse width, pulse frequency, pulse amplitude, initiation of stimulation, triggers for stimulation, termination of stimulation, triggers to terminate stimulation, ramp rates, and/or duty cycle, can be dynamically and intelligently modified by the stimulation device using data sensed by, stored within, or transmitted from the stimulation device, data sensed by, stored within, or transmitted from a sensor implanted in the patient, and/or data captured by, stored within, and/or transmitted from an external computing device used by a patient.

As discussed above, data maybe captured by a patient-controlled device and/or the stimulator device. In this embodiment, a stimulator is further programmed to intelligently modify stimulation parameters, without physician input, based upon sensed data and/or patient inputs. In various embodiments, a stimulator determines that the length of the LES high pressure zone fails to increase, gastric pressure fails to decrease, or LES function fails to improve above a predefined threshold, even after a predefined amount of stimulation, and, accordingly, automatically modifies the stimulation parameters, within a preset range of operation, to yield an improvement in LES high pressure zone increase or gastric pressure decrease. In one embodiment, a stimulator determines that the length of the LES high pressure zone, gastric pressure decrease, or LES function improves significantly above a predefined threshold, after a predefined amount of stimulation, or maintains a level above a predefined threshold and, accordingly, automatically modifies the stimulation parameters, within a preset range of operation, to yield an improvement in LES high pressure zone length, gastric pressure decrease, or LES function.

In one embodiment, a stimulator determines the length of the LES high pressure zone or decrease in gastric pressure remains above a predefined threshold level for a sufficient amount of time such that a subsequent pre-programmed stimulation session or sessions can be postponed or cancelled. In one embodiment, a stimulator device monitors the length of the LES high pressure zone or gastric pressure and initiates stimulation only when said length falls below a predetermined threshold or said gastric pressure increases above a predetermined threshold. Preprogrammed stimulation may be modified in order to continue or increase in energy, duration, or frequency until the length of the LES high pressure zone rises above a predetermined threshold or gastric pressure decreases below a predetermined threshold. The length of the LES high pressure zone and/or gastric pressure threshold may be dynamically modified based upon sensed data.

In one embodiment, a stimulator determines that esophageal pH is indicative of incidents of acid reflux above a predefined threshold level, and, accordingly, automatically modifies the stimulation parameters, within a preset range of operation, to yield an improvement in the length of the LES high pressure zone increase or gastric pressure reduction to lower such incidents. In one embodiment, a stimulator receives a communication from an external patient controlled device indicating that the patient is reporting a number of adverse incidents above a predefined threshold, such as acid reflux, generalized pain, pain while swallowing, generalized discomfort, discomfort while swallowing, lack of comfort when sleeping, etc. and, accordingly, automatically modifies the stimulation parameters, within a preset range of operation, to yield a lower level of such incidents. In one embodiment, a stimulator receives a communication from an external patient controlled device detailing a schedule of potentially GERD triggering events, including sleep times, eating times, or exercise times, and, accordingly, automatically modifies the stimulation parameters, within a preset range of operation, to properly account for such GERD triggering events.

In one embodiment, the stimulator operates using both open loop and closed loop programming. Stimulation parameters may be established using open loop programming methods, as described above, and then modified through the aforementioned closed loop programming methods. Stimulation parameters may also be established using closed loop programming methods, as described above, and then modified through the aforementioned open loop programming methods.

Stimulation Modification Based on Sensed Data

It should be appreciated that the stimulation system may stimulate based on a plurality of data, including based on the length of the LES high pressure zone registering below a predefined threshold, based on gastric pressure registering above a predefined threshold, based on a patient's pH level, based on the patient's physical orientation, based on the patient's meal intake, or based on a predefined time period, among other triggers. It should also be appreciated that the controller may initiate or stop a stimulation based on a plurality of triggers, including based on the length of the LES high pressure zone exceeding a predefined threshold, based on gastric pressure decreasing below a predefined threshold, based on a patient's pH level, based on the patient's physical orientation, or based on a predefined time period, among other triggers.

Using various data sensors, including, but not limited to impedance, electrical activity, piezoelectric, pH, accelerometer, inclinometer, ultrasound-based sensors, RF-based sensors, or strain gauge, the system can determine whether a patient is eating, how much the patient is eating, how long the patient is eating, and/or what the patient is eating, and, based on that information, adjust stimulation parameters accordingly. In particular, pH data may be used to determine what kind of food a patient is eating, where the type of food is defined in terms of its acidity.

In one embodiment, the stimulator system senses the length of the LES high pressure zone and initiates stimulation of the LES when said length is below a pre-defined threshold level for a predefined period of time and terminates stimulation of the LES when said length is above a pre-defined threshold level for a predefined period of time. The length of the LES high pressure zone may be determined by sensing and processing impedance measurements, electrical activity measurements, strain gauge, and/or piezoelectric measurements. One or more of the various measurements are constantly measured to create a contiguous high pressure zone length profile. Based upon the length profile, the stimulator can modify stimulation parameters, including pulse amplitude, pulse width, duty cycle, pulse frequency, stimulation initiation time, ramp rate, or stimulation termination time, to achieve, with respect to said length, an absolute amount of change, a percentage amount of change, increases or decreases above or below a threshold value, increases or decreases based on time, increases or decreases based on a length slope, among other measures of change.

In another embodiment, the stimulator system senses gastric pressure and initiates stimulation of the gastric fundus when said gastric pressure is above a pre-defined threshold level for a predefined period of time and terminates stimulation of the fundus when said gastric pressure is below a pre-defined threshold level for a predefined period of time. Gastric pressure may be determined by sensing and processing impedance measurements, electrical activity measurements, strain gauge, and/or piezoelectric measurements. One or more of the various measurements are constantly measured to create a contiguous gastric pressure profile. Based upon the pressure profile, the stimulator can modify stimulation parameters, including pulse amplitude, pulse width, duty cycle, pulse frequency, stimulation initiation time, ramp rate, or stimulation termination time, to achieve, with respect to said pressure, an absolute amount of change, a percentage amount of change, increases or decreases above or below a threshold value, increases or decreases based on time, increases or decreases based on a length slope, among other measures of change.

In another embodiment, the stimulator system uses various data sensors to determine the pulmonary, intra-thoracic, or intra-abdominal pressure and, based on pulmonary, intra-thoracic, or intra-abdominal pressure, create a patient-specific dose, such as a specific pulse amplitude, pulse width, duty cycle, pulse frequency, stimulation initiation time, ramp rate, or stimulation termination time, required to affect LES tone, pressure, or function to the levels needed by that patient.

In another embodiment, the stimulator system uses various data sensors to determine the esophageal temperature and, based on that temperature reading, create a patient-specific dose, such as a specific pulse amplitude, pulse width, duty cycle, pulse frequency, stimulation initiation time, ramp rate, or stimulation termination time.

In another embodiment, the stimulator system uses various data sensors to determine the esophageal pH and, based on that pH reading, create a patient-specific dose, such as a specific pulse amplitude, pulse width, duty cycle, pulse frequency, stimulation initiation time, ramp rate, or stimulation termination time.

In another embodiment, the stimulator system uses a combination of data inputs from the above described sensors to generate a total score from which a stimulation therapeutic regimen is derived. For example, if the patient has not eaten for a long time and lays down, a lower (or no) therapy dose would be delivered. Since GERD is an episodic disease and certain periods are more vulnerable to a reflux event than others, detecting various patient parameters by various means and using them in an algorithm enables clinicians to target those specific reflux events. In addition, in various embodiments, multiple algorithms are programmed into the stimulator device so that treatment can be tailored to various types of GERD, based upon input relayed by the sensors. In one embodiment, data from any combination of one or more of the following parameters is used by an algorithm to determine stimulation protocol: patient feed state including type of intake (via patient input or eating detection by a physical sensor that can detect and/or evaluate liquids/solids/caloric value); patient position (via inclinometer/accelerometer); patient activity (via accelerometer/actimeter); patient reflux profile (via patient input/pH recording); the length of the LES high pressure zone; LES pressure; LES electrical activity; LES mechanical activity (via accelerometer in the LES, pressure sensor, impedance measure or change thereof); gastric pressure; gastric electrical activity; gastric chemical activity; gastric temperature; gastric mechanical activity (via an accelerometer in the stomach, pressure sensor, impedance measurement and changes); patient intuition; vagal neural activity; and, splanchnic neural activity. Based on input from one or more of the above parameters, the algorithm quantifies the vulnerability for a reflux event and modifies accordingly the amplitude, frequency, pulse-width, duty cycle, ramp rate, and timing of stimulation treatment. The table below lists the parameters, measurements, and values used in an exemplary treatment protocol of one embodiment of the present invention.

TABLE 3

| Parameter | Measurement | Value |
| --- | --- | --- |
| Length of LES High Pressure Zone | Normal | 0 |
| | Low | 1 |
| Gastric Pressure | Low | 0 |
| | Normal | 1 |
| LES Pressure | Normal | 0 |
| | Low | 1 |
| Inclination | Upright | 0 |
| | Supine | 1 |
| Feed State | Fasting/Pre-prandial | 0 |
| | Post-prandial | 1 |
| Time of the day | Day time | 1 |
| | Night time | 0 |
| Fat content of meal | Low | 0 |
| | High | 1 |
| Patient pH Profile | Low-risk period | 0 |
| | High-risk period | 1 |
| Patient Symptom Input | Low-risk period | 0 |
| | High-risk period | 1 |
| Gastric Activity | Food Absent | 0 |
| | Food Present | 1 |
| Upright Activity Level | Low | 0 |
| | High | 1 |
| Supine Activity Level | High | 1 |
| | Low | 0 |
| Patient Intuition | Low Likelihood | 0 |
| | High Likelihood | 1 |

In the table above, each individual parameter is given a score of 1 or 0 depending on the value measured. In one embodiment, a summary score is tabulated using one or more parameters in the above exemplary algorithm scoring system to determine patient vulnerability to a reflux event. Based on the score, the treatment parameter is modified. Patients with a higher summary score are indicated for a greater level of treatment. For example, a patient with normal LES pressure in the upright position and a pre-prandial state will be at minimal risk for a reflux event and no therapy will be indicated. Conversely, a patient with low LES pressure in the upright position and an immediate post-prandial state will be at the highest risk for a reflux event and would receive the highest level of GERD therapy. A patient with a low, or short, length of the LES high pressure zone would be at high risk for a reflux event and would receive a high level of GERD therapy.

In one embodiment, a measured parameter is used as a modifier for another parameter. For example, gastric activity showing food absent does not have an individual score but modifies the feed state score from a post-prandial score to a fasting/pre-prandial score. In another embodiment, a measured parameter has an absolute value that is not impacted by other measured parameters. For example, patient intuition of a high likelihood of a reflux event is an absolute parameter that delivers the highest level of GERD therapy irrespective of other sensed parameters.

In one embodiment, the scoring system for certain individual parameters is a scale rather than a binary score. For example, in one embodiment, the score given to LES pressure is within a range from 0-5 based on duration of low pressure. With each incremental 5 minute duration of low LES pressure, the score increases by one increment. In another embodiment, the score given to gastric pressure is within a range from 0-5 based on duration of low pressure. With each incremental 5 minute duration of normal or high gastric pressure, the score increases by one increment.

In another embodiment, different weight is given to different parameters. For example, in one embodiment, low LES pressure is given an absolute score higher than post-prandial feed state.

In another embodiment, the scoring system is tailored to be patient specific. In one embodiment, for example, for a patient with low symptom predictability as ascertained by symptom association with a standard pH test, patient symptom input is given a lower weight. In another embodiment, for a patient with mostly upright reflux on pH testing, the upright position is given a greater weight than the supine position. In yet another embodiment, for a patient with exercise induced reflux, a greater weight is given to upright activity while the same parameter receives a low weight or is eliminated from the algorithm in a patient without exercise induced reflux.

Accelerometer/Inclinometer Based Stimulation System

In one embodiment, the implantable device includes an accelerometer or inclinometer and a pre-programmed supine stimulation mode intended to automatically provide the patient with additional stimulation sessions during extended time periods in which the patient is in the supine position, as noted by said accelerometer/inclinometer. When the mode is enabled by a programmer, a supine position detection triggers additional stimulation sessions based on pre-set programmable conditions. In one embodiment, additional stimulation sessions will be initiated automatically when the following two conditions are met: 1) the patient is supine (based on a programmable range of inclination) for a minimum amount of time (based on pre-set time ranges) and 2) no stimulation was applied recently (maximal time programmable). In another embodiment specific for GERD patients, the implantable device inhibits or does not schedule stimulation where the accelerometer or inclinometer detects a supine phase or position.

In one embodiment, the supine stimulation mode can be enabled or disabled by the user via a programmer interface. The supine stimulation mode is available when the implantable device is in "cyclic" and "dose" modes, but not available (grayed out) when the device is in "continuous" and "off" modes. In another embodiment, the supine stimulation mode can be implemented in conjunction with other stimulation modes, as described above, be the only mode of stimulation, or be disabled. In addition, when active, the supine stimulation mode may or may not override regularly scheduled stimulations or manually applied stimulations, depending on the programming. Further, when active, the supine stimulation mode may or may not deliver the same stimulation therapy profile as programmed in the "cyclic", "dose", or other modes, as applicable, depending on the programming.

In one embodiment, when the supine stimulation mode is enabled, an additional set of specific programmable parameters becomes active on the programmer interface. This set includes the following parameters: supine time; supine time percentage; supine refractory time; supine level; supine retrigger time and, supine cancel.

Supine time defines the period of time that is required for the patient to be in a supine position in order for the first condition listed above to be met. Supine time is programmable to a certain time period by the user. In one embodiment, supine time is set to 1 minute. In another embodiment, supine time is set to 5 minutes. In another embodiment, supine time is set to 30 minutes. In yet another embodiment, supine time is set to 60 minutes, or smaller increments thereof.

Supine time percentage defines the minimum percentage of data points required during the supine time in order for the first condition listed above to be met. Supine time percentage is programmable to a certain percentage by the user. In one embodiment, supine time percentage is set to 50 percent. In another embodiment, supine time percentage is set to 70 percent. In another embodiment, supine time percentage is set to 90 percent, or smaller increments thereof.

Figure 9:
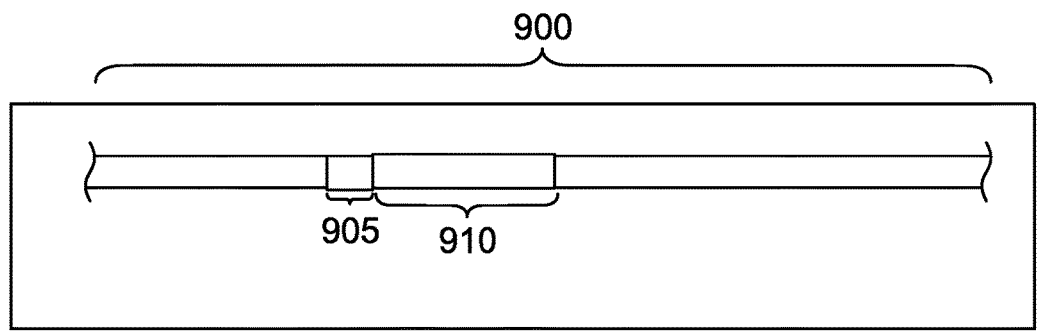
FIG. 9 is an illustration of a one embodiment of a timeline depicting a stimulation session followed by a supine refractory time period.

Supine refractory time defines the minimal amount of time required to have passed from the end of the last stimulation session (scheduled, manual, or supine stimulation) before a new stimulation session may be initiated via the supine stimulation mode. Supine refractory time is programmable to a certain time period by the user. In one embodiment, supine refractory time is set to 30 minutes. In another embodiment, supine refractory time is set to 60 minutes. In another embodiment, supine refractory time is set to 120 minutes. In yet another embodiment, supine refractory time is set to 180 minutes. FIG. 9 is an illustration of a timeline 900 depicting a stimulation session 905 followed by a supine refractory time period 910. The supine refractory time period 910 begins immediately after the end of the stimulation session 905 and continues through its pre-programmed duration. No additional stimulation initiated by the supine stimulation mode can begin until the supine refractory time period 910 has ended.

Supine level defines the level of inclination required to achieve a supine posture. Supine level is programmable to a range of degrees by the user. In one embodiment, where the supine level is measured relative to a horizontal body, supine level is set between 170 and 200 degrees. In another embodiment, supine level is set between 160 and 200 degrees. In another embodiment, supine level is set between 150 and 200 degrees. In yet another embodiment, supine level is set between 140 and 200 degrees. In another embodiment, where the supine level is measured relative to a vertical baseline, supine level is set to an angle of 50, 60, 70, or 80 degrees, where 0 degrees is a vertical position and 90 degrees is a horizontal position.

Figure 10:
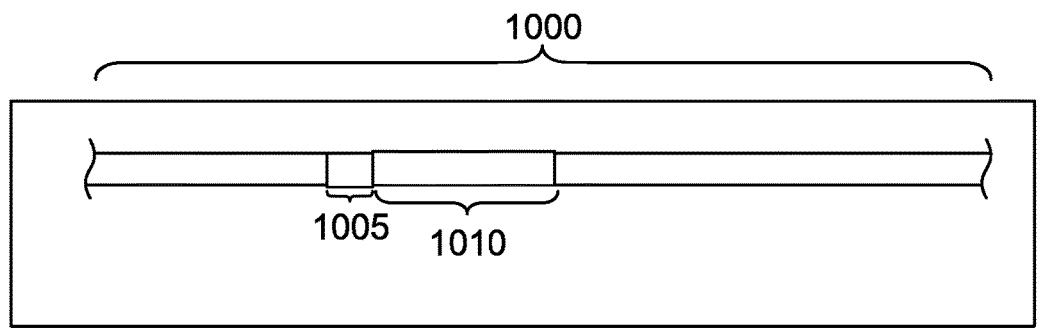
FIG. 10 is an illustration of one embodiment of a timeline depicting a stimulation session triggered by supine stimulation mode followed by a supine cancel period.

Supine cancel defines the maximum amount of time that can elapse between the end of a stimulation therapy session triggered by supine stimulation mode and the start of a regularly scheduled stimulation therapy session that will cancel the regularly scheduled stimulation therapy session. Supine cancel is programmable to a certain time period by the user. In one embodiment, supine cancel is set to 30 minutes. In another embodiment, supine cancel is set to 60 minutes. In another embodiment, supine cancel is set to 120 minutes. In yet another embodiment, supine cancel is set to 240 minutes. FIG. 10 is an illustration of a timeline 1000 depicting a stimulation session 1005 triggered by supine stimulation mode followed by a supine cancel period 1010. The supine cancel period 1010 begins immediately after the end of the supine stimulation mode stimulation session 1005 and continues through its pre-programmed duration. Any regularly scheduled stimulation session scheduled during the supine cancel period 1010 will not be initiated.

Supine retrigger defines the maximum amount of time that may elapse between the end of a stimulation therapy session triggered by supine stimulation mode and the initiation of another stimulation. In one embodiment, the supine retrigger period is programmable and may have a value of 2 4, 6, or 8 hours, or any increment therein. In another embodiment, after a predefined threshold, such as 75%, of a supine retrigger period has passed, the stimulator initiates a post-sleeping stimulation, in anticipation of a breakfast meal event, if a vertical position is sensed. In another embodiment, the stimulator does not initiate a post-sleeping stimulation if a vertical position is sensed if less than a predefined threshold, such as 75%, of a supine retrigger period has passed. It should be appreciated that an automatically set post-sleeping stimulation is optional and that stimulation may simply be preset for a particular time of the day.

Modifications to Prevent Habituation or Fatigue

Stimulation parameters may also be periodically modified, in accordance with a predefined schedule or dynamically by real-time physician or patient control, to reduce, avoid, or prevent the occurrence of muscle fatigue, habituation, and/or tolerance. Manipulation of the length of the "on" and "off" cycles can be performed while still obtaining the desired level of LES function. In one embodiment, the length of stimulation time to achieve the therapeutic goal can be decreased while the stimulation off time required for LES function to return to baseline can be increased. Less time spent in the "on" cycle will result in fewer incidents of muscle fatigue.

In another embodiment, the "on" and "off" cycles, as described previously, can cycle rapidly. For example, during a 30 minute period, the stimulation may be on for 3 seconds and off for 2 seconds during the entire 30 minute period.

In another embodiment, the patient can take a "stimulation holiday". In other words, stimulation can be further stopped for a time period greater than the "off" cycle to allow the muscle to recover. Greatly increasing the time period in which there is no stimulation also serves to avoid muscle fatigue and tolerance.

In another embodiment, stimulation parameters can be intermixed in an attempt to avoid muscle fatigue, habituation, and/or tolerance while still obtaining the desired level of LES function. For example, alternating short pulses can be intermixed with intermediate pulses to stimulate the LES, esophagus, upper esophageal sphincter, stomach, gastric fundus, or gastric cardia. The variation in stimuli received by the muscle will assist in avoiding fatigue and tolerance.

In another embodiment, LES function can be normalized using the present invention without raising LES pressure above the mid-normal range. This is achieved by minimizing the energy delivered to the muscle to, but not beyond, the point where the LES regains normal function. Less energy delivered results in less fatigue and tolerance.

In another embodiment, the stimulation parameters can be changed, such as by modifying pulse width, frequency, amplitude, ramp rate, or the duty cycle, on a predefined periodic basis to avoid having the muscles habituate to a known and repeated stimulation setting. In such an embodiment, a stimulator may locally store a plurality of different stimulation parameters which are implemented in accordance with a predefined schedule. The stimulator may also store a single set of stimulation parameters, each parameter having an acceptable range of operation, and then randomly implement a stimulation parameter bounded by the acceptable ranges of operation.

Figure 11:
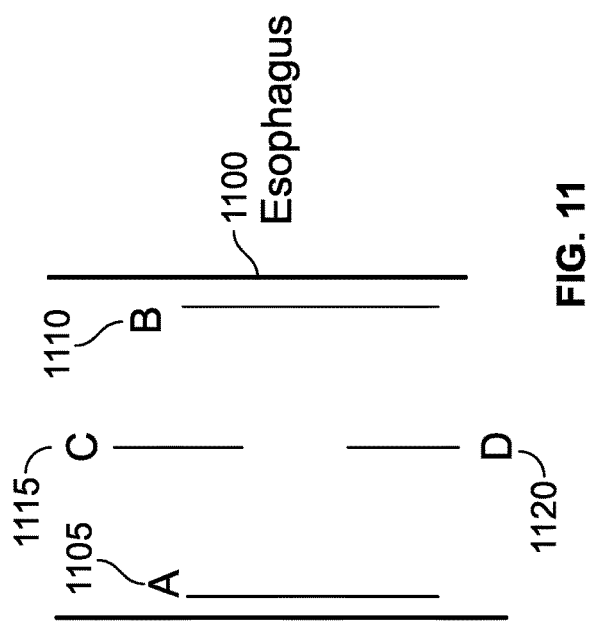
FIG. 11 is an illustration depicting one exemplary electrode configuration in the esophagus of a patient.

Electrode Configurations and Methods of Placing and Confirming the Placement of Electrodes In one embodiment, the therapeutic objectives described herein are achieved by at least one of a plurality of different electrode configurations, as shown in FIG. 11. It should be appreciated that, in one embodiment, the electrode placement, as shown, at least partly enables the patient's LES function to normalize, post-stimulation, and/or the length of the patient's LES high pressure zone to increase or gastric pressure to decrease post-stimulation. The electrode configurations described herein may be used in accordance with any of the stimulation parameters, system architectures, and sensing systems described herein.

Within the esophagus 1100, and more particularly the LES, a plurality of different electrode combinations can be used to achieve the therapeutic and operational objectives described herein. In one embodiment, a first electrode 1105 is placed proximate to the left lateral wall of the esophagus 1100 and operated in combination with a second electrode placed proximate to the right lateral wall 1110 of the esophagus 1100. In one embodiment, a first electrode 1105 is placed proximate to the left lateral wall of the esophagus 1100 and operated in combination with a second electrode placed in the anterior proximal wall 1115 of the esophagus 1100. In one embodiment, a first electrode 1110 is placed proximate to the right lateral wall of the esophagus 1100 and operated in combination with a second electrode placed in the anterior proximal wall 1115 of the esophagus 1100. In another embodiment, a first electrode 1105 is placed proximate to the left lateral wall of the esophagus 1100 and operated in combination with a second electrode placed in the anterior, distal wall 1120 of the esophagus 1100. In one embodiment, a first electrode 1110 is placed proximate to the right lateral wall of the esophagus 1100 and operated in combination with a second electrode placed in the anterior, distal wall 1120 of the esophagus 1100. In another embodiment, a first electrode 1115 and a second electrode 1120 are placed proximally and distally in the anterior wall of the esophagus 1100. In another embodiment, more than one of the above described combinations are used serially along the length of the esophagus 1100.

Figure 12:
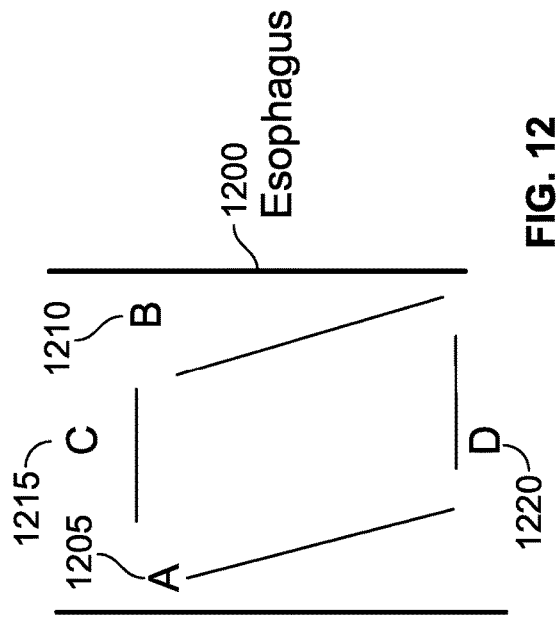
FIG. 12 is an illustration depicting another exemplary electrode configuration in the esophagus of a patient.

Referring to FIG. 12, the electrodes 1205, 1210, 1215, 1220 can be placed longitudinally or transversely or in any orientation relative to the length of the esophagus 1200 and can be implemented in the same exemplary combinations described in relation to FIG. 11. It should be appreciated that not all of the electrodes shown in FIG. 11 need to be implanted or operated concurrently. For example, to achieve any of the aforementioned therapeutic objectives, only one pair of electrodes, such as 1105 and 1110 or 1115 and 1120 need be implanted and/or operated concurrently.

Figure 13A:
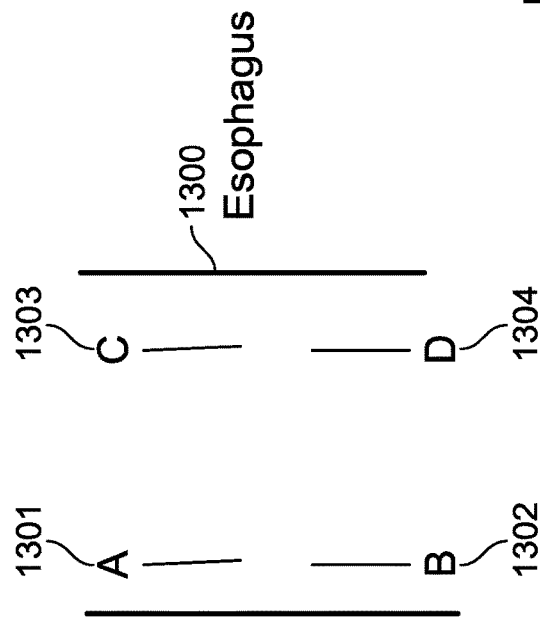
FIG. 13A is an illustration depicting another exemplary electrode configuration in the esophagus of a patient.

In another embodiment, shown in FIG. 13A, electrodes can be implanted in series with two electrodes 1301, 1302 proximate to the left lateral wall of the esophagus 1300 and two electrodes 1303, 1304 proximate to the right lateral wall of the esophagus 1300. These electrodes can be activated in various combinations, as described above, to provide for the optimal normalization of LES pressure, with minimal energy delivered to the tissue and minimal muscle fatigue or depletion of neurotransmitter storages. It should be appreciated that, in one embodiment, stimulation parameters (amplitude, timing of stimulation session and switching of electrode configuration) will be set so as to activate release of the appropriate neurotransmitter. Such parameters can vary between patients due to surgical variation and physiological sensitivity. The electrode activation or implantation combinations can include electrodes 1301 and 1303, electrodes 1301 and 1302, electrodes 1303 or 1304, electrodes 1301/1303 alternating with 1302/1304, and electrodes 1301/1302 alternating with 1303/1304.

It should be appreciated that the length and surface area of the electrode and the distance between the electrodes can affect the degree and duration of the patient's post-stimulation normalization of LES function. It should further be appreciated that the length and surface area of the electrode can affect the current amplitude required to increase the length of the LES high pressure zone or decrease gastric pressure post-stimulation.

In one embodiment, a patient is treated to achieve any one of the aforementioned therapeutic objectives by implanting the electrodes in a "linear" configuration. This is accomplished by implanting a first electrode axially along the length of the smooth muscle of the LES, shown as 1115 in FIG. 11, and implanting a second electrode 1120 below and substantially in alignment with the first electrode 1115. In various embodiments, the bottom of the first electrode 1115 is separated from the top of the second electrode 1120 by a distance of no greater than 5 cm, preferably no greater than 2 cm, and most preferably approximately 1 cm. Each electrode is placed preferably more than 1 mm away from the vagal trunk. This electrode configuration is supplied with a stimulation pulse from a stimulator. The stimulation pulse may be delivered in accordance with any of the aforementioned stimulation parameters. In one embodiment, the stimulation pulse has a pulse amplitude no greater than 15 mAmp and more preferably no greater than 8 mAmp. In one embodiment, the stimulation pulse has a pulse width of approximately 200 μsec and a pulse repetition frequency of 20 Hz. A stimulator may further be configured to detect any of the aforementioned biological parameters, including length of the LES high pressure zone and gastric pressure. In one embodiment, the length of the LES high pressure zone or gastric pressure is derived from a plurality of sensors adapted to generate impedance measurements. In one embodiment, the length of the LES high pressure zone or gastric pressure is derived from piezoelectric sensors or electrical activity based sensors.

In one embodiment, a patient is treated to achieve any one of the aforementioned therapeutic objectives by implanting the electrodes in a "parallel" configuration. Referring again to FIG. 11, this is accomplished by implanting a first electrode 1105 axially along the length of the smooth muscle of the LES and implanting a second electrode 1110 axially on the other side of the esophagus 1100, parallel to the first electrode 1105. In one embodiment, the distance between the first electrode 1105 and the second electrode 1110 is less than half the circumference of the LES. The electrodes 1105, 1110 are implanted in the anterior portion of the LES, with preferably at least one electrode being in the right anterior portion of the LES (this places the stimulation as far as possible from the heart). Each electrode is placed preferably more than 1 mm away from the vagal trunk. This electrode configuration is supplied with a stimulation pulse from a stimulator. The stimulation pulse may be delivered in accordance with any of the aforementioned stimulation parameters. In one embodiment, the stimulation pulse has a pulse amplitude no greater than 15 mAmp and more preferably no greater than 8 mAmp. In one embodiment, the stimulation pulse has a pulse width of approximately 200 μsec. A stimulator may further be configured to detect any of the aforementioned biological parameters, including length of the LES high pressure zone or gastric pressure. In one embodiment, the length of the LES high pressure zone or gastric pressure is derived from a plurality of sensors adapted to generate impedance measurements. In one embodiment, the length of the LES high pressure zone or gastric pressure is derived from piezoelectric sensors or electrical activity based sensors.

Referring now to FIG. 12, in one embodiment, a patient is treated to achieve any one of the aforementioned therapeutic objectives by implanting a first electrode 1215 transaxially across the length of the smooth muscle of the LES and implanting a second electrode 1220 substantially parallel to the first electrode and spaced apart from the first electrode 1215 by a distance of no greater than 5 cm. This electrode configuration is supplied with a stimulation pulse from a stimulator. The stimulation pulse may be delivered in accordance with any of the aforementioned stimulation parameters. In one embodiment, the stimulation pulse has a pulse amplitude no greater than 15 mAmp and more preferably no greater than 8 mAmp. In one embodiment, the stimulation pulse has a pulse width of approximately 200 μsec. A stimulator may further be configured to detect any of the aforementioned biological parameters, including length of the LES high pressure zone or gastric pressure. In one embodiment, the length of the LES high pressure zone or gastric pressure is derived from a plurality of sensors adapted to generate impedance measurements. In one embodiment, the length of the LES high pressure zone or gastric pressure is derived from piezoelectric sensors or electrical activity based sensors.

In one embodiment, a patient is treated to achieve any one of the aforementioned therapeutic objectives by implanting a first electrode and a second electrode in a configuration that concentrates current density at two or fewer points close to each electrode. This electrode configuration is supplied with a stimulation pulse from a stimulator. The stimulation pulse may be delivered in accordance with any of the aforementioned stimulation parameters. In one embodiment, the stimulation pulse has a pulse amplitude no greater than 15 mAmp and more preferably no greater than 8 mAmp. In one embodiment, the stimulation pulse has a pulse width of approximately 200 μsec.

In one embodiment, a patient is treated to achieve any one of the aforementioned therapeutic objectives by implanting a first electrode and a second electrode in a configuration that avoids distributing substantially all of the current density along the length of each electrode. This electrode configuration is supplied with a stimulation pulse from a stimulator. The stimulation pulse may be delivered in accordance with any of the aforementioned stimulation parameters. In one embodiment, the stimulation pulse has a pulse amplitude no greater than 15 mAmp and more preferably no greater than 8 mAmp. In one embodiment, the stimulation pulse has a pulse width of approximately 200 μsec.

Variations in the stimulation and placement of electrodes also convey the added benefit of avoiding muscle fatigue and tolerance, as previously discussed. For example, as shown in FIG. 12, two pairs of electrodes, 1205/1210 and 1215/1220, can be implanted and stimulated in alternative succession. In one embodiment, the two pairs of electrodes receive simultaneous stimulations with the same stimulation parameters. In another embodiment, the two pairs of electrodes receive sequential stimulations with the same stimulation parameters. In another embodiment, the two pairs of electrodes receive simultaneous stimulations with different stimulation parameters. In another embodiment, the two pairs of electrodes receive sequential stimulations with different stimulation parameters. Electrode placement can also be manipulated to decrease muscle fatigue and tolerance. In one embodiment, the two pairs of electrodes are placed so that the distance between any set of electrodes is less than two times the distance between the pair of electrodes, resulting in the stimulation from a set of electrodes stimulating less than 100% of the LES.

Preferably, during the implantation process, electrode configurations are tested to verify that the proper configuration has been achieved. In one embodiment, a catheter or endoscope configured to measure gastric or LES pressure in combination with a manometer is advanced to a location proximate the implantation area while the newly implanted electrodes are stimulated. LES pressure is measured before, during, and/or after stimulation. If the desired gastric pressure profile or LES pressure profile in the high pressure zone is achieved, the implantation is deemed successful and the testing may terminate. If the desired gastric pressure profile or LES pressure profile in the high pressure zone is not achieved, the electrode configuration may be modified. Gastric and/or LES pressure testing is then repeated until the proper gastric pressure profile or LES pressure profile in the high pressure zone is achieved. Other sensed data, such as temperature, may also be used in this testing process. It should be appreciated that the testing process can be conducted separate from the implantation procedure. For example, patients can be tested with temporary electrodes, inserted non-invasively (nasogastrically, for example), and upon success can be deemed suitable for implant.

Figure 13C:
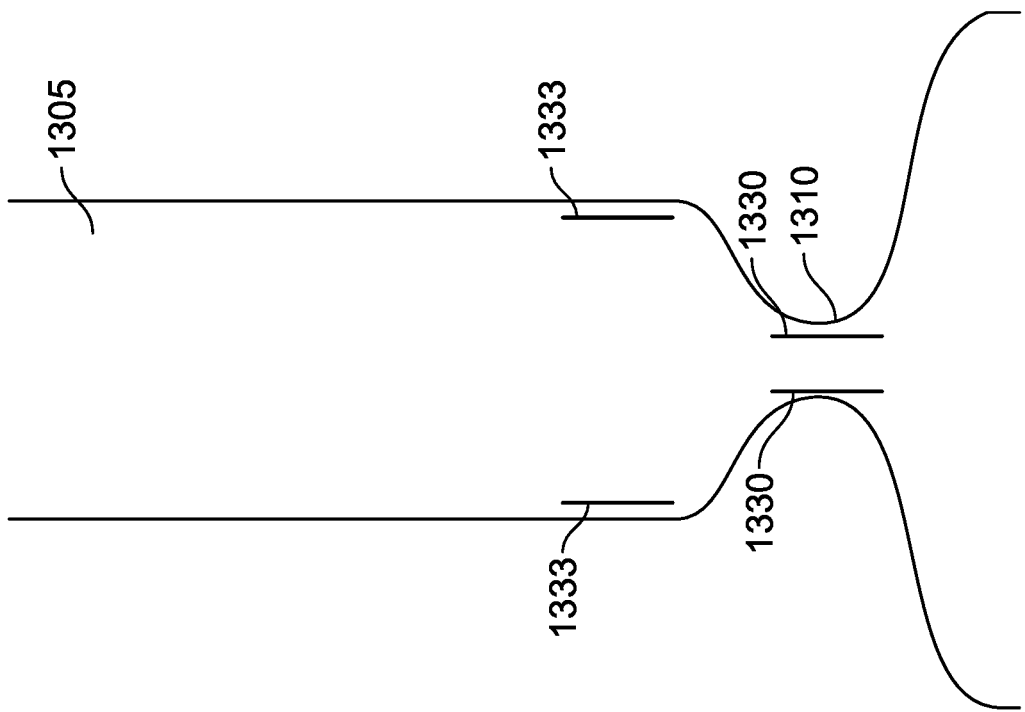
FIG. 13C is an illustration of the distal portion of an esophagus of a patient depicting a first pair of electrodes implanted in the LES and a second pair of electrodes implanted proximate the LES, in accordance with one embodiment of the present specification.
Figure 13B:
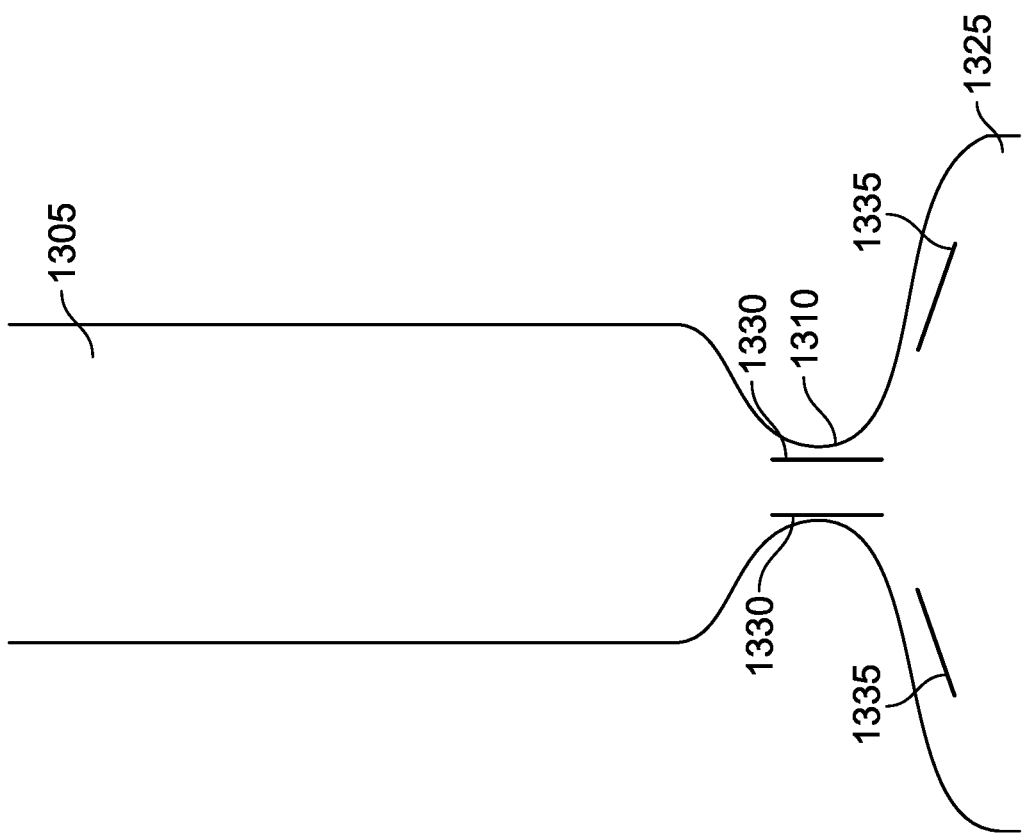
FIG. 13B is an illustration of the distal portion of an esophagus of a patient depicting a first pair of electrodes implanted in the LES and a second pair of electrodes implanted in the gastric cardia, in accordance with one embodiment of the present specification.

In various embodiments, additional stimulating electrodes are implanted within the gastrointestinal tract to be used in conjunction with, or in place of, the electrodes implanted in the LES detailed above. FIGS. 13B through 13F illustrate various optional electrode configurations in the lower esophagus, LES, and gastric cardia for stimulation targeted to increase the length of the LES high pressure zone. FIG. 13B is an illustration of the distal portion of an esophagus 1305 of a patient depicting a first pair of electrodes 1330 implanted in the LES 1310 and a second pair of electrodes 1335 implanted in the gastric cardia 1325. FIG. 13C is an illustration of the distal portion of an esophagus of a patient depicting a first pair of electrodes 1330 implanted in the LES 1310 and a second pair of electrodes 1333 implanted proximate the LES 1310, in accordance with another embodiment of the present specification.

Figure 13E:
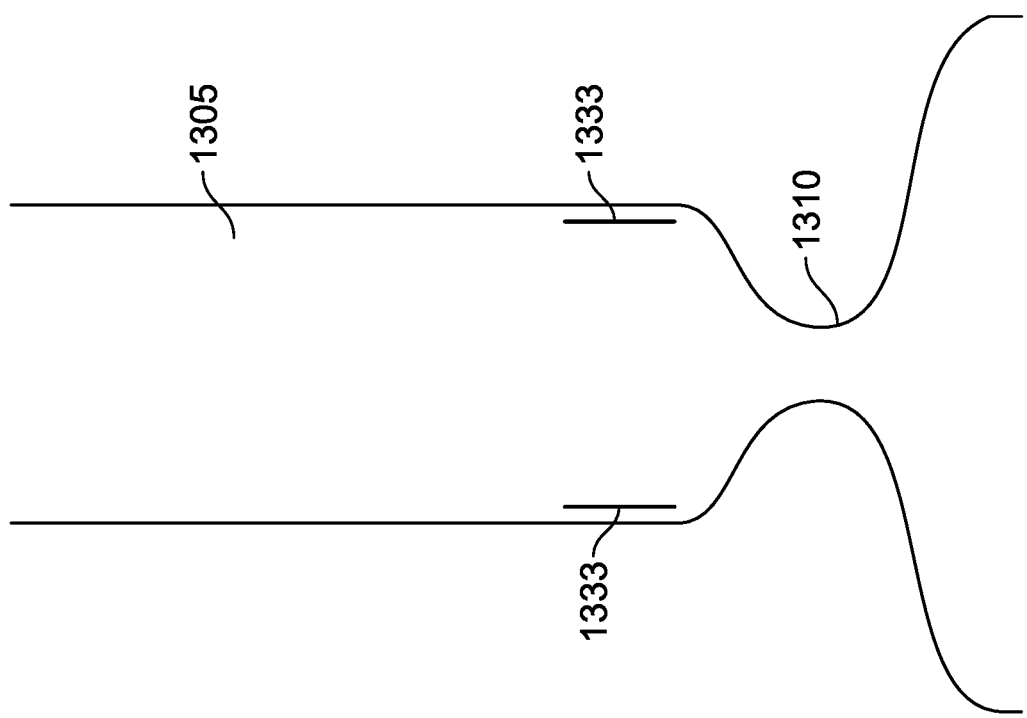
FIG. 13E is an illustration of the distal portion of an esophagus of a patient depicting a pair of electrodes implanted proximate the LES, in accordance with one embodiment of the present specification.
Figure 13D:
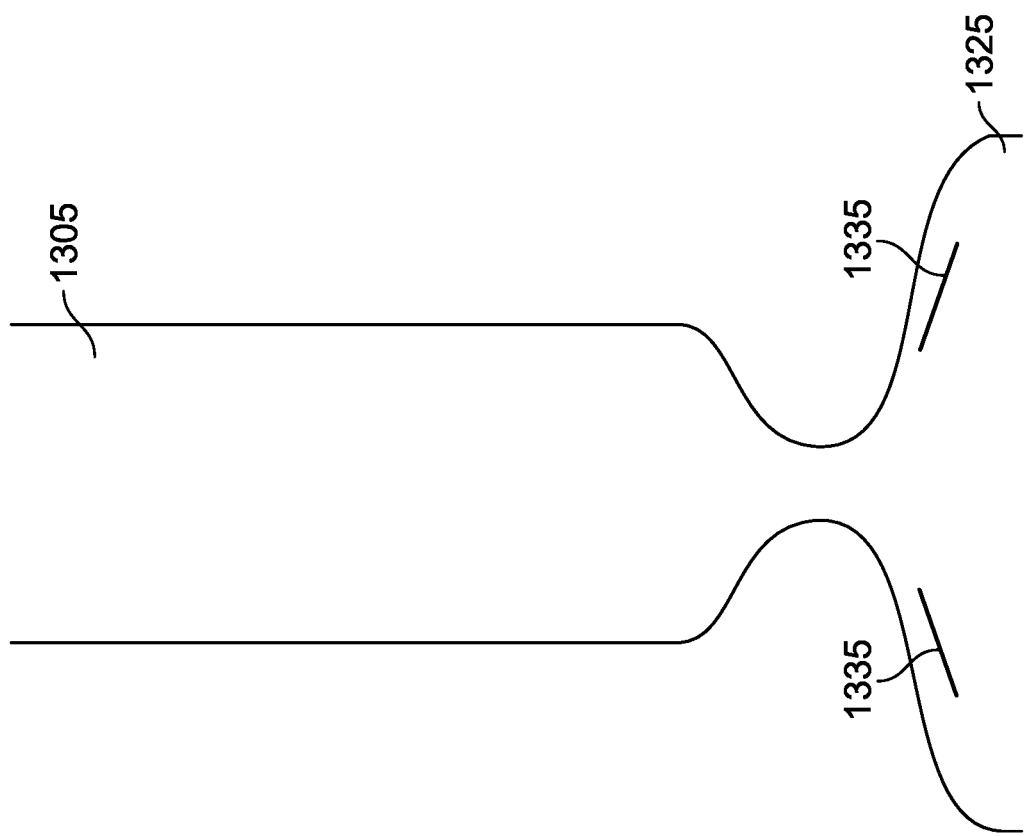
FIG. 13D is an illustration of the distal portion of an esophagus of a patient depicting a pair of electrodes implanted in the gastric cardia, in accordance with one embodiment of the present specification.
Figure 13G:
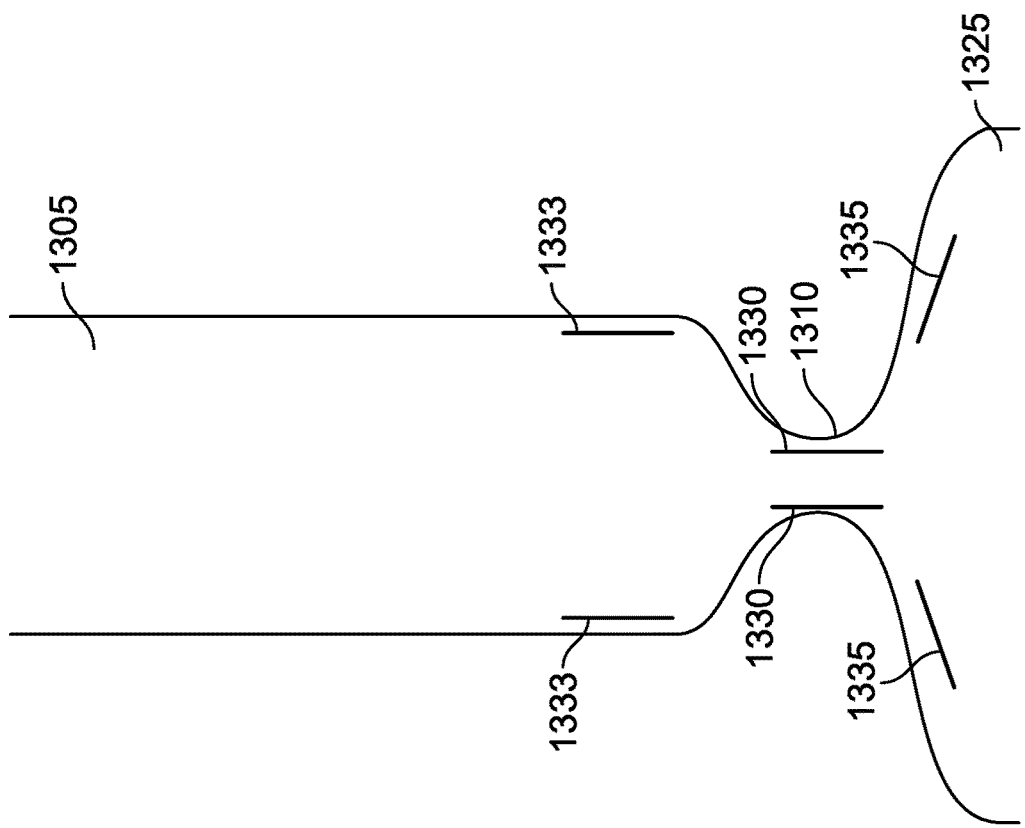
FIG. 13G is an illustration of the distal portion of an esophagus of a patient depicting a first pair of electrodes implanted in the LES, a second pair of electrodes implanted in the gastric cardia, and a third pair of electrodes implanted proximate the LES, in accordance with one embodiment of the present specification.
Figure 13F:
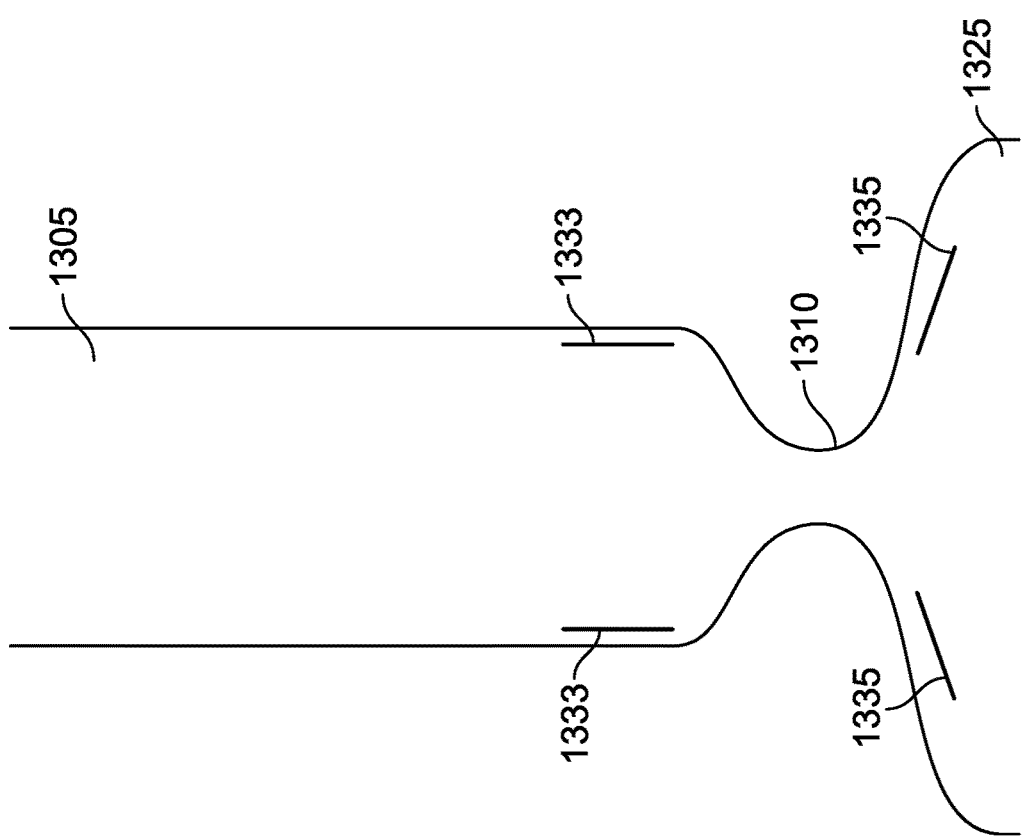
FIG. 13F is an illustration of the distal portion of an esophagus of a patient depicting a first pair of electrodes implanted in the gastric cardia and a second pair of electrodes implanted proximate the LES, in accordance with one embodiment of the present specification.

FIG. 13D is an illustration of the distal portion of an esophagus 1305 of a patient depicting a pair of electrodes 1335 implanted in the gastric cardia 1325, in accordance with another embodiment of the present specification. FIG. 13E is an illustration of the distal portion of an esophagus 1305 of a patient depicting a pair of electrodes 1333 implanted proximate the LES 1310, in accordance with one embodiment of the present specification;

FIG. 13F is an illustration of the distal portion of an esophagus 1305 of a patient depicting a first pair of electrodes 1335 implanted in the gastric cardia 1325 and a second pair of electrodes 1333 implanted proximate the LES 1310, in accordance with another embodiment of the present specification. FIG. 13G is an illustration of the distal portion of an esophagus 1305 of a patient depicting a first pair of electrodes 1330 implanted in the LES 1310, a second pair of electrodes 1335 implanted in the gastric cardia 1325, and a third pair of electrodes 1333 implanted proximate the LES 1310, in accordance with one embodiment of the present specification.

In various embodiments, any of the electrode configurations can be used with any methodology disclosed in the present specification to enhance the length of the LES high pressure zone to achieve any of the therapeutic goals listed above.

Figure 13I:
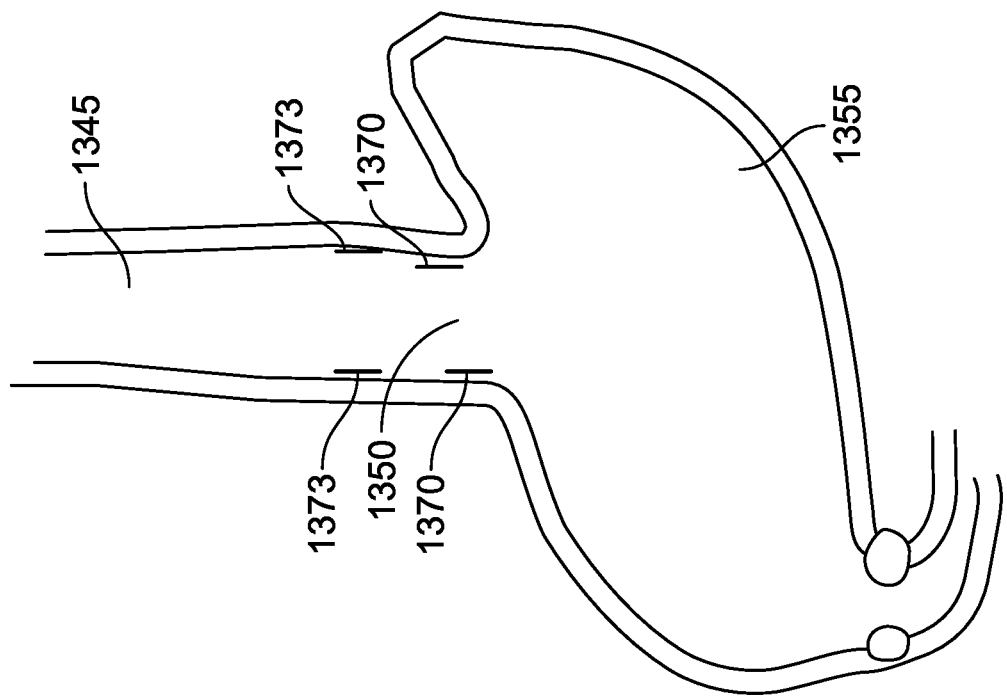
FIG. 13I is an illustration of the distal portion of an esophagus of a patient depicting a first pair of electrodes implanted in the LES and a second pair of electrodes implanted proximate the LES, in accordance with one embodiment of the present specification.
Figure 13H:
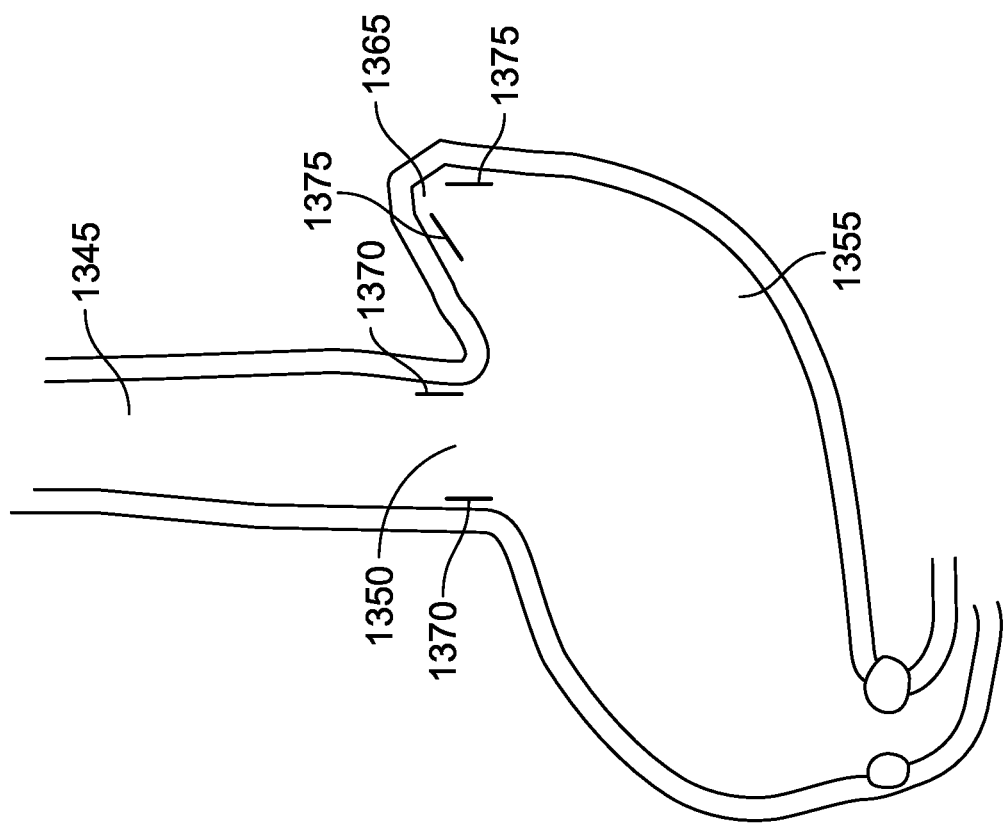
FIG. 13H is an illustration of the distal portion of an esophagus of a patient depicting a first pair of electrodes implanted in the LES and a second pair of electrodes implanted in the gastric fundus, in accordance with one embodiment of the present specification.

FIGS. 13H through 13M illustrate various optional electrode configurations in the lower esophagus, LES, and gastric fundus targeted to increase the receptive relaxation response of the stomach and decrease gastric pressure. FIG. 13H is an illustration of the distal portion of an esophagus 1345 and a stomach 1355 of a patient depicting a first pair of electrodes 1370 implanted in the LES 1350 and a second pair of electrodes 1375 implanted in the gastric fundus 1365. FIG. 13I is an illustration of the distal portion of an esophagus 1345 and a stomach 1355 of a patient depicting a first pair of electrodes 1370 implanted in the LES 1350 and a second pair of electrodes 1373 implanted proximate the LES 1350, in accordance with another embodiment of the present specification.

Figure 13K:
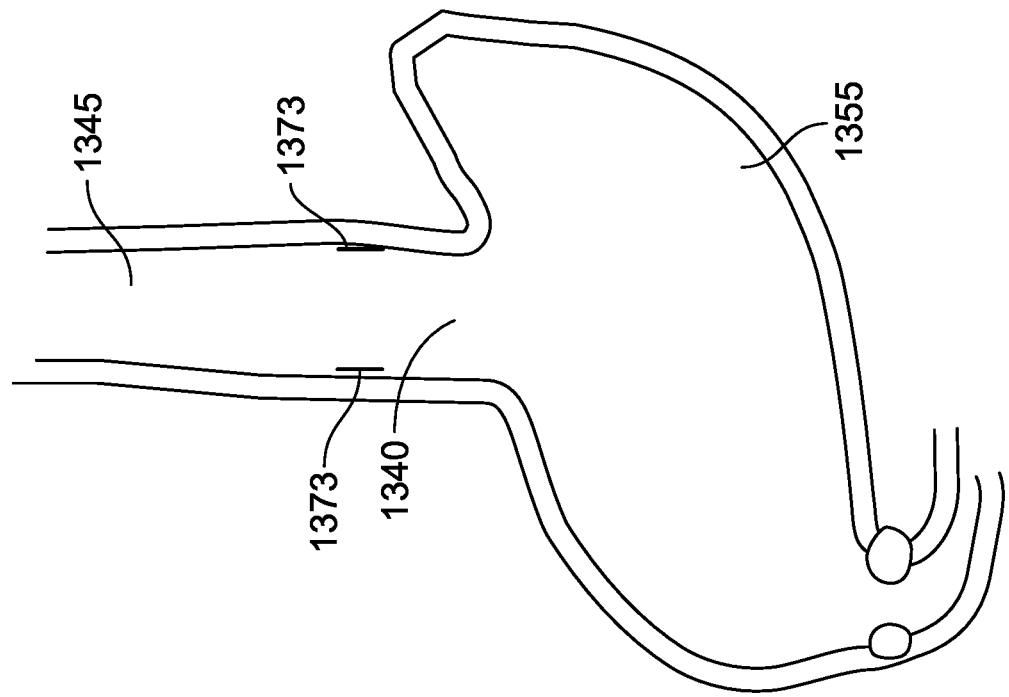
FIG. 13K is an illustration of the distal portion of an esophagus of a patient depicting a pair of electrodes implanted proximate the LES, in accordance with one embodiment of the present specification.
Figure 13J:
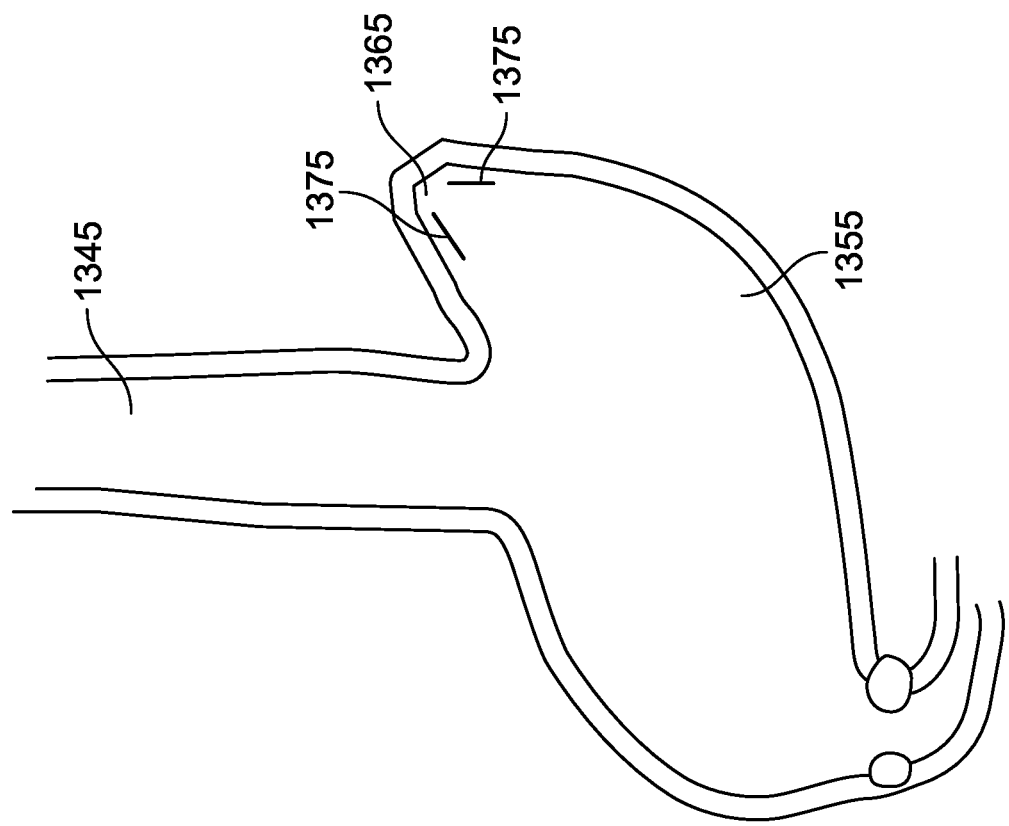
FIG. 13J is an illustration of the distal portion of an esophagus of a patient depicting a pair of electrodes implanted in the gastric fundus, in accordance with one embodiment of the present specification.

FIG. 13J is an illustration of the distal portion of an esophagus 1345 and a stomach 1355 of a patient depicting a pair of electrodes 1375 implanted in the gastric fundus 1365, in accordance with another embodiment of the present specification. FIG. 13K is an illustration of the distal portion of an esophagus 1345 and a stomach 1355 of a patient depicting a pair of electrodes 1373 implanted proximate the LES 1350, in accordance with one embodiment of the present specification.

Figure 13M:
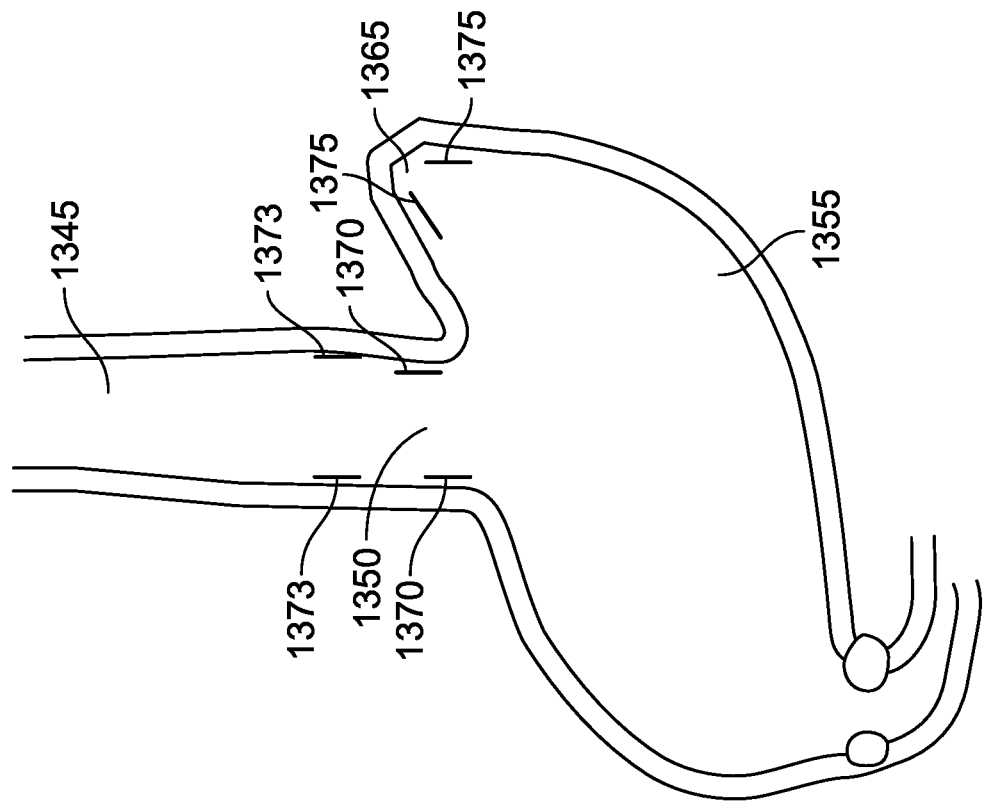
FIG. 13M is an illustration of the distal portion of an esophagus of a patient depicting a first pair of electrodes implanted in the LES, a second pair of electrodes implanted in the gastric fundus, and a third pair of electrodes implanted proximate the LES, in accordance with one embodiment of the present specification.
Figure 13L:
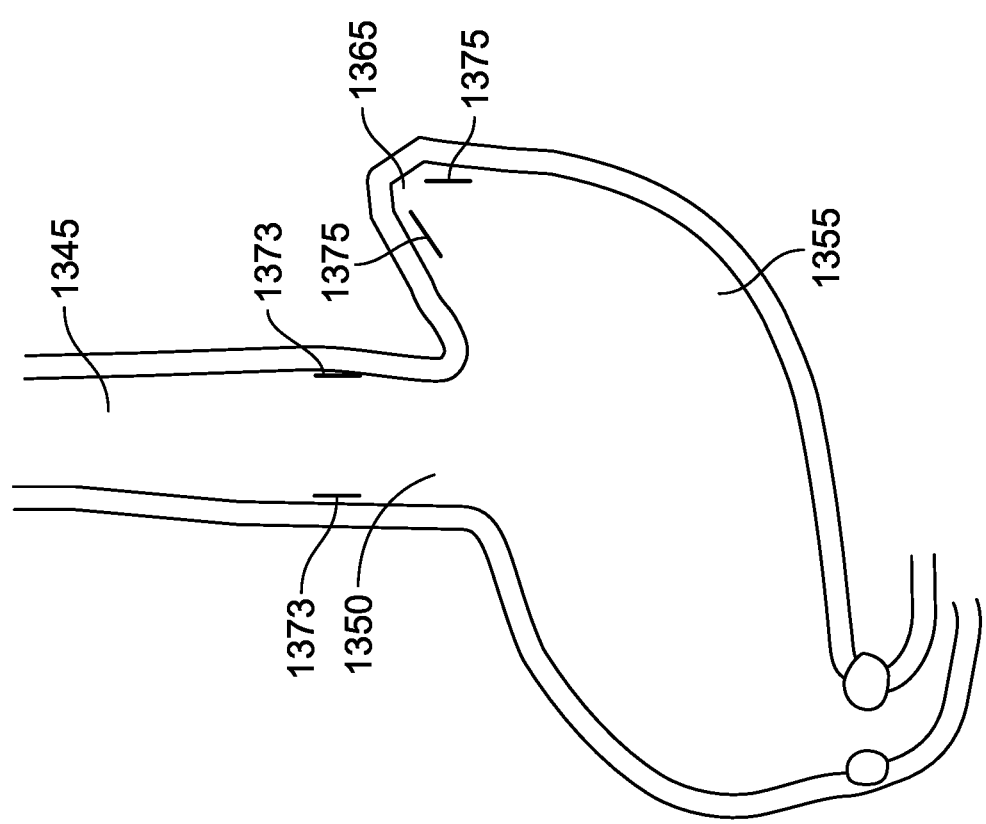
FIG. 13L is an illustration of the distal portion of an esophagus of a patient depicting a first pair of electrodes implanted in the gastric fundus and a second pair of electrodes implanted proximate the LES, in accordance with one embodiment of the present specification.

FIG. 13L is an illustration of the distal portion of an esophagus 1345 and a stomach 1355 of a patient depicting a first pair of electrodes 1375 implanted in the gastric fundus 1365 and a second pair of electrodes 1373 implanted proximate the LES 1350, in accordance with another embodiment of the present specification. FIG. 13M is an illustration of the distal portion of an esophagus 1345 and a stomach 1355 of a patient depicting a first pair of electrodes 1370 implanted in the LES 1350, a second pair of electrodes 1375 implanted in the gastric fundus 1365, and a third pair of electrodes 1373 implanted proximate the LES 1350, in accordance with one embodiment of the present specification.

In various embodiments, any of the electrode configurations can be used with any methodology disclosed in the present specification to modulate fundus tone and decrease gastric pressure to achieve any of the therapeutic goals listed above.

Stimulator Energy Storage and Sensing Systems
Non-Sensing Active Implantable Medical Devices The embodiments disclosed herein achieve one or more of the above listed therapeutic objectives using stimulation systems that are energy efficient and do not require sensing systems to identify wet swallows, bolus propagation, or patient symptom changes, thereby enabling a less complex, smaller stimulation device which can more readily be implanted using endoscopic, laparoscopic or stereotactic techniques. The disclosed stimulation methods permit a natural wet or bolus swallow to override the electrically induced stimulation effect, thereby allowing for a natural wet or bolus swallow without having to change, terminate, or modify the stimulation parameters.

It should be appreciated that, in one embodiment, the stimulation device receives energy from a remote energy source that is wirelessly transmitting ultrasound or RF based energy to the stimulation device, which comprises receivers capable of receiving the energy and directing the energy toward stimulating one or more electrodes. It should further be appreciated that the device may be voltage driven or current driven, depending upon the chosen embodiment.

It should be appreciated that, in another embodiment, the stimulation device is a macrostimulator that receives energy from a local energy source, such as a battery, and directs the energy toward stimulating one or more electrodes. It should further be appreciated that the device may be voltage driven or current driven, depending upon the chosen embodiment.

By not requiring sensing systems that identify wet swallows, bolus propagation, or patient symptom changes, at least certain embodiments can operate with increased reliability and also be smaller in size. The smaller device size results in increased patient comfort, allows for placement (implantation) in the patient in more appropriate and/or convenient locations in the patient's anatomy, and allows the use of different surgical techniques for implantation (laparoscopic, endoscopic) and/or smaller incisions, which are less invasive, cause less trauma, cause less tissue damage, and have less risk of infection. The small size can also allow placement of a larger number of devices so as to provide redundancy, improved clinical efficacy, durability and reliability.

In addition to the absence of certain components which, conventionally, were required to be part of such an electrical stimulation system, embodiments of the present specification can achieve the above-listed therapeutic objectives using stimulation systems that operate at low energy level, such as at or below 20 Hz with a current of at or below 8 mAmp, preferably 3 mAmp, and a pulse width of 200 μsec.

As a result of the operative energy range, the following benefits can be achieved: a) a wider range of electrode designs, styles, or materials may be implemented, b) the need to use special protective coatings on electrodes, such as iridium oxide, or titanium nitride, while still maintaining electrode surface areas below 5 mm$^2$, is eliminated, c) one has the option of using small electrode surface areas, preferably below a predefined size with coatings to increase the effective surface area, such as iridium oxide, or titanium nitride, d) one can operate in wireless energy ranges that are within regulatory guidelines and safety limits and do not pose interference issues, such as a RF field strength below a predefined limit and ultrasound field strength below a predefined limit.

It should further be appreciated that the presently disclosed systems can be implemented using a variety of surgical techniques, including laparoscopic and endoscopic techniques. In one embodiment, a laparoscopically implanted device comprises a battery providing local energy storage and only optionally receives energy through wireless transfer, such as RF or ultrasound. In such an embodiment, the device stimulates at a higher amperage for shorter periods of time, relative to embodiments without local energy storage, thereby allowing for longer off cycles, lower duty cycles, and better battery efficiency. In one embodiment, an endoscopically implanted device may or may not comprise a local energy storage device but does comprise a wireless receiver to receive energy wirelessly transmitted from an external energy source and transmission device. In such an embodiment, this device stimulates at a lower energy setting for longer on cycles and shorter off cycles, relative to the embodiment with local energy storage, thereby having a greater duty cycle than a laparoscopic implant.

The stimulators of the present specification, when properly programmed in accordance with the stimulation parameters described herein and associated with the appropriate electrode configurations, exhibit a high degree of energy efficiency. In one embodiment, the electrical stimulation device initiates electrical stimulation based upon an internal clock or a patient activated trigger. Electrical stimulation then continues for a pre-set or predefined period of time. Referencing a 24 hour period of time, the preset or predefined period of time may be equal to an "on" time period that is less than or equal to 24 hours, 12 hours, 1 second, or any increment therein. Upon completion of that predefined period of time, the internal clock then causes the electrical stimulation device to terminate electrical stimulation.

It should be appreciated that any activation by an internal clock can be configured to cycle daily or a few times daily or be synchronized to meal times, as signaled manually by a patient. It should further be appreciated that the timing of meal times or other physiologically relevant events can be saved and/or learned, thereby enabling the device to default to standard initiation of stimulation time or termination of stimulation time based upon past data gathered. The setting of stimulation times may be set by a physician, based on an interview with a patient or based on the detection of eating using pH sensing or some other automated eating detection mechanism. In one embodiment, stimulation is initiated in advance of a predefined meal time to achieve an increase in LES tone before the patient eats. For example, if a patient's predefined meal time is 2 pm, then stimulation is set to initiate in advance of 2 pm, such as 1:30 pm. If the patient then reports symptoms between 4-6 pm, then, in the future, stimulation may be reinitiated at 3 pm. If a patient's predefined meal time is 12 pm, then set stimulation is set to initiate in advance of 12 pm, such as 11:30 am. If the patient then reports symptoms between 2-4 pm, stimulation may be reinitiated at 1 pm.

In another embodiment, the electrical stimulation device initiates electrical stimulation based upon an internal clock or a patient activated trigger. Electrical stimulation then continues for a pre-set or predefined period of time. Upon completion of that predefined period of time, the internal clock then causes the electrical stimulation device to terminate electrical stimulation. This ratio of the predefined period of stimulation relative to the time where electrical stimulation is terminated is less than 100%, up to a maximum duty cycle, such as 70%, 75%, 80%, 85%, 90%, 95%, or any increment therein.

In another embodiment, the electrical stimulation device initiates electrical stimulation based upon an internal clock or a patient activated trigger. Electrical stimulation then continues for a pre-set or predefined period of time. The pre-set or predefined period of time may be equal to a time period that is up to a maximum "on" period, such as 12 hours, during which the device may be continually operating. Upon completion of that predefined period of time, the internal clock then causes the electrical stimulation device to terminate electrical stimulation.

In another embodiment, the electrical stimulation device initiates electrical stimulation based upon an internal clock or a patient activated trigger. Electrical stimulation then continues for a pre-set or predefined period of time. The pre-set or predefined period of time may be equal to a time period that is up to a maximum "off" period, such as 12 hours, during which the device is not operating. Upon completion of that predefined period of time, the internal clock then causes the electrical stimulation device to restart electrical stimulation.

In another embodiment, the electrical stimulation device initiates electrical stimulation based upon an internal clock or a patient activated trigger. Electrical stimulation then continues for a pre-set or predefined period of time. The pre-set or predefined period of time may be equal to a time period that is less than the time required to see a visible change in the length of the LES high pressure zone or gastric pressure. Upon completion of that predefined period of time, the internal clock then causes the electrical stimulation device to terminate electrical stimulation. The desired increase in the length of the LES high pressure zone or decrease in gastric pressure occurs post-stimulation, followed by a decrease in high pressure zone length or an increase in gastric pressure which still remains beyond a pre-stimulation state after a period of >1 hour.

It should be appreciated that other stimulation protocols, which result in the desired effect of operating for less than 100% of duty cycle and which have a pre-set or predefined period of non-stimulation, can be achieved using combinations of turning on and off subsets of electrodes at different times. For example, one may turn a first subset of electrodes on, turn a second subset of electrodes on, then turn all electrodes off, followed by turning a second subset of electrodes on, turning a first subset of electrodes on, and then all electrodes off again.

Sensing Active Implantable Medical Devices

It should be appreciated that the systems of the present specification can be optionally operated in combination with sensing systems capable of sensing physiological events, such as eating, swallowing, a bolus propagating through the esophagus, muscle fatigue, pH level, esophageal pressure, tissue impedance, length of LES high pressure zone, LES tone/pressure, gastric pressure, patient position, sleep state, or awake state. In such a case, a physiological event can be used to modify the stimulation schedule by, for example, extending the stimulation time period based upon sensed pH level, eating, swallowing, or a bolus propagating through the esophagus or, for example, terminating the stimulation period before the preset time period expires based upon sensed muscle fatigue.

It should also be appreciated that the present invention can be driven by, and fully triggered by, sensing systems capable of sensing physiological events, such as eating, swallowing, a bolus propagating through the esophagus, muscle fatigue, pH level, esophageal pressure, tissue impedance, length of LES high pressure zone, LES tone/pressure, gastric pressure, patient position, sleep state, or awake state. In such a case, a physiological event can be used to initiate the stimulation schedule.

By operating the stimulation system less than 100% duty cycle and having the stimulation device be off during preselected periods, the presently disclosed stimulation system uses less energy than prior art devices. Accordingly, the stimulation systems disclosed herein can effectively operate to achieve the above-listed therapeutic objectives using an energy source local to the stimulator that a) does not include a battery, b) includes a small battery capable of being recharged from an external energy source, c) only includes a capacitor and, more specifically, a capacitor having a rating of less than 0.1 Farads or d) only includes a battery that is not rechargeable.

In one embodiment, a stimulator uses a remote data sensor for automatically adjusting parameters. The stimulator comprises stimulating circuitry contained within a housing that includes a power source, means for delivering stimulation, a receiver to collect data from a remote sensor and a control unit that analyzes the data received from the receiver and adjusts the stimulation parameters based on a plurality of stored programmatic instructions and the received data. The means for stimulation may include any form of leaded or a leadless device. The stimulator element would preferably be implanted either under the skin, in cases where the stimulator comprises a macrostimulator internal pulse generator (IPG), or close to the stimulation area, in cases where the stimulator comprises a microstimulator. The stimulator can also comprise a plurality of separate units, in separate housings, including, for example, an external control unit and receiver and an implantable stimulator, similar to a passive microstimulator.

The stimulator is in wireless or wired data communication with one or more sensor elements. The sensor elements are implanted in an area that allows the sensor to collect physiological data relevant to the controlling the operation of the stimulator. Each sensor element includes means for sensing the required physiological function and means for transmitting the data to the control unit. In one embodiment, the sensor element comprises a capsule adapted to measure physiological pH and transmit pH data from within the lumen of the esophagus to an implantable stimulator device. In another embodiment, the sensor element comprises a pH sensor located within a nasogastric tube and means for transmitting the pH data to an implanted control unit. In another embodiment, the stimulator comprises electrodes implanted in the LES that are wired to an implantable IPG, which is in data communication with a pH measuring element, such as but not limited to a pH capsule or a catheter based device, that is transmitting pH data to the device via uni-directional or bi-directional communication.

In another embodiment, the stimulator/sensing system disclosed herein can locally store a plurality of programmatic instructions that, when executed by circuitry within the IPG, uses data received from a capsule to automatically refine stimulation parameters within a pre-defined range of boundaries. The data may be continuously streamed from the sensing capsule to the IPG and may be subject to continuous monitoring and processing. The data may comprise any one of pH data, gastric pressure data, LES pressure data, temperature, impedance, incline, or other physiological data.

Figure 14:
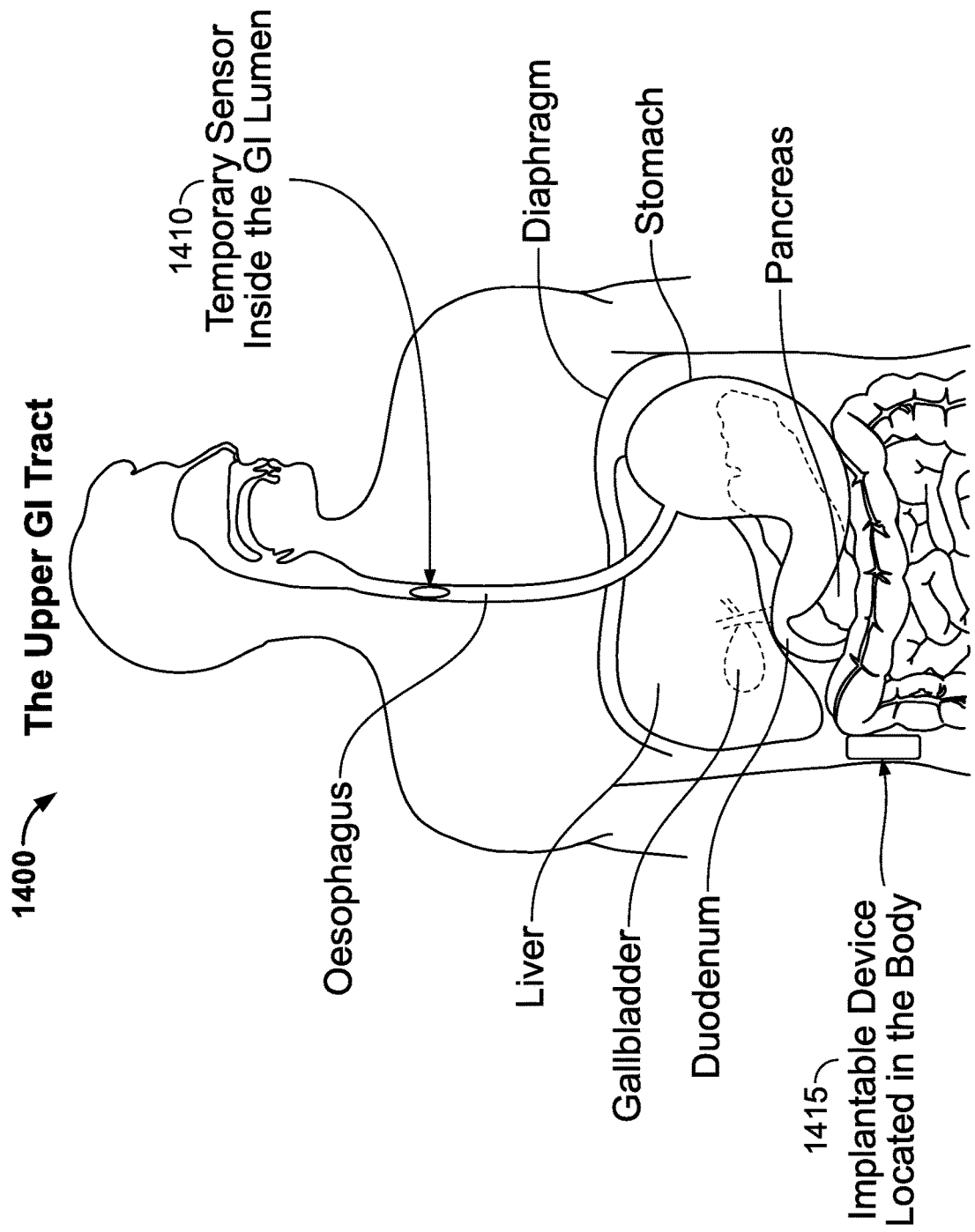
FIG. 14 is a cross-sectional illustration of the upper gastrointestinal tract showing a pH sensing capsule in the esophagus and a stimulator adapted to be implanted within the tissue of the patient.

Referring to FIG. 14, a patient 1400 has implanted within his tissue a stimulator 1415, as further described below. The stimulator 1415 is adapted to dynamically communicate with a temporary sensor 1410, as further described below, which may be located inside the patient's GI lumen. The implanted stimulator 1415 comprises stimulator circuitry and memory having programmatic instructions that, when executed, perform the following functions: transmit an interrogating signal designed to elicit or cause a transmission of sensed data from the temporary sensor 1410 or receive a transmitted signal comprising sensed data from the temporary sensor 1415 and process the sensed data to modify stimulation parameters, such as frequency, duration, amplitude, or timing. Optionally, the stimulator 1415 may also analyze the received sensed data signal to determine if the data is reliable. The implanted stimulator 1415 is adapted to only modify stimulation parameters or otherwise engage in a processing routine adapted to use the sensed data to determine how the simulation parameters should be modified when it senses and receives the sensed data. Optionally, the implanted stimulator 1415 is adapted to modify stimulation parameters or otherwise engage in a processing routine adapted to use the sensed data in combination with patient data inputted into an external device to determine how the simulation parameters should be modified.

For example, where a meal event, sleeping event, or other event which may cause, be related to, or be associated with a GERD event, is expected to occur at a specific time during the day (either because previously sensed data has determined a pattern indicating the existence of such an event or because patient data expressly indicates that such an event should be expected), stimulation parameters may be modified or otherwise established in order to provide the requisite level, degree or amount of stimulation before the anticipated event, such as 5 minutes, 10 minutes, 30 minutes, 45 minutes, 60 minutes, 90 minutes, 120 minutes, or some increment therein. The determination of stimulation parameters, including start time, end time, pulse frequency, duration, ramp rate, duty cycle, and/or amplitude, can be determined independent of the patient's immediate physiological state and not causally related to the patient's existing condition. Rather, historical data patterns from sensors, including LES high pressure zone length data, gastric pressure data, LES pressure data, temperature, impedance, incline, or other physiological data, can be used to define the GERD profile of a patient, namely when, in the course of a day, a patient is likely to experience a GERD event, and then used to proactively normalize LES function in advance of the GERD event. To properly generate and mine data patterns, it is preferable to capture both the magnitude of the physiological data (i.e. pH<4), the duration (for one hour), and the timing (around 1 pm). It is further preferable to associate different physiological data with each other to see if a predictive pattern may exist between data sets and to further correlate that data with the patient's own reporting of pain, discomfort, acid reflux, or other sensations to better determine when a GERD event is likely to occur in a day.

In one embodiment, the implanted stimulator 1415 is configured to check the reliability of the data by processing it to determine whether the data is indicative of the sensor being in an improper location. In one embodiment, wherein the temporary sensor is a capsule measuring pH data intended to measure esophageal pH, such a determination process may be conducted by: a) monitoring the received pH data over a predefined period of time to determine if it is indicative of a high pH environment, such as the patient's stomach as opposed to the esophagus, b) monitoring the received data signal, such as an RF signal, over a predefined period of time to determine if the signal strength has significantly changed or modified, indicating a change in physical location, or c) monitoring a received accelerometer or inclinometer data signal from the pH capsule, over a predefined period of time, to determine if the capsule is in a proper physical orientation. Depending on the reliability check, the implanted stimulator 1415 may use, or discard, the sensed data. If no reliable data is received by the implanted stimulator 1415, it does not modify stimulation parameters or otherwise engage in a processing routine adapted to use the sensed data to determine how the simulation parameters should be modified. If reliable data is received by the implanted stimulator 1415, it modifies stimulation parameters or otherwise engages in a processing routine adapted to use the sensed data to determine how the simulation parameters should be modified.

In one embodiment, the temporary sensor 1402 stores the sensed and transmitted data and transmits the stored data to an external reading device. It should be appreciated that the previously discussed methods for using sensed data, whether from a temporary sensor or permanently implanted sensor, may be performed by an external device. For example, in one embodiment, an external device wirelessly receives sensed data and uses the sensed data to determine a pattern indicative of when a GERD event is likely to be experienced by a patient. Any pattern analysis method known to persons of ordinary skill in the art may be used. The data may include some or all of the sense data, externally inputted patient data, or a combination thereof. As discussed above, the external device would use the data to determine the time(s) of day when a patient typically experiences a GERD event and the appropriate stimulation parameters required to normalize LES function prior to such event. In one embodiment, the requisite stimulation parameters are determined by examining historical GERD events in relation to stimulation parameters that had been implemented and modifying the stimulation parameters to increase or decrease the magnitude or duration of the stimulation accordingly. Additionally, in one embodiment, the implanted stimulator 1415 stores the sensed data and data indicative of how stimulation parameters, such as frequency, duration, amplitude, or timing, were modified based on the sensed data, and transmits the stored data to an external reading device.

Figure 15:
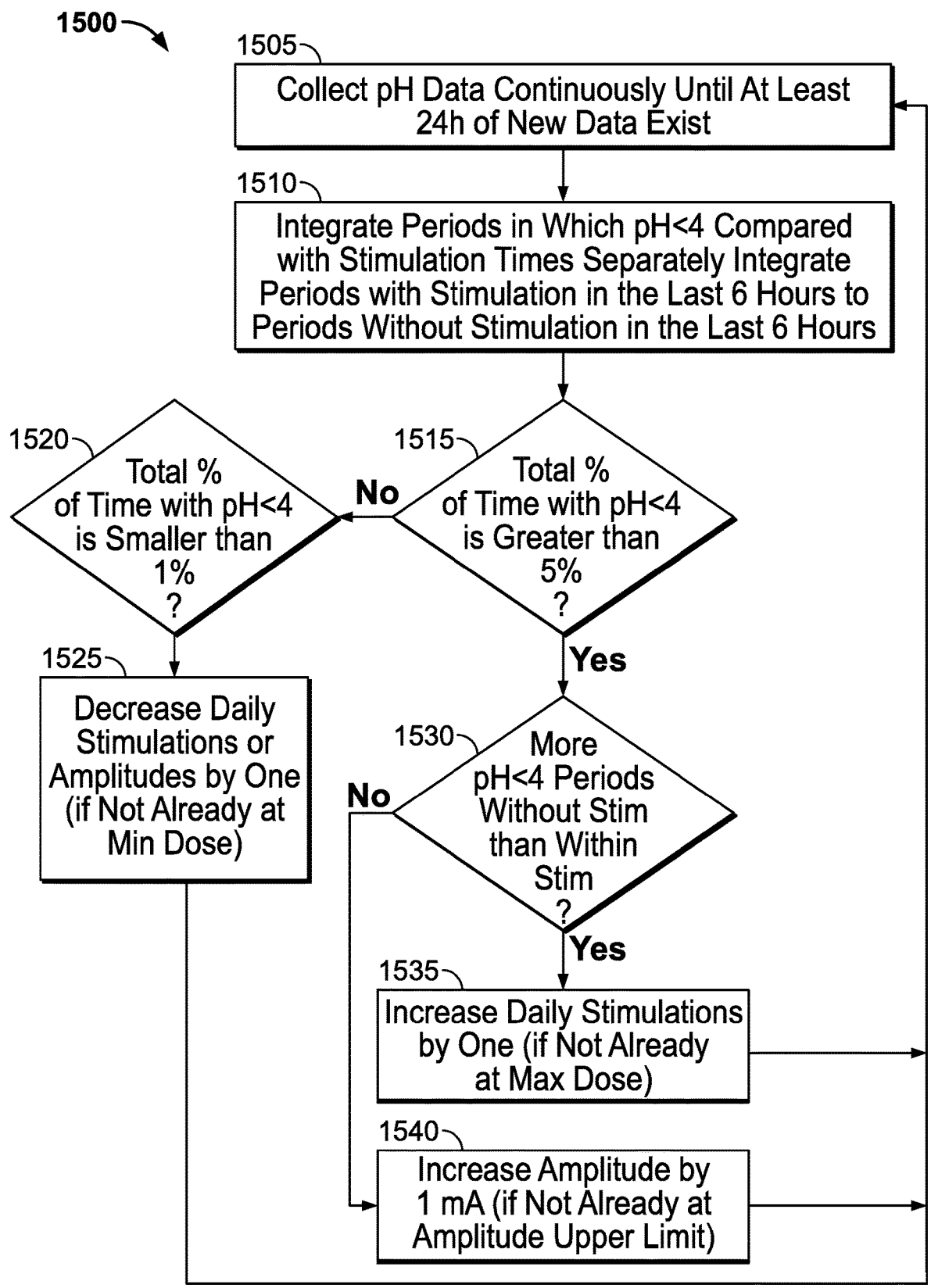
FIG. 15 is a flow chart depicting a certain parameter setting method of one embodiment of the present specification.

Referring to FIG. 15, in one embodiment, the process 1500 implemented by the stimulator system comprises collecting 1505 pH data periodically or continuously over a predefined period, such as 1, 2, 6, 12, 24, 36, 48, or 60 hours, or any time increment in between. Circuitry within the stimulator analyzes the pH data 1510 to determine if, within the predefined period, such as 24 hours, pH is less than a predefined value, such as 4, for a percentage of time higher than a threshold value, such as 1, 2, 3, 4, 5, 10, 15, or 20 hours, or any increment therein 1515. The processor may analyze pH data 1510 by integrating periods in which the pH is less than the predefined value compared with stimulation times and separately integrate periods with stimulation in a most recent time period (i.e. last 6 hours) to periods without stimulation in the most recent time period.

If the percentage of time with the pH less than the predefined value within a predefined period is lower than a threshold value, such as 1 percent or lower 1520, then the circuitry may adjust stimulation parameters 1525 so as to reduce the timing, frequency, or size of the stimulation doses. In one embodiment, the circuitry decreases daily stimulations or amplitudes by a discrete amount, such as 1 mAmp. In one embodiment, the system may not reduce the timing, frequency, or size of the stimulation doses below a minimum dose.

If the percentage of time with the pH less than the predefined value within a predefined period is greater than a threshold value, such as 5 percent or higher 1515, then the circuitry may further analyze 1530 whether there were more periods with pH being greater than the threshold value during which there was no stimulation than with stimulation. If there were more periods with pH being greater than the threshold value during which there was no stimulation than with stimulation, the circuitry may increase the number of daily stimulations by a discrete amount, such as by 1 1535 or the duty cycle or length of a given stimulation session or duration by a discrete amount, such as 1 minute. By doing so, the system assumes the amount of energy delivered per stimulation is sufficient, but there simply were not enough stimulation events in a day, or the stimulation was not long enough. If there were more periods with pH being greater than the threshold value during which there was stimulation than with no stimulation, the circuitry increases the amplitudes of stimulations by a discrete amount, such as by 1 mAmp 1540. By doing so, the system assumes the amount of energy delivered per stimulation was not sufficient and therefore increases the energy delivered per stimulation. In one embodiment, the system may not increase the timing, frequency, or size of the stimulation doses above a maximum dose.

In general, if the percentage of time within a predefined period during which pH is less than a threshold value, such as 4, is higher than an upper value, such as 5%, then the stimulation parameters will be adjusted so as to increase dose. Also, if the percentage of time within a predefined period during which pH is less than a threshold value, such as 4, is lower than a lower value, such as 1%, then the stimulation parameters may be adjusted so as to reduce dose. The decreasing and increasing of dose will be done based on the temporal behavior of the pH values. It should be appreciated that doses may be incremented by any amount. It should further be appreciated that doses can be effectively decreased or increased by increasing one parameter while reducing another parameter so that the total energy is increased, reduced, or unchanged. Finally, it should be appreciated that all modifiable parameters will be bounded, on at least one of the maximum or minimum boundary, by a range defined by a healthcare provider.

In another embodiment, the operation of the system is augmented with other sensed data. Where the system is being used to stimulate the LES or fundus or to treat GERD, pH sensor data can be augmented with accelerometer and/or inclinometer data. The accelerometer or inclinometer sensor (s) could be located within the implantable device or in another device on or inside the patient body. This additional data can enable the control unit algorithm to assess patient modes (e.g., sleep, exercise, etc) and thereby to improve the tuning of stimulation parameters for a specific patient, thereby improving device efficacy and/or efficiency. Additional sources of information may include, but not be limited to, pressure measurement or an impedance measurement by a capsule or an eating detection mechanism using one or more sources such as impedance or other electrical or electromechanical measurement from within the tissue or from the lumen. These additional sources of information can further be used by the control unit to adjust the stimulation dose and other parameters and other functions of the implantable device. It should be appreciated that any of the aforementioned data may be used individually or in combination to modify the operation of the system and, in particular, to determine how stimulation parameters should be modified to address an anticipated patient GERD event.

In one embodiment, the system logs the sensed and computed data and downloads the data to an external device for viewing and analyzing by a medical professional or a technician. By permitting on-demand or batch downloading, the system can eliminate the need for the patient to carry an external receiver during pH-sensing, thereby improving the use experience of the patient and potentially improving compliance and allowing for longer measurement periods. The system can download data automatically and without any requirement for user intervention, such as when an appropriately calibrated external device comes within a data communication area of the implanted device, or semi-automatically, such as when initiated by the implantable device when the implantable device is in proximity (communication distance) of the external device and the user has provided a password or other indication of approval via the external wireless interrogation device.

It should be appreciated that the external device receiving the sensed or computed data could be located at the healthcare provider's location or at the patient's home. If captured at the patient's home, the data could be automatically sent to the clinic for physician review and/or approval of suggested parameter changes via any communication medium, including Internet, Ethernet network, PSTN telephony, cellular, Bluetooth, 802.11, or other forms of wired or wireless communication. The transmitted data preferably contain the measured values, the recommended stimulation parameters adjustments, or both. Similarly, the physician approval, or physician suggested parameter changes, could be sent back to the external device located at the patient's home which, in turn, transmits appropriate commands to the implanted device, when the two devices are in proximity, to initiate the suggested parameter changes.

In another embodiment, the system monitors sensor, such as capsule, failure. If the sensor fails an internal diagnostic test, a failure or alert signal is transmitted to the implanted control unit, or the implanted control unit itself logs a failed attempt to communicate with, or obtain uncorrupted data from, the sensor. The control unit then transmits that failure or alert signal data to the external device and, in turn, to the healthcare provider, as described above, thereby alerting a healthcare provider that the patient needs to return to have the sensor fixed or another sensor implanted.

In another embodiment, the system is capable of recognizing and registering a plurality of different sensing devices, such as capsules, and re-initiate newly implanted sensors as required to ensure continuous or substantially continuous measurement. For example, the stimulator can be implanted for a long period of time, such as several months or years, and for a shorter period of time, such as once per annum, a sensor is implanted. The stimulator registers the new sensor and automatically adjusts the new sensor for operation in the particular anatomical region, such as the esophagus.

In addition to failing, sensors may migrate out of the implanted anatomical region. For example, where a sensor, such as a capsule, has been implanted into a patient's esophagus but has migrated to the stomach, the physical location of the sensor can be derived by examining the sensed data. For example, where a pH capsule has moved from the esophagus to the stomach, the capsule will likely transmit data indicative of extensively long periods during which the pH is highly acidic. In that case, the stimulator system can assume the capsule has migrated, report this failure to an external device, and ignore future data being transmitted from the capsule or record the data but not rely upon it for parameter setting. Similarly, the stimulation system may register a weaker or changed signal, indicative of a sensor moving a distance away from the recording device.

The presently disclosed stimulator system may further comprise a receiving antenna integrated into a stimulator system, which may be used for energy transfer to the stimulator system and communication to and from the device. The close proximity between the stimulator, particularly a miniature device, and a sensor, such as the pH capsule, can be used to achieve communication efficiency and increase durability through a miniature antenna in the stimulator that can accept data from the pH capsule. The close distance can effectively reduce power requirements and enables typical low frequency inductively coupled telemetry for transmission through titanium via coils; as well as high frequency RF communication such as MICS or IMS bands via monopole, dipole, or fractal electric field antennas. The communication distance can be further reduced by enabling anchoring of the pH capsule or nasogastric tube to the implanted control unit. This can be facilitated by, for example, a magnetic force between the two units caused by a magnet in both units or a magnet in one unit and a ferrous metal in the other.

One of ordinary skill in the art would appreciate that other means for communication can be used that will take advantage of the close proximity between the stimulating electrodes and the sensing device, such as a pH capsule, even when the control unit is farther away, thereby allowing for a significant reduction in the power consumption and improvement of reliability of communication. The stimulating electrodes in that embodiment would serve as receiving antennas and also simplify the design of the control unit, thereby avoiding the need for a receiving coil, antenna or other electromagnetic receiving means.

Bi-directional communication between the control unit and the sensor unit can be implemented as part of the system to allow, for example, calibration or activation of specific actions such as additional measurements, determination of measurements to be taken, determination of measurement times, local stimulation by the sensor unit, among other variables. The sensor unit can also be used to not only transmit the sensed data, but also to transmit energy for charging and powering the control unit and the stimulating device. For example, pH capsules that further acts as an energy recharging source can be periodically implanted, as required, to deliver energy to the control unit or a microstimulator in addition to actually sensing pH data.

Patient Selection Methods

In one embodiment, a person is permitted to practice the treatment systems and methods disclosed herein and, in particular, to have an embodiment of the electrical stimulation systems disclosed herein implanted into him or her only if the person passes a plurality of screening or filtering steps.

In one embodiment, a plurality of physiological measurements are taken of the patient and used to determine whether the patient may therapeutically benefit from the electrical stimulation treatment systems and methods disclosed herein. LES high pressure zone length data, LES pressure data, gastric pressure data, and/or pH data is collected from the patient. For example, pH measurements are obtained over a period of time, such as 4, 8, 12, 16, 20, or 24 hours or some increment therein. The amount of time within the predefined measurement period during which the pH measurement is above a predefined threshold indicative of acid exposure, such as a pH of 4, is calculated. The number of acid exposure events occurring for more than a predefined period of time, such as more than 1, 3, 10, 15, or 20 minutes, or any increment therein, is determined. The total time for each acid exposure event lasting more than the predefined period of time, i.e. 3 minutes, referred to as a long event, is then summed. If that total time exceeds a predefined threshold, such as 5 minutes to 240 minutes or any increment therein, it may be concluded that the patient would therapeutically benefit from the electrical stimulation treatment systems and methods disclosed herein. For example, if a patient has 4 events of acid exposure lasting 1, 4, 5 and 6 minutes and the predefined threshold is 3 minutes, the total time would be equal to 15 minutes (4+5+6). If the total time threshold is 10 minutes, then the patient can be categorized as an individual who would benefit from the electrical stimulation treatment systems and methods disclosed herein.

Another physiological measurement that may be used to select eligible patients is LES end expiratory pressure (LES-EEP). In one embodiment, a patient's LES-EEP is measured and collected during resting time, e.g. no swallow for at least 30 seconds, and then compared to at least one threshold. For example, the value of the LES-EEP should be below a normal value threshold, such as 10-20 mmHg, preferably 12-18 mmHg, and more preferably 15 mmHg, in order for the patient to qualify for treatment. In another embodiment, a patient's LES-EEP is measured and collected during resting time, e.g. no swallow for at least 30 seconds, and then compared to a range of pressure values, e.g. to two different threshold values. For example, the value of the LES-EEP should be above a lower threshold, which is indicative of the LES having some base functionality, such as 0 mmHg to 3 mmHg or any increment therein and below an upper threshold, such as 8 mmHg to 10 mmHg or any increment therein.

Another physiological measurement that may be used to select eligible patients is the rate of transient LES relaxation events (tLESR). Patients with higher rates of tLESRs which constitute a portion of their acid exposure time above a predefined threshold may benefit less from treatment than patients with lower rates of tLESRs constituting a portion of their acid exposure time above a predefined threshold. In one embodiment, a patient's tLESR rate is determined over a period of time, such as 24 hours or less. The tLESR rate is determined by recording the number and duration of acid exposure events, as described above, and then calculating the number of acid exposure events shorter than a predefined time period, such as shorter a total time threshold, as defined above, shorter than 5 minutes, shorter than 10 seconds or shorter than any increment therein, generally referred to as a short event. The number of such short events per period is then compared to an inclusion threshold, such as a range of 3-50, preferably 5-20. If the number of short events is below the range, the patient may not qualify for treatment or may qualify for a different stimulation regimen that can be programmed into the stimulator.

In another embodiment, a patient's acid exposure times are recorded and then compared to the timing of patient's reported reflux symptoms. The degree of temporal correlation between the acid exposure times and reported symptoms is then determined. Patients with a degree of correlation above a predefined threshold would be eligible for treatment while those below the predefined threshold would not be.

In another embodiment, it is determined whether a patient may therapeutically benefit from the electrical stimulation treatment systems and methods disclosed herein by temporarily stimulating the patient for a period of time, such as less than one week, using a non-permanent implanted stimulator to evaluate the patient's physiological response to stimulation and predict the patient's likely physiological response to a permanent stimulator. In one embodiment, the temporary stimulation is delivered using a temporary pacing lead endoscopically implanted in the patient's LES and connected to an external stimulator, which is either a non-portable system or a portable battery-operated device. The temporary stimulation system delivers periodic stimulations over a period of time, from 30 minutes to two weeks or more, during which the patient's symptoms, acid exposure events, and physiological response are recorded and correlations between the three are determined. The temporary stimulation data can then be used to determine the likely timings of GERD events and the required stimulation parameters to proactively normalize the patient's LES in advance of the GERD events, as previously discussed. Once the temporary stimulation period is complete, the electrode can be removed and a decision can be made regarding whether the patient would therapeutically benefit from a permanent implant based, for example, on the patient's physiological response to the temporary stimulation, improvement in symptoms, normalization of pH levels, normalization or increase in LES high pressure zone length, decrease in gastric pressure, and/or normalization of LES pressure.

In one embodiment, the temporary stimulator is in the shape of a small capsule-like device that is self-contained and includes all required components for stimulation including a power source or a receiver that allows power to be received wirelessly from outside the body and one or more electrodes. The device is adapted to stimulate the LES or gastric tissue. The device also includes an anchoring component, such as a hook, corkscrew, rivet, or any other such mechanism, which temporarily connects it to the LES or gastric wall. The capsule is implanted through an endoscopic or catheterization procedure to the LES or gastric wall. Such a capsule is expected to remain attached to the LES or gastric wall for a period of one day to two weeks or longer and then detach by itself and leave the body naturally. Further the device can include a sensor for detecting when it is attached to the wall, which will only stimulate when it detects that the device is still attached to the LES or gastric wall. Additionally the device may include wireless communication to allow telemetry and/or commands to be delivered from outside the body. The capsule can additionally include pH measurement, manometry measurement or other physiological measurement devices or sensors so that the short term efficacy of the stimulation can be more easily evaluated. Additional standard measurements can be made as needed for obtaining more information.

It should be appreciated that any form of temporary stimulator could be used. For example, a stimulator can include a) a plurality of implantable leads adapted to be temporarily implanted into the LES or gastric tissue through endoscopy, laparoscopy or other minimally invasive methods and further adapted to deliver stimulation to the LES or gastric fundus, b) a housing which includes a control unit and circuitry for generating electrical stimulation where the housing is adapted to be temporarily implantable and/or be integrated with the leads such that the housing itself can deliver stimulation or externally located and wired to the leads without being implantable and/or c) an additional unit capable of recording the physiological data, stimulation data, and various patient inputs (symptoms, eating, sleeping events, etc.) and adapted to be used for turning stimulation on or off. Optionally, the additional unit is controlled by a physician and wirelessly programmable using a physician's computer system. Optionally, the stimulator can also be configured to include sensors or communicate with sensors that measure the aforementioned physiological measures.

Other approaches for selecting patients based on physiological data and/or temporary stimulation can also be implemented. It should be clear to person skilled in the art that the above selection methods could be integrated in various ways to result in an optimal selection of patients. For example one integrated method can be used to screen patients by qualifying candidates according to pH long events, the manometry value of LES-EEP, or the number of short events, or any combination thereof. Additionally, a combination of the measures can be used such as dividing the total length of long events by the rate of short events and comparing this value against a properly adjusted threshold, such that patients with a ratio above the threshold are included and others are excluded. Once qualified, the patient can undergo the permanent implant procedure or undergo the temporary stimulation process to further qualify the patient.

Physician Diagnostic and Programming Systems and Methods

Different patients may require different therapeutic regimens, depending upon implant depth, anatomical variations, treatment objectives, and severity of the disease condition. Each patient has a different baseline LES high pressure zone length and baseline gastric pressure and different responses to stimulation (due to expected variability in sphincter and gastric muscle condition and also in the implant location). Furthermore, changes to the patient's anatomy, for example arising from normal healing after implantation, chronic stimulation or age, can also change the optimal stimulation dosage. Accordingly, it is preferred for a patient to first undergo a diagnostic process to determine whether, and to what extent, the patient can be treated by one of a plurality of therapeutic processes, as further described below. It is also preferred for a patient to periodically visit a physician to have the efficacy of the stimulation system checked, optimized, and possibly reprogrammed, as provided below.

In one embodiment, because the goal is to keep the stomach at a gastric pressure or function which eliminates or greatly reduces the chances for acid exposure, it is unnecessary for the muscle to always have low pressure but, rather, it is desirable to have (1) some average pressure sustained at all times with a certain permitted range of variability around it and a maximum pressure that the stomach will never be, or will rarely be, above or (2) some average function sustained at all times with a certain permitted range of variability around it and a minimal function that the LES will never be, or will rarely be, below or a combination thereof. Continuous non-stop stimulation is not optimal because the acute response of enhanced pressure may diminish over time due to neuromuscular tolerance or muscle fatigue. Furthermore, a simple "on-off" regime during which the muscle is stimulated for a first duration and then the stimulation is turned off for a second duration may be effective; however, different muscle properties, variations in the patient condition, and variations in the implant may require a different selection of the "on" and "off" periods for each patient and may also require a change in the initial selection of the "on" and "off" periods over time in the same patient.

In one embodiment, a patient's average functional LES pressure (AP) and minimal functional LES pressure (MP) is set by conducting a parameter setting test, in which a stimulator is controlled by an operator and manometry measurements of LES and gastric pressures are made. During this test, the operator turns on the stimulation and then observes the functional LES pressure while keeping the stimulation on until the functional LES pressure crosses a first threshold, defined, for example, by AP+(AP-MP). When the observed pressure passes this first threshold, the stimulation is either turned off or kept on for an additional short period of up to 5 minutes and then turned off. The operator notes the time when the stimulation is turned off.

The operator continues to observe the pressure and once the pressure reaches MP, the operator turns on the stimulation again and notes the time. This measurement process continues for several hours, such as 2 to 5 hours, so that several stimulation on-off periods can be recorded. At the end of the test period, a chronic "on" time is selected to be the median of the measured "on" periods and a chronic "off" period is selected to be the median of the measured "off" periods. It should be appreciated that the initiation of stimulation, turning off of stimulation, recordation of time periods, and recordation of functional LES pressure can be performed automatically, based on a pre-programmed set of threshold values, by a computing device comprising a processor and memory storing the threshold and control instructions as a set of programmatic instructions.

In another embodiment, a patient's average functional LES pressure (AP) and minimal functional LES pressure (MP) is set by conducting a parameter setting test, in which a stimulator is controlled by an operator and manometry measurements of LES and gastric pressures are made. During this test, the operator turns on the stimulation, notes the electrode impedance value, and then observes the functional LES pressure while keeping the stimulation on until the pressure crosses a first threshold, defined, for example, by AP+(AP-MP). When the observed pressure passes this first threshold, the stimulation is either turned off or kept on for an additional short period of up to 5 minutes and then turned off. The operator notes the time when the stimulation is turned off and the electrode impedance value when the stimulation is turned off.

The operator continues to observe the pressure and once the pressure reaches MP, the operator turns on the stimulation again and notes the time and electrode impedance value. This measurement process continues for several hours, such as 2 to 5 hours, so that several stimulation on-off periods can be recorded. Electrode impedance is measured every time the stimulation is turned "on" or "off". At the end of the test period, a chronic "on" time is selected to be the median of the measured impedance value for the "on" periods and a chronic "off" period is selected to be the median of the measured impedance value for the "off" periods. Rather than setting a stimulation device to operate based on fixed time periods, a stimulation device is programmed to turn off and on based upon the measured impedance values, where the device turns on when a patient's impedance value approaches the measured mean, median, or any other calculated impedance value for the on periods and turns off when a patient's impedance value approaches the measured median, mean, or any other calculated impedance value for the off periods. It should be appreciated that the initiation of stimulation, turning off of stimulation, recordation of time periods, recordation of electrode impedance, and recordation of functional LES pressure can be performed automatically, based on a pre-programmed set of threshold values, by a computing device comprising a processor and memory storing the threshold and control instructions as a set of programmatic instructions. It should be appreciated that, in addition to the above embodiments, a patient's functional LES pressure may be recorded by conducting a parameter setting test, in which a stimulator is controlled by an operator and manometry measurements of LES and gastric pressures are made. The recorded functional LES pressures are compared to a predefined threshold to determine a maximum pressure which should preferably not be exceeded. The aforementioned on and off periods are then set or modified based on this maximum pressure data.

It should be appreciated that the use of impedance values is useful, relative to manometry measurements, if the values of the "on" and "off" periods in the acute phase do not converge to a small range within a few minutes. It should further be appreciated that other measurements, instead of impedance, can be used, including physical tension sensors (i.e. implantable strain gauge) or sensors of the muscle electrical activity or sensor of muscle pressure. Furthermore, it should be appreciated that both of the aforementioned tests can be used, and/or combined, to fix time windows for the "on" and "off" periods and rely on impedance measurements in order to adapt, modify, or change the time windows to account for a possible drift in muscle status In another embodiment, a doctor makes a determination regarding the LES or fundus electrical stimulation therapy (EST) available to a patient by first engaging in a process for evaluating a plurality of appropriate dosing values for a patient. The evaluation process comprises subjecting a patient to a plurality of pulse sequences and measuring the corresponding LES pressure and gastric pressures.

TABLE 4

| Phase # | Electrical Stimulation Type | Pulse Frequency | Pulse Duration | Pulse Amplitude |
| --- | --- | --- | --- | --- |
| 1 | Short Pulse | 20 Hz | 200 μsec | 5 mAmp |
| 2 If #1 reaches ≥20 mmHg | Short Pulse | 20 Hz | 200 μsec | 3 mAmp |
| 3 If #1 does not reach ≥20 mmHg | Short Pulse | 20 Hz | 200 μsec | 7 mAmp |
| 4 If #3 does not reach ≥20 mmHg | Short Pulse | 20 Hz | 200 μsec | 10-15 mAmp |
| 5 | Intermediate Pulse | 20 Hz | 3 ms | 3-15 mAmp using the same sequence as 1-4 |
| 6 | Optimal Pulse | 20 Hz | Optimal Pulse | Optimal amplitude |

As shown above, each of phases 1-4 is applied for 20-30 minutes with a 20-30 minute interval between sessions. The pulse increments can range from 0.1 mAmp to 15 mAmp. The pulse in Phase 6 is intermittently applied for 5 hours, during which stimulation is turned on until pressure is greater than or equal to 20 mmHg for at least 5 minutes (on period) and then turned off until pressure drops to less than 10 mmHg or patient's baseline whichever is higher (off period), and then turned on again until it is greater than or equal to 20 mmHg again (on period), repeating thereafter. These on-off sessions continue while the time durations are recorded. These recorded periods are then used to determine the optimal duty cycle for the patient during the treatment phase (patient-specific EST). It should be appreciated that, if a subject experiences pain or discomfort for any given stimulation sequence, the pulse amplitude is decreased in 1 mAmp increments until stimulation is tolerable. Once the effective tolerable setting is established, the patient-specific EST is initiated with the defined stimulation parameters, as determined by the parameter setting stage described above. Preferably, the patient-specific EST is checked at a set schedule (every 6 months or once a year) or when a patient starts reporting GERD symptoms using manometry and the patient-specific EST parameters are then modified to achieve ideal LES and/or gastric pressures.

It should be appreciated that the aforementioned diagnostic processes account for a plurality of variables that substantially affect treatment quality, treatment efficacy, and patient compliance, including, but not limited to, patient's disease condition and the corresponding stimulation energy level and frequency required to achieve a positive therapeutic effect, patient willingness to manually apply stimulation, and form factor of the stimulation source, among other variables.

The variables generated in the course of the diagnostic processes can be used to automatically program a controller, which may be used to control a stimulator. In one embodiment, a diagnostic terminal executing on a conventional computer generates at least one variable, such as stimulation pulse width, frequency, amplitude, ramp rate, or a duty cycle, that substantially affects treatment quality, treatment efficacy, and patient compliance, including, but not limited to, patient's disease condition and the corresponding stimulation energy level and frequency required to achieve a positive therapeutic effect, patient willingness to manually apply stimulation, and form factor of the stimulation source, among other variables. The diagnostic terminal is in data communication with a controller configuration terminal that electronically receives a controller into an interface or wirelessly communicates with the controller that is responsible for executing the stimulation parameters. Upon generating the variables, the diagnostic terminal transmits the variables, which are eventually received by the controller and saved in an appropriate memory location. The controller then uses the variables to control one or more stimulation settings.

In another embodiment, the stimulation parameters are checked by a physician using a data terminal, such as a laptop, tablet computer, mobile device, or personal computer. As discussed above, data relevant to the efficacy of the stimulation parameters can be wirelessly obtained from the stimulation device memory or from a patient controlled computing device, such as a tablet computer, laptop, personal computer, or mobile device. The physician can modify the stimulation parameters in accordance with the received data and, using the data terminal, issue modified stimulation parameters to the controller of a stimulator as described above.

Exemplary Therapies

The following description is intended to provide examples of how the therapies, described above, may be specifically implemented. They should not be viewed as limiting the general scope of the inventions described herein.

Therapy One: Patient Timed and Delivered Stimulation Using a Handheld Device

In a first therapy, a patient can be effectively therapeutically treated with intermittent wireless short bursts of stimulation applied a plurality of times during a day. For example, in one embodiment, a patient can be treated by applying a burst of stimulation for a period of five minutes or less at a frequency of 5 times or less per day. In another embodiment, the stimulation occurs less than 5 times a day for a period of 30 minutes or less per stimulation. This stimulation frequency is effective to treat certain symptoms of a patient, including diminishing or eliminating a patient's GERD.

Figure 16:
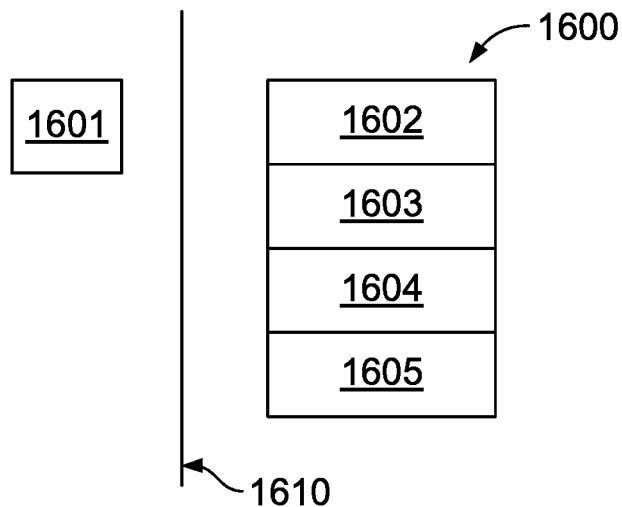
FIG. 16 is a block diagram depicting the modules of an exemplary embodiment of the stimulating device of the present specification.

In this treatment method, a patient can be effectively treated by having the patient apply an external power source over a predefined area on the patient's body and manually initiate stimulation. FIG. 16 is one embodiment of a block diagram of certain modules of a stimulating device of the present specification. In one embodiment, the stimulation system comprises a stimulation source 1600 and a microstimulator 1601. The stimulation source 1600 comprises a controller 1602, transducer 1603, waveform generator 1604, and power source 1605, such as a battery. The stimulation source 1600 directs energy, such as ultrasound or RF energy, across the patient's skin 1610 and toward a microstimulator 1601 that is implanted directly on the site being stimulated. The stimulation source 1600 can generate a plurality of different pulse widths, amplitudes, frequencies, or combinations thereof, as further described below.

In certain situations, the device may require an energy supply to power the implantable pulse generator, but it is difficult or undesirable to include an implantable battery that would be wired to the device due to size limitations, restrictions arising from the implant location, or the need to decrease device costs. In one embodiment, a rechargeable battery is wired to the stimulator. The rechargeable battery stores a smaller amount of charge, and therefore can be small in size, but is configured or adapted to be replenished using wireless transmission of energy.

In another embodiment that requires an implanted device size which is even smaller than that which is possible with a rechargeable battery and associated recharging circuit, the device comprises a passive circuit that receives, in real time, transmitted wireless energy from a transmission source external to the patient. The implanted passive circuit would control the extraction of the transmitted energy and the delivery of the energy to the rest of the stimulator device. The external energy transmission device would control the timing of stimulation and any sensing and/or triggering mechanisms related thereto. One limitation to the wireless transmission of energy is the amount of energy that can be wirelessly transmitted in any given time due to, for example, safety or interference requirements. Such wireless energy transmission limitations narrow the applicable stimulation amplitude and waveform that can be applied to the tissue, thereby limiting the clinical application and benefit of such systems.

In another embodiment, the microstimulator comprises a means for storing a charge locally, such as a short-term energy storage component or a capacitor, and an associated trigger mechanism. During an on-off duty cycle for stimulating the microstimulator, the off-time of the stimulation duty cycle can be used to temporarily store a charge, thereby enhancing the maximal amplitude and variety of waveform that can be applied. The implanted device circuit is configured to control and time the stimulation in response to energy or control information from a controller that is external to the patient and communicates wirelessly with the implanted device. The implanted circuit extracts the transmitted energy or control information and, in response thereto, shapes the waveform within the off-time of each stimulation cycle using components such as capacitors, diodes, inductors, transistors and resistors.

The operating characteristics of a capacitor integrated with, or local to, the implanted device will be determined, at least in part, by the required pulse duration and the ratio of required stimulation pulse amplitude to minimal expected extracted supply current within the implantable device. The capacitor characteristics will also be a function of the load impedance. For example, assuming a required pulse duration of 200 μs to be applied every 50 ms and a required amplitude of 10 mAmp, the device will need to provide a charge of 2 μC (10 mAmp×200 μs). Assuming an impedance of 100 ohms with a voltage of 1 V (10 mAmp×100 ohm), then the minimum required capacitor will have a value as approximated by the following equation:

$$C=Q/V=2 \text{ uC}/1 \text{ V}=2 \text{ uF}$$

This value will need to be adjusted so that it is not fully discharged during stimulation and to compensate for losses within the implantable device. For an overall cycle of, for example, 50 ms, the theoretical minimal extracted supply current that can drive the required pulse will be:

$$\text{Minimal extracted current}=10 \text{ mAmp}\times200 \text{ μs}/(50 \text{ ms}-200 \text{ μs})=0.04 \text{ mAmp}$$

Adjusting for internal losses within the stimulator will yield a practical limit of about 0.1 mAmp or 100 μAmp. Higher available supply currents can allow for shorter cycles or longer pulse duration as necessary and can be extrapolated from the above.

In one embodiment, energy need not be stored between cycles and the passive circuit responds, in real-time, to the wireless transmission of energy. For example, the implanted circuit may initiate a stimulation pulse in response to a stimulation pulse wirelessly sent by the external energy transmitting unit, where the energy transmission is above a pre-defined time period, is characterized by the intermittent ceasing of energy transmission, or is characterized by another combination of "on"-"off" energy signals.

In one embodiment, the stimulation source 1600 directs ultrasonic energy to the microstimulator 1601 which comprises an ultrasonic receiver. The microstimulator 1601 is implanted into the area to be stimulated via an endoscope. The microstimulator 1601 can function either as a pass-through for energy and stimulation parameters or comprise an energy storage and programmatic memory to deliver short stimulation bursts, using the stored energy, at predetermined time intervals, pursuant to the programmed memory.

In one embodiment, the stimulation source 1600 directs radio frequency (RF) energy to the microstimulator 1601 which comprises an RF receiver. The microstimulator 1601 is implanted into the area to be stimulated via an endoscope. The microstimulator 1601 can function either as a pass-through for energy and stimulation parameters or comprise an energy storage and programmatic memory to deliver short stimulation bursts, using the stored energy, at predetermined time intervals, pursuant to the programmed memory.

In one embodiment, the stimulation source 1600 comprises a controller 1602, transducer 1603, waveform generator 1604, and power source 1605, such as a battery. Operationally, the controller 1602, via a processor in data communication with a memory storing programmatic instructions, causes the waveform generator 1604 to generate a predefined waveform, having an associated pulse width, amplitude, and frequency, which is transmitted via the transducer 1603 to the endoscopically implanted microstimulator 1601. A patient applies the stimulation source 1600 intermittently for a short time period, preferably 30 minutes or less, over the microstimulator 1601 site. Where the microstimulator 1601 comprises a local memory for storing programmatic instructions, in particular stimulation parameters and processes, the stimulation source 1600 need not comprise a controller and memory for storing such programmatic instructions and may simply transmit a predefined amount of energy to the microstimulator.

Figure 17:
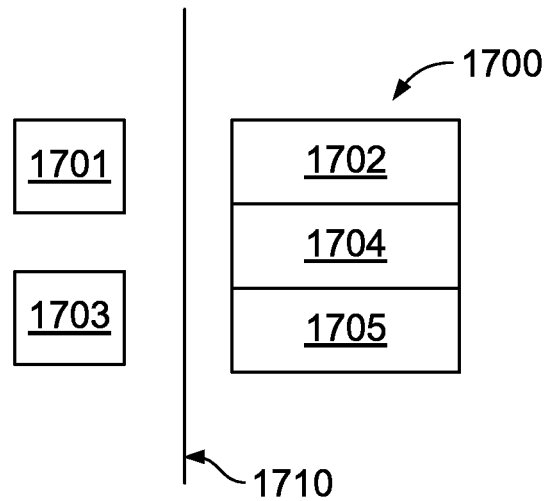
FIG. 17 is a block diagram depicting the modules of another exemplary embodiment of the stimulating device of the present specification.

In another embodiment, referring to FIG. 17, the stimulation source 1700 comprises a controller 1702, waveform generator 1704, and power source 1705, such as a battery. It wirelessly communicates with, and/or transfers energy to, a transducer 1703 that is implanted subcutaneously. The subcutaneous transducer 1703 receives the wirelessly transmitted energy, such as RF or ultrasound, through the patient's skin surface and transmits it, via a wired or wireless connection, to an endoscopically implanted microstimulator 1701. Operationally, the controller 1702, via a processor in data communication with a memory storing programmatic instructions, causes the waveform generator 1704 to generate a predefined waveform, having an associated pulse width, amplitude, and frequency, which is transmitted wirelessly into the patient's subcutaneous region and into the transducer 1703, which further transmits the energy to the microstimulator 1701. A patient applies the stimulation source 1700 intermittently for a short time period, preferably thirty minutes or less, over the transducer site. Where the microstimulator 1701 comprises a local memory for storing programmatic instructions, in particular stimulation parameters and processes, the stimulation source 1700 need not comprise a controller and memory for storing such programmatic instructions and may simply transmit a predefined amount of energy to the transducer 1703 and, thus, to the microstimulator 1701. It should be appreciated that, regardless of the type, the stimulation source 1700 can be integrated into a plurality of different housings, including a miniature flashlight, cell phone case, or smart card. In one embodiment, the subcutaneous transducer 1703 receives lower frequency electromagnetic energy and commands from the stimulation source 1700 and converts the energy into high frequency RF energy. The frequency conversion will be less efficient than direct RF transmission but the use of the subcutaneous transducer will assist in eliminating heating issues. In addition, the subcutaneous transducer can also be used as a simple energy storage unit. In another embodiment, the subcutaneous transducer 1703 receives lower frequency electromagnetic energy and commands from the stimulation source 1700 and converts the energy into ultrasound energy.

Figure 18:
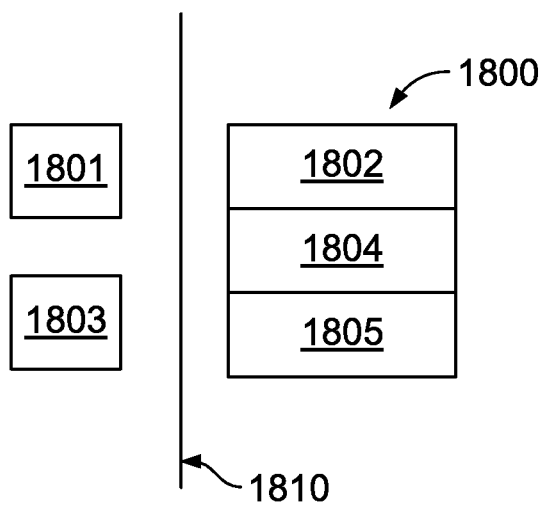
FIG. 18 is a block diagram depicting the modules of another exemplary embodiment of the stimulating device of the present specification.

In another embodiment, referring to FIG. 18, a patient is treated by laparoscopically implanting a plurality of electrodes 1801 (within the anatomical area to be stimulated) in wired communication with a transducer 1803 (comprising an antenna) proximate the skin surface. The transducer 1803 wirelessly communicates with an external energy source 1800 (comprising a controller 1802, waveform generator 1804, and power source 1805, such as a battery) across the surface of the patient's skin 1810. The external energy source 1800 can be applied to the stimulation site by a patient, as described above. With close energy source application, radio frequency, ultrasound, or inductive/magnetic energies can be used.

Referring to FIGS. 16-18 simultaneously, as further discussed below, the stimulation source 1600, 1700, 1800 can initiate or terminate stimulation, when properly placed over the appropriate site, based on any of a plurality of triggers, including manually by a patient, patient activity, or other sensed patient states. The stimulation source 1600, 1700, 1800 can generate a plurality of different pulse widths, amplitudes, frequencies, or combinations thereof, as further described below.

Therapy Two: Controller Timed and Delivered Stimulation

In a second therapy, a patient may not be effectively therapeutically treated with intermittent wireless short bursts of stimulation applied a plurality of times during a day. Rather, a patient requires bursts of stimulation for a period greater than a predefined period of time, or for a frequency of more than a predefined number of times per day. Accordingly, a patient is subjected to stimulation that is initiated, effectuated, or otherwise triggered by a programmed controller. This more frequent, or continuous, stimulation is effective to treat certain symptoms of a patient, including treatment of GERD, or reaching a predetermined LES high pressure zone length, gastric pressure, LES pressure, muscle tension or electrode impedance.

Figure 19:
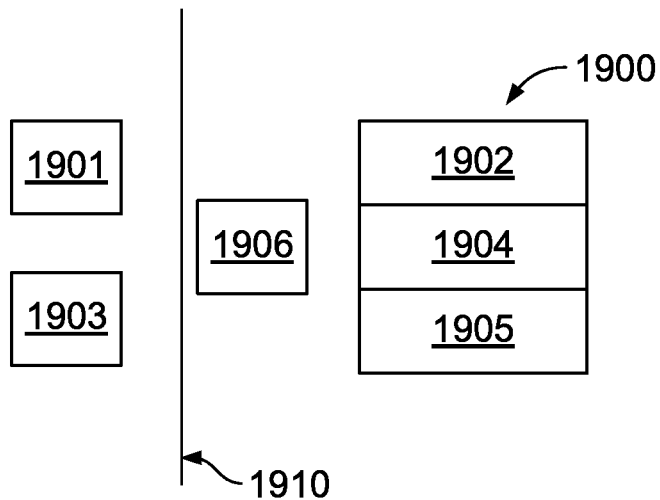
FIG. 19 is a block diagram depicting the modules of another exemplary embodiment of the stimulating device of the present specification.

In this treatment method, a patient can be effectively treated by a plurality of embodiments, including:

1) Referring to FIG. 19, endoscopically implanting a microstimulator 1901 (having a receiver and placed within the anatomical area to be stimulated) in wireless or wired communication with a subcutaneously implanted transducer 1903 that, in turn, wirelessly communicates with a transducer 1906 (comprising at least one antenna and an adhesive surface) applied to the patient's skin surface 1910 which is wired to, and receives signals from, a stimulator source 1900 (comprising a controller 1902, waveform generator 1904, and power source 1905, such as a battery). The controller 1902 can be programmed to initiate or terminate stimulation based on a plurality of patient-specific triggers, such as pH level, LES high pressure zone length, gastric pressure, LES pressure, fasting state, eating state, sleeping state, physical incline, or patient activity state, among other triggers as further described below. The stimulation source 1900 can generate and transmit radio frequency or ultrasound energy and can generate a plurality of different pulse widths, amplitudes, frequencies, or combinations thereof, as further described below. In one embodiment, the radio frequency or ultrasound pulse is designed to operate over a wireless distance of 6 inches or less, through the human body, with a maximum pulse amplitude of 10 mAmp and a maximum pulse width of 10 msec. It should be appreciated that if one parameter is lowered, such as the wireless distance (lowering it to one inch), another parameter can be modified accordingly, such as the amplitude (increasing it to 30 mAmp).

Figure 20:
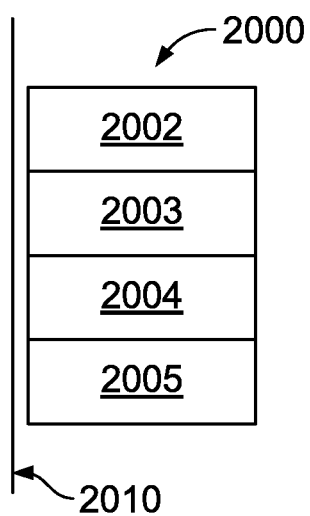
FIG. 20 is a block diagram depicting the modules of another exemplary embodiment of the stimulating device of the present specification.

2) Referring to FIG. 20, endoscopically implanting a microstimulator 2001 (having a receiver and placed within the anatomical area to be stimulated) in wireless communication with a stimulator source 2000 (comprising a controller 2002, transducer 2003, waveform generator 2004, and power source 2005, such as a battery) and which is held against a patient's skin 2010 over the microstimulator site with straps, adhesives, garments, or bindings. The controller 2002 can be programmed to initiate or terminate stimulation based on a plurality of patient-specific triggers, such as pH level, LES pressure, fasting state, eating state, sleeping state, physical incline, or patient activity state, among other triggers as further described below. The stimulation source 2000 can generate and transmit radio frequency or ultrasound energy and can generate a plurality of different pulse widths, amplitudes, frequencies, or combinations thereof, as further described below. In one embodiment, the radio frequency or ultrasound pulse is designed to operate over a wireless distance of 6 inches or less, through the human body, with a maximum pulse amplitude of 10 mAmp and a maximum pulse width of 10 msec. It should be appreciated that if one parameter is lowered, such as the wireless distance (lowering it to one inch), another parameter can be modified accordingly, such as the amplitude (increasing it to 30 mAmp).

Figure 21:
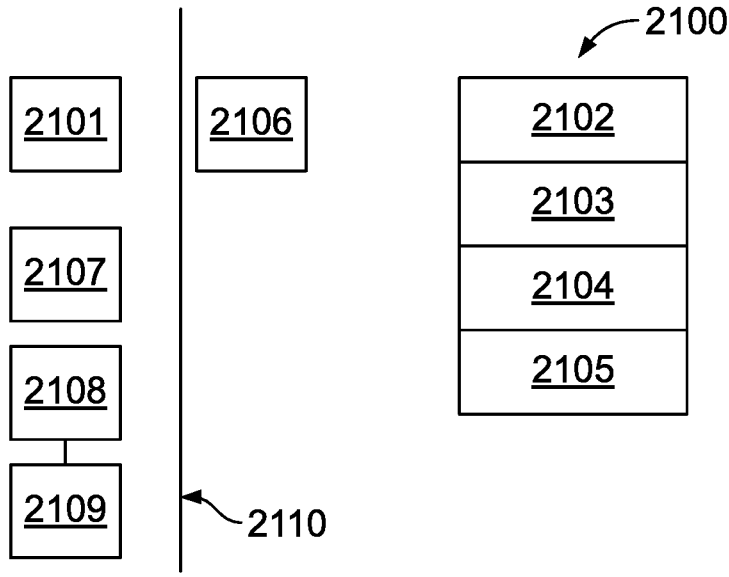
FIG. 21 is a block diagram depicting the modules of another exemplary embodiment of the stimulating device of the present specification.

3) Referring to FIG. 21, endoscopically implanting a microstimulator 2101 (having a receiver and placed within the anatomical area to be stimulated) in wireless communication with a relay device 2106 worn over the stimulation site 2110 that is in wired communication with an external stimulator 2100, The external stimulator 2100 is in wireless communication with an implanted adapter 2107, which is in wireless communication with an external stimulator 2100, or in wireless communication with an implanted transducer 2108 that is in wired communication, via an electrode, to an implanted stimulator 2109. The stimulator 2100 (comprising a controller 2102, transducer 2103, waveform generator 2104, and power source 2105, such as a battery) can be programmed to initiate or terminate stimulation based on a plurality of patient-specific triggers, such as pH level, LES high pressure zone length, gastric pressure, LES pressure, fasting state, eating state, sleeping state, physical incline, or patient activity state, among other triggers as further described below. The stimulation source 2100 can generate and transmit radio frequency or ultrasound energy and can generate a plurality of different pulse widths, amplitudes, frequencies, or combinations thereof, as further described below. In one embodiment, the radio frequency or ultrasound pulse is designed to operate over a wireless distance of 6 inches or less, through the human body, with a maximum pulse amplitude of 10 mAmp and a maximum pulse width of 10 msec. It should be appreciated that if one parameter is lowered, such as the wireless distance (lowering it to one inch), another parameter can be modified accordingly, such as the amplitude (increasing it to 30 mAmp).

Figure 22:
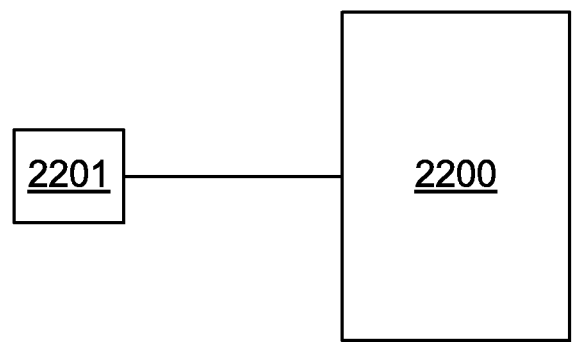
FIG. 22 is a block diagram depicting the modules of another exemplary embodiment of the stimulating device of the present specification.

4) Referring to FIG. 22, laparoscopically implanting a plurality of electrodes 2201 (within the anatomical area to be stimulated) in wired communication with an implanted stimulator 2200 (comprising a primary cell that provides energy and a memory with programmatic instructions for defining appropriate stimulation parameters) which can be programmed to generate stimulation either continuously or periodically based on a predefined program or based on patient-specific triggers, such as pH level, LES high pressure zone length, gastric pressure, LES pressure, LES impedance, fasting state, eating state, sleeping state, physical incline, or patient activity state, among other triggers as further described below. In one embodiment, the stimulator 2200 wirelessly receives control data or information from an external device, which is controlled, at least in part, by a physician or patient. The stimulator 2200 can generate a plurality of different pulse widths, amplitudes, frequencies, or combinations thereof, as described above.

Figure 23:
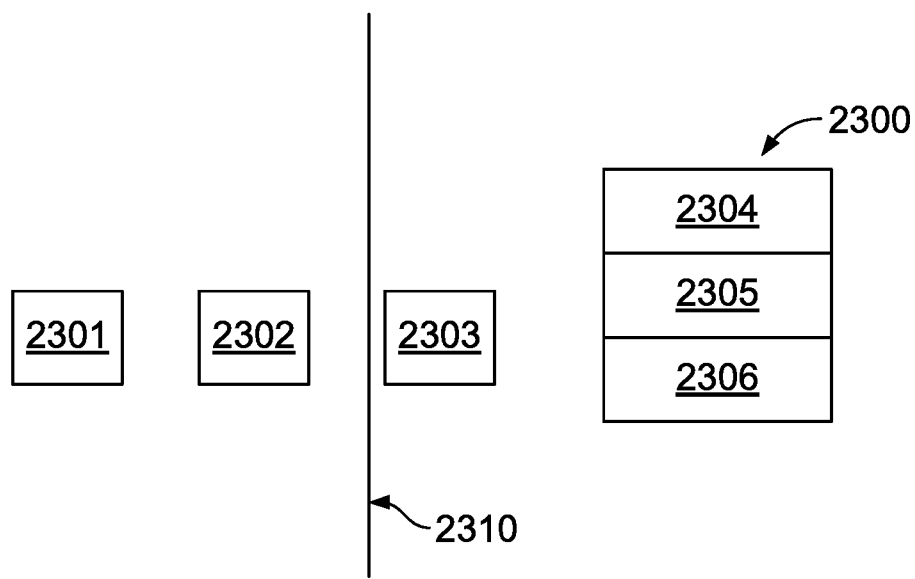
FIG. 23 is a block diagram depicting the modules of yet another exemplary embodiment of the stimulating device of the present specification.

5) Referring to FIG. 23, laparoscopically implanting a plurality of electrodes 2301 (within the anatomical area to be stimulated) in wired communication with a subcutaneously implanted transducer 2302 that, in turn, wirelessly communicates with a stimulator source or a transducer 2303 (comprising at least one antenna and an adhesive surface) applied to the patient's skin surface 2310 which is wired to, and receives signals from, a stimulator source 2300 (comprising a controller 2304, waveform generator 2305, and power source 2306, such as a battery). The controller 2304 can be programmed to initiate or terminate stimulation based on a plurality of patient-specific triggers, such as pH level, LES high pressure zone length, gastric pressure, LES pressure, fasting state, eating state, sleeping state, physical incline, or patient activity state, among other triggers as further described below. The stimulation source 2300 can generate and transmit radio frequency or ultrasound energy and can generate a plurality of different pulse widths, amplitudes, frequencies, or combinations thereof, as further described below.

It should be appreciated that, while the disclosed system can use RF, inductive coupling, magnetic coupling or ultrasound, in one embodiment, the system can combine the use of RF inductive coupling, magnetic coupling, and ultrasound to take best advantage of transmission efficiencies in various media. In one embodiment, the external stimulator source generates RF waveforms, which wirelessly transmit RF energy to an intermediary receiver that can be implanted subcutaneously and that converts the received RF energy into an ultrasound waveform. The intermediary receiver has an RF receiver, an ultrasound waveform generator, and an ultrasound transmitter. In another embodiment, the device comprises a means for storing a charge locally, such as a short-term energy storage component (capacitor), and an associated trigger mechanism, as described above.

It should further be appreciated that the microstimulator (or, where a laparoscopically implanted stimulation electrode and stimulator are used, the stimulator) can locally store energy, be used with RF or US, and rely on an external device for stimulation control and/or energy recharge. Specifically, the microstimulator can comprise a means for storing a charge locally, such as a capacitor. It should further be appreciated that the anatomical region to be stimulated, such as the LES, areas within 2 cm of the LES, the esophagus, or the UES, may be stimulated using a plurality of microstimulators or electrodes, including an array of microstimulators or electrodes affixed to a mesh or other substrate. It should further be appreciated the microstimulator or implanted stimulator can store enough energy to function as a backup, or otherwise fill in gaps in energy transfer from an external source when, for example, wireless transmission coupling is interrupted or inefficient. In another embodiment, the microstimulator or implanted stimulator receives an energy stream from an external stimulator and, in real-time, forms the requisite waveform based on parameters encoded in a wireless control stream or embedded in the energy stream. In another embodiment, the microstimulator or implanted stimulator receives a pre-formed waveform from an external stimulator.

As discussed above, the endoscopic therapeutic treatments are part of the diagnosis process in which a microstimulator is endoscopically implanted and used in combination with an external device for an initial period. Data is gathered regarding frequency of stimulation required, amount of energy required, and other factors. A patient then receives a laparoscopically implanted permanent system operating in accordance with the gathered data.

Exemplary Use No. 1

In one embodiment, patients with diagnosis of GERD responsive to PPI, increase esophageal acid on 24 h pH monitoring off GERD medications, basal LES pressures ≥5 mm Hg, hiatal hernia <2 cm and esophagitis ≤LA Grade B had a stimulator placed endoscopically in the LES by creating a 3 cm submucosal tunnel. The stimulator was secured to the esophagus muscularis or serosa. Electrical stimulation (EST) was delivered 6-12 hours post-implant per following protocols 1) Short-pulse (SP) 200 µsec, 20 Hz, 10 mAmp; if no response in LES pressure increase to 15 mAmp; if increase in LES pressure decrease to 5 mAmp and 2) Intermediate-pulse (IP) 3 msec, 20 Hz, 5 mAmp for 20 minutes; if no response, increase to 10 mAmp. Each session of EST lasted 20 minutes and was followed by a washout period of 20 minutes or time needed for LES pressure to return to baseline, whichever was longer. High-resolution manometry was performed using standard protocol pre-, during and post-stimulation. Symptoms of heartburn, chest pain, abdominal pain and dysphagia pre-, during and post-stimulation were also recorded. Continuous cardiac monitoring was performed during and after the stimulation to look for any adverse cardiac events associated with EST.

Three patients underwent successful stimulator implantation. One patient was stimulated using 200 µsec, 20 Hz, 3 mAmp (SP 3) and had a significant increase in the LES pressure (Baseline=5.7 mm Hg; post-stimulation=42 mm Hg). As shown in FIGS. 24-30, patients had a significant increase in the LES pressure with all sessions of EST (Table 5). There was no effect on swallow induced relaxation and improvement in post-swallowing LES pressure augmentation with EST. There were no adverse EST related symptoms or any cardiac rhythm abnormalities.

TABLE 5

EST Protocol

| | Median LES pressure (mmHg) | | |
|---|---|---|---|
| | Pre-Stimulation | Stimulation | Post-Stimulation |
| SP-10 mAmp | 8.1 | 25.3 | 17.9 |
| SP-5 mAmp | 9.7 | 37.7 | 17.8 |
| IP-5 mAmp | 6.5 | 26.0 | 29.2 |

Accordingly, in patients with GERD, EST results in significant increase in LES pressure without affecting patient swallow function or inducing any adverse symptoms or cardiac rhythm disturbances. EST delivered via a wired or wireless electrical stimulator offers a novel therapy to patients with GERD.

Exemplary Use No. 2

In one embodiment, a patient with diagnosis of GERD has a baseline LES pressure of 4-6 mmHg and impedance was about 320 ohms. A stimulation having a pulse of 200 µs and 5 mAmp was applied. After 15 minutes, a sustained LES tone of 25-35 mmHg was observed, which remained high for over 90 minutes after stopping stimulation. After 3 hours, the LES pressure returned to baseline. This patient was than treated using a patient specific stimulation protocol of 200 µs pulse, 5 mAmp amplitude, 20 Hz frequency, an ON phase of 20 minutes and an OFF phase of 2 hours. His LES was restored to normal function and his GERD was controlled.

Exemplary Use No. 3

In one embodiment, a patient with diagnosis of GERD has a baseline LES pressure of 4-6 mmHg and impedance was about 320 ohms. A stimulation having a pulse of 200 µs and 10 mAmp was applied. After 15 minutes, a sustained LES tone of 25-35 mmHg was observed. The patient was instructed to engage in a wet swallow. The patient engaged in a wet swallow, while stimulation was being applied, without feeling any substantive inhibition of the swallow function. This patient was then treated using a patient specific stimulation protocol of 200 µs pulse, 5 mAmp amplitude, 20 Hz frequency, an ON phase of 20 minutes and an OFF phase of 2 hours. His LES was restored to normal function and his GERD was controlled. Optionally, a pressure sensor was implanted in the LES and used to terminate the ON phase when a sustained LES pressure of greater than 20 mmHg for 5 minutes was achieved and used to terminate the OFF phase when a sustained LES pressure reaching 10 mmHg or the patient's baseline, whichever is higher, was achieved.

Exemplary Use No. 4

In one embodiment, patients are subjected to a series of diagnostic tests to determine a plurality of therapeutic stimulation parameters and to select stimulation parameters with the lowest average charge which is still able to elicit a pressure response in the range of at least 15-20 mmHg sustained for at least 5 minutes as measured in manometry. The diagnostic tests include subjecting patients to a series of stimulation sequences, as provided in the table below:

TABLE 6

Stimulation Sequence Settings

| Sequence # | Electrical Stimulation Type | Pulse Frequency | Pulse Duration | Pulse Amplitude |
|---|---|---|---|---|
| 1 | High-Frequency | 20 Hz | 200 μsec | 5 mAmp |
| 2 (only if #1 does not reach 20 mmHg or invoke a sufficiently positive response) | High-Frequency | 20 Hz | 200 μsec | 10-15 mAmp (preferably 10 mAmp) |
| 3 (only if #2 does not reach 20 mmHg or invoke a sufficiently positive response) | Mid-Frequency | 20 Hz | 3 ms | 5-15 mAmp (preferably 10 mAmp) |
| 4 (only if #3 does not reach 20 mmHg or invoke a sufficiently positive response) | Mid-Frequency | 20 Hz | 3 ms | 5-15 mAmp |
| 5 (only if #4 does not reach 20 mmHg or invoke a sufficiently positive response) | Low-frequency | 6 cycles/min | 375 ms | 5 mAmp |
| 6 (only if #5 does not reach 20 mmHg) | Low-frequency | 6 cycles/min | 375 ms | 5-15 mAmp |

Each selected stimulation parameter is applied for 5 hours during which stimulation is turned on until pressure is greater than or equal to 20 mmHg for at least 5 minutes (or until the time of duration reaches 60 minutes) and then stimulation is turned off until the pressure drops to less than 10 mmHg, or the patient's baseline, whichever is higher. Stimulation is then turned on again until reaching greater than or equal to 20 mmHg again for at least 5 minutes. This on-off process continues while the time duration between each on-off cycle is recorded. If the patient experiences pain or discomfort for any given stimulation sequence, the pulse amplitude is decreased in 1 mAmp increments until stimulation is tolerable. Once the tolerable setting is established, the stimulation period is re-initiated. Optionally, there is a washout period between sequences to remove any residual effect from the application of a prior sequence. That washout period can be equal to one hour or until LES pressure returns to the patient's baseline, whichever is longer. Optionally, continuous manometry is performed during the post-stimulation period to assess any delayed effect from a failed sequence or to measure the duration of effect from a successful sequence.

During the last two hours of the diagnostic session, stimulation is turned "on" and "off" at fixed durations based on the measured values recorded in the first part of the test. Impedance measurements are performed periodically during this phase using an external impedance measurement device or by measuring the resulting voltage waveform from stimulation using a floating oscilloscope.

Optionally, a second dosing evaluation process is performed building on the sequence results as performed above. In one embodiment, a patient's baseline LES pressure is evaluated over a 20 minute period. Simulation is applied for 125% of the on time period, as determined from the first set of sequence measurements. Stimulation is then stopped for 75% of the off time period, as determined from the first set of sequence measurements, or until LES pressure falls below 10 mmHg or baseline, whichever is higher. Restart stimulation for 125% of the on time period and monitor LES pressure. If LES pressure does not reach 20 mmHg, then continue stimulation for up to 150% of the on time period or until pressure reaches 20 mmHg (whichever comes first). Repeat the off time period and continue cycling between the prior on time period and off time period until achieving 6 hours of LES pressure above 10 mmHg. Conduct esophageal manometry with wet swallows post stimulation sequence.

Exemplary Use No. 5

In one embodiment, patients are subjected to a series of diagnostic tests to determine a plurality of therapeutic stimulation parameters and to select stimulation parameters with the lowest average charge which is still able to elicit a pressure response in the range of at least 15-20 mmHg sustained for at least 5 minutes as measured in manometry. The diagnostic tests include subjecting patients to a series of stimulation sequences, as provided in the table below:

TABLE 7

| Sequence # | Electrical Stimulation Type | Pulse Frequency | Pulse Duration | Pulse Amplitude | Stimulation Duration |
|---|---|---|---|---|---|
| 1 | Baseline | 0 Hz | 0 μsec | 0 mAmp | 0 minutes |
| 2 | High-Frequency | 20 Hz | 200 μsec | 5 mAmp | 30 minutes |
| 3 (only if #2 does not reach 20 mmHg or invoke a sufficiently positive response) | High-Frequency | 20 Hz | 200 μsec | 10-15 mAmp (preferably 5 mAmp) | 60 minutes |
| 4 (only if #3 does not reach 20 mmHg or invoke a sufficiently positive response) | High-Frequency | 20 Hz | 200 μsec | 10 mAmp | 30 minutes |
| 5 (only if #4 does not reach 20 mmHg or invoke a sufficiently positive response) | High-Frequency | 20 Hz | 200 μsec | 5-15 mAmp (preferably 10 mAmp) | 60 minutes |
| 6 (only if #5 does not reach 20 mmHg or invoke a sufficiently positive response) | High-Frequency | 20 Hz | 200 μsec | 15 mAmp | 30 minutes |
| 7 (only if #6 does not reach 20 mmHg) | High-Frequency | 20 Hz | 200 μsec | 15 mAmp | 60 minutes |

Stimulation is turned on until pressure is greater than or equal to 20 mmHg for at least 5 minutes (or until the list time duration is reached) and then stimulation is turned off until the pressure drops to less than 10 mmHg, or the patient's baseline, whichever is higher. Stimulation is then turned on again until reaching greater than or equal to 20 mmHg again for at least 5 minutes. This on-off process continues while the time duration between each on-off cycle is recorded. If the patient experiences pain or discomfort for any given stimulation sequence, the pulse amplitude is decreased in 1 mAmp increments until stimulation is tolerable. Once the tolerable setting is established, the stimulation period is re-initiated.

Optionally, there is a washout period between sequences to remove any residual effect from the application of a prior sequence. That washout period can be equal to one hour or until LES pressure returns to the patient's baseline, whichever is longer. Optionally, continuous manometry is performed during the post-stimulation period to assess any delayed effect from a failed sequence or to measure the duration of effect from a successful sequence. Optionally, continuous manometry is performed during the post-stimulation period from the successful sequence to determine the duration of the effect, that is, until the LES pressure is below 10 mm Hg or reaches baseline, whichever is higher.

The stimulation sequences listed above may be repeated, if no success is achieved, except using a 3 msec dose instead of the 200 μsec dose.

Optionally, a second dosing evaluation process is performed building on the sequence results as performed above. In one embodiment, a patient's baseline LES pressure is evaluated over a 20 minute period. Simulation is applied for 125% of the on time period, as determined from the first set of sequence measurements. Stimulation is then stopped for 75% of the off time period, as determined from the first set of sequence measurements, or until LES pressure falls below 10 mmHg or baseline, whichever is higher. Stimulation is restarted for 125% of the on time period and LES pressure is monitored. If LES pressure does not reach 20 mmHg, then continue stimulation for up to 150% of the on time period or until pressure reaches 20 mmHg (whichever comes first). Repeat the off time period and continue cycling between the prior on time period and off time period until achieving 6 hours of LES pressure above 10 mmHg. Conduct esophageal manometry with wet swallows post stimulation sequence. Additional stimulation measurements can be made, including baseline manometry with wet swallows, repeating successful sequences for an extended period, such as 12 hours, or manometry measurements with wet swallows after conducting a successful stimulation sequence.

Exemplary Use No. 6

In one embodiment, 10 patients (9 females, 1 male mean age 52.6 years, range-40-60 years) with symptoms of GERD responsive to PPI's, low resting LES pressure and abnormal 24-hr intraesophageal pH test were enrolled. All had symptoms of heartburn and/or regurgitation for at least 3 months, which was responsive to therapy with proton pump inhibitors (PPI's). Preoperative evaluation included an upper GI endoscopy, esophageal manometry and ambulatory 24-hr esophageal pH recording. To be included, the patient's resting LESP had to be 5-15 mmHg, and the intraesophageal pH had to be less than four more than 5% of the time. Patients with hiatal hernia >3 cm, erosive esophagitis more severe than Los Angeles grade C, Barrett's esophagus or non-GERD related esophageal disease were excluded.

Bipolar stitch electrodes were placed longitudinally in the LES during an elective laparoscopic surgery, secured by a clip and exteriorized through the abdominal wall. It consisted of two platinum-iridium electrodes with an exposed length of 10 mm. They were implanted longitudinally in the right and left lateral aspects the LES and secured by a clip. The electrode was then exteriorized through the laparoscopic port in the abdominal wall in the left upper quadrant and connected to a macro stimulator.

Following recovery, an external pulse generator delivered 2 types of stimulation for periods of 30 minutes: 1) low energy stimulation; pulse width of 200 μsec, frequency of 20 Hz amplitude and current of 5 to 15 mA (current was increased up to 15 mA if LESP was less than 15 mmHg), and 2) high energy stimulation; pulse width of 375 msec, frequency of 6 cpm and amplitude 5 mA. Resting LESP, amplitude of esophageal contractions and residual LESP in response to swallows were assessed before and after stimulation. Symptoms of chest pain, abdominal pain and dysphagia were recorded before, during and after stimulation and 7-days after stimulation. Continuous cardiac monitoring was performed during and after stimulation.

The high frequency, low energy stimulation was delivered as square-wave pulses with a width of 200 microseconds at a frequency of 20 Hz and a current of 5-15 mA. If LESP did not increase to over 15 mmHg using the 5 mA stimulus, the current was gradually increased up to 15 mA. The low frequency, high energy stimulation was delivered as square-wave pulse with a width of 375 milliseconds at a frequency of 6 CPM and current of 5 mA. The current was not varied during low frequency stimulation.

If resting LESP rose above 15 mmHg during ES, the stimulus was terminated and LESP was allowed to return to its pre-stimulation baseline. A different stimulation was given when LESP returned to baseline. Stimulations were given in random order, with patients unaware of the type or timing of its delivery (frequent checks of impedance were mixed with stimulation). Five water swallows were given before and after termination of each session of ES. All studies were done under continuous cardiac monitoring, and patients were supervised closely. Patients were instructed to report any unusual symptom, and in particular dysphagia, palpitations, and chest/abdominal pain.

Nine subjects received high frequency, low energy and four subjects received low frequency, high energy stimulation. Both types of stimulation significantly increased resting LESP: from 8.6 mmHg 95%, CI 4.1-13.1 to 16.6 mmHg, 95% CI 10.8-19.2, p<0.001 with low energy stimulation and from 9.2 mmHg 95% CI 2.0-16.3 to 16.5 mmHg, 95% CI 2.7-30.1, p=0.03 with high energy stimulation. Neither type of stimulation affected the amplitude of esophageal peristalsis or residual LESP. No subject complained of dysphagia. One subject had retrosternal discomfort with stimulation at 15 mA that was not experienced with stimulation at 13 mA. There were no adverse events or any cardiac rhythm abnormalities with either type of stimulation.

With respect to high frequency, low energy stimulation, there was a consistent increase in resting LESP in all subjects, observed within 15 minutes of initiating ES, and increased further before the end of stimulation. High frequency, low energy stimulation had no effect on the amplitudes of esophageal contractions or residual LESP in response to 5 cc water swallows. One subject had chest discomfort when the stimulation current was increased to 15 mA, but resolved when the current was decreases to 13 mA.

With respect to low frequency, high energy stimulation, resting LESP consistently increased during stimulation. It had no effect on the amplitudes of peristaltic pressure waves in the smooth muscle esophagus or residual LESP produced by 5 cc water swallows. No abnormalities of cardiac or esophageal function were seen, and no adverse events occurred with either type of stimulation.

Both types of stimulation, high and low energy stimulation, caused a consistent and significant increase in LES pressure. Importantly, both LES relaxation and esophageal contractile activity in response to wet swallows were not affected, indicating that the integrity of the neuromuscular reflex pathways activated by swallows is maintained during stimulation. Stimulation was well tolerated. No patient reported dysphagia. Only one patient reported chest discomfort, with amplitude of 15 mA, that was not experienced when current was reduced to 13 mA. There was no evidence of cardiac adverse effects in any of the patients. Accordingly, short-term stimulation of the LES in patients with GERD significantly increases resting LESP without affecting esophageal peristalsis or LES relaxation.

Exemplary Use No. 7

Six patients with GERD resistant to medical therapy and documented by pH testing underwent electrode implantation in the LES using laparoscopy. All patients had LES pressures in the range of 5-15 mm Hg. A macrostimulator was placed in the subcutaneous pocket using sterile techniques. Within 24 hours after the implant, LES electrical stimulation therapy was started using 215 μsec pulse at 3 mAmp and 20 Hz. For certain patients, the macrostimulator comprised an accelerometer/inclinometer which was used to program the delivery of stimulation twice daily, once every 12 hours, and then increased to 3 times daily, once every 8 hours.

The LES electrical stimulation therapy resulted in significant improvement and normalization of LES pressure as measured by high-resolution manometry and clinically significant decreases in esophageal acid as measured by 24 hour pH testing. All patients had decreases in symptoms measured by patient symptom diaries and improvements in health related quality of life measured by a Health Related Quality of Life survey, short form 12 (GERD HRQL). All patients were successfully taken off proton pump inhibitors medications, nor did the patients use the PPIs on an as-needed basis. None of the patients had treatment related symptoms or adverse events. All patients maintained a normal swallow function.

Figure 24:
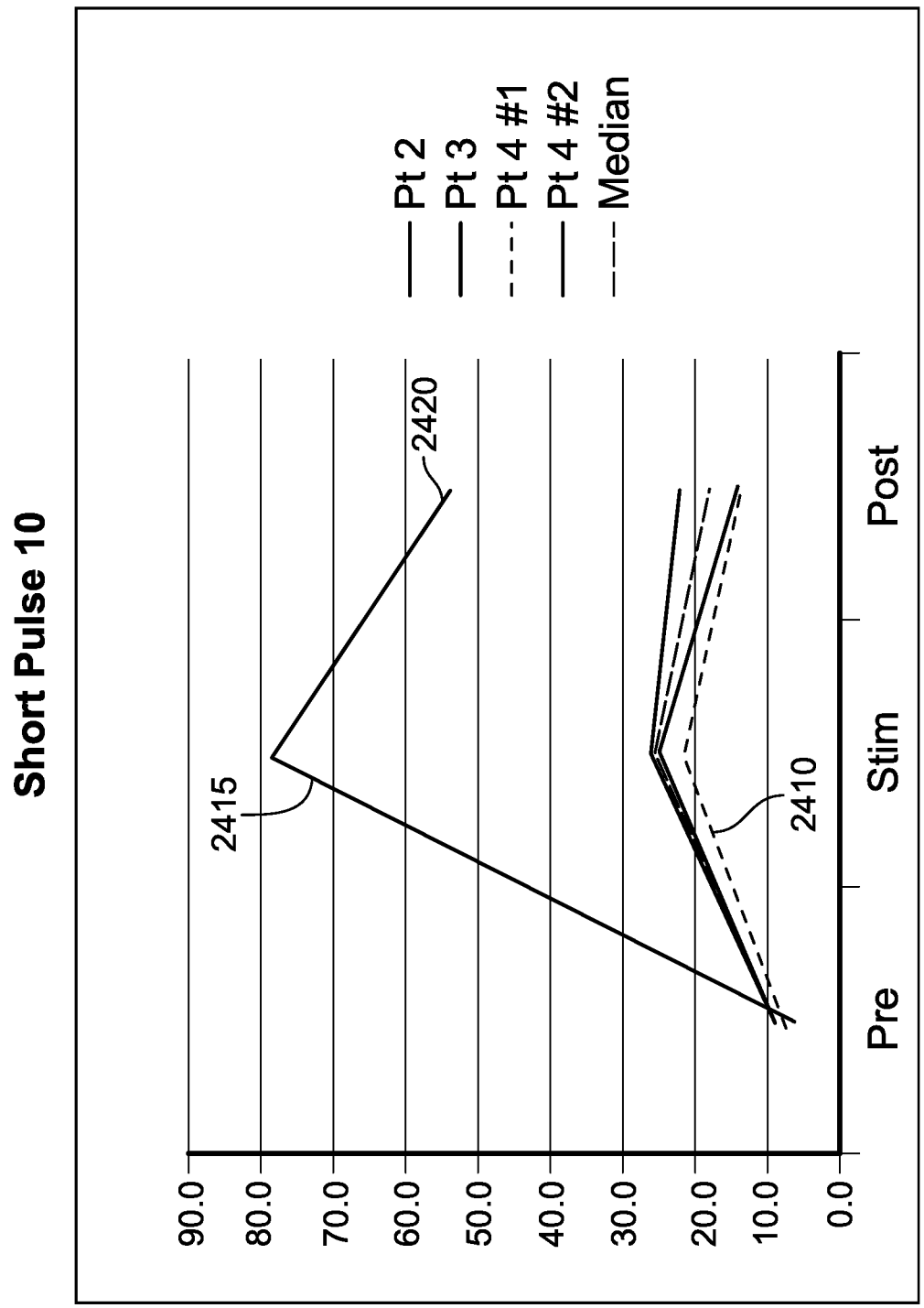
FIG. 24 is a graph relating pressure increases to baseline, stimulation, and post-stimulation periods, in accordance with one embodiment of the present specification.

Referring to FIGS. 24 to 30, the treatment methodologies disclosed herein provide for a sustained improvement in patient LES pressure, a decrease in esophageal acid exposure, and decrease in reported symptoms. Referring to FIG. 24, using a short pulse, relative to a baseline pressure 2410, patient LES pressure can achieve a greater than 2 times increase during stimulation 2415 relative to baseline 2410 and can still retain an elevated pressure, relative to baseline 2410, after stimulation is terminated 2420.

Figure 25:
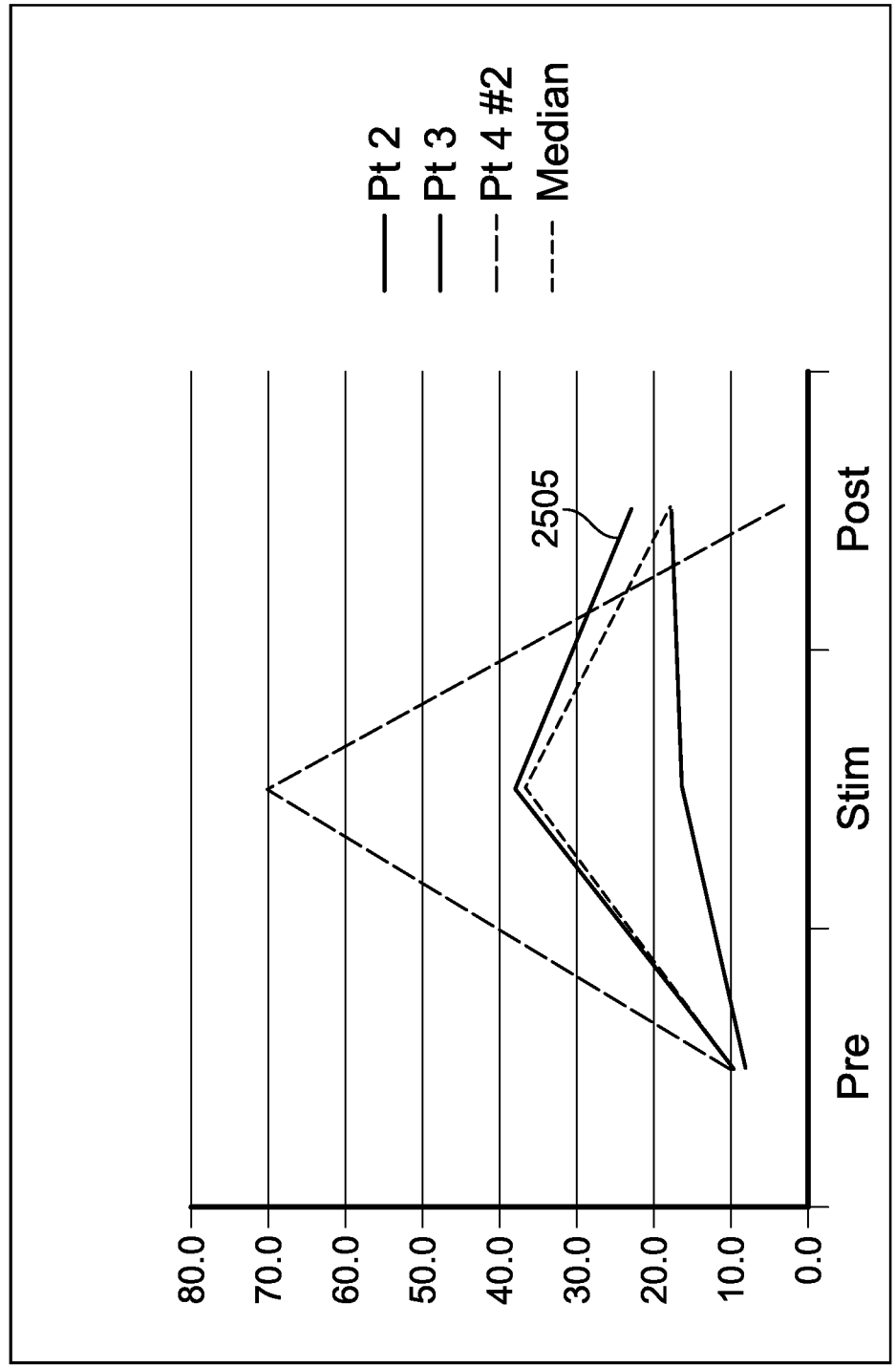
FIG. 25 is a graph showing an improved LES pressure profile over time, in accordance with one embodiment of the present specification.
Figure 26:
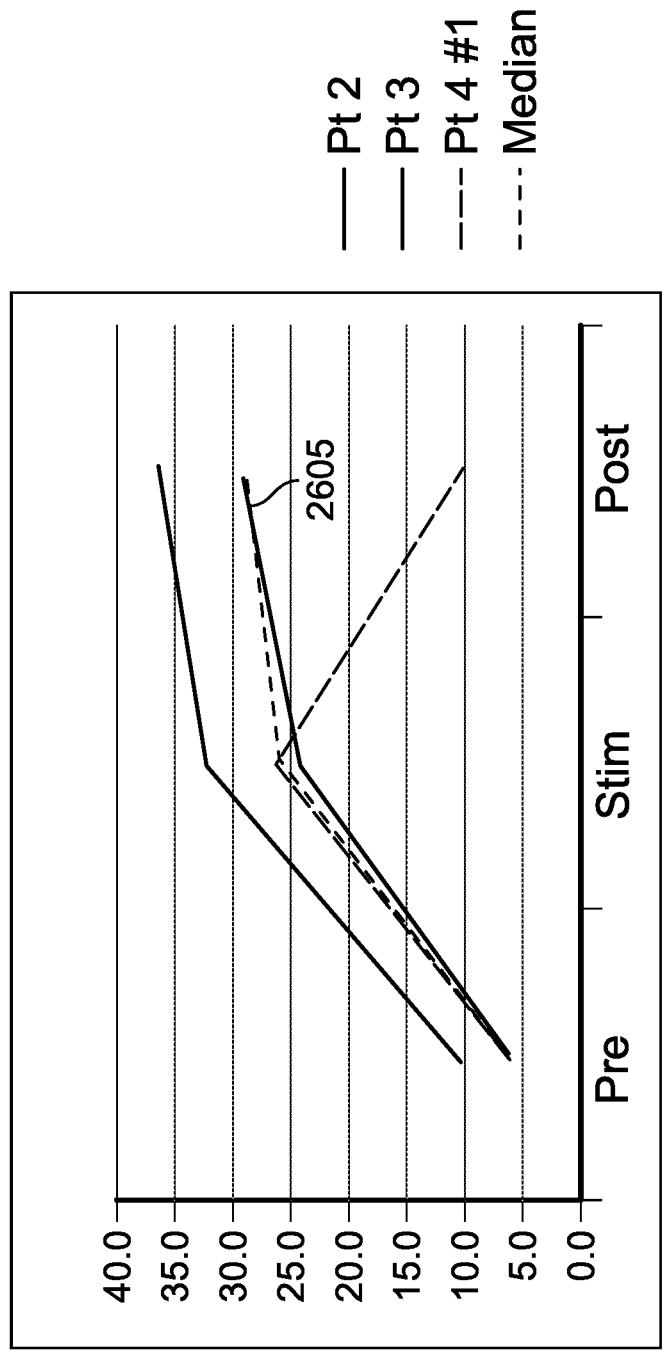
FIG. 26 is another graph showing an improved LES pressure profile over time, in accordance with one embodiment of the present specification.
Figure 27:
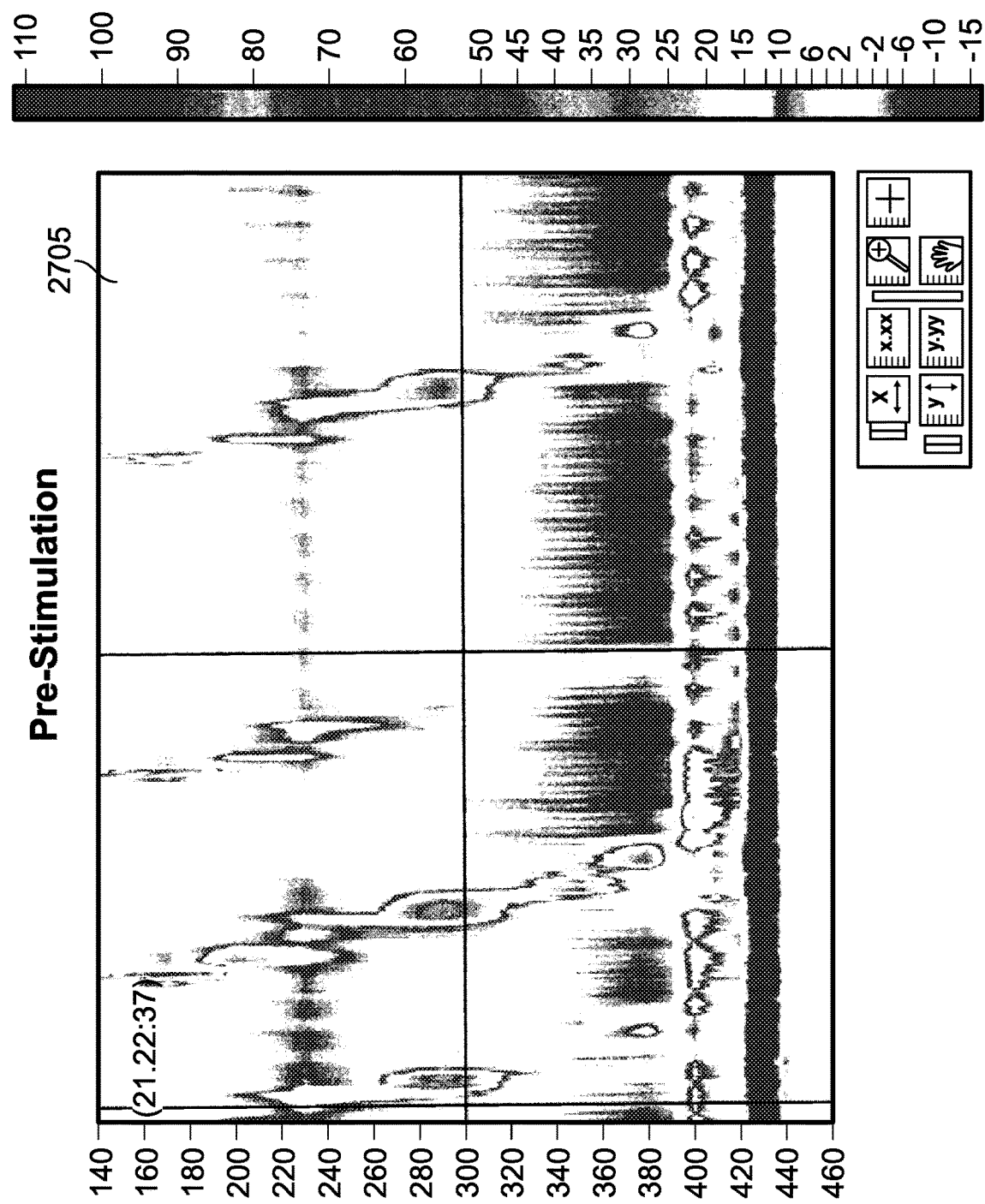
FIG. 27 is a graph showing LES pressures pre-stimulation, in accordance with one embodiment of the present specification.
Figure 28:
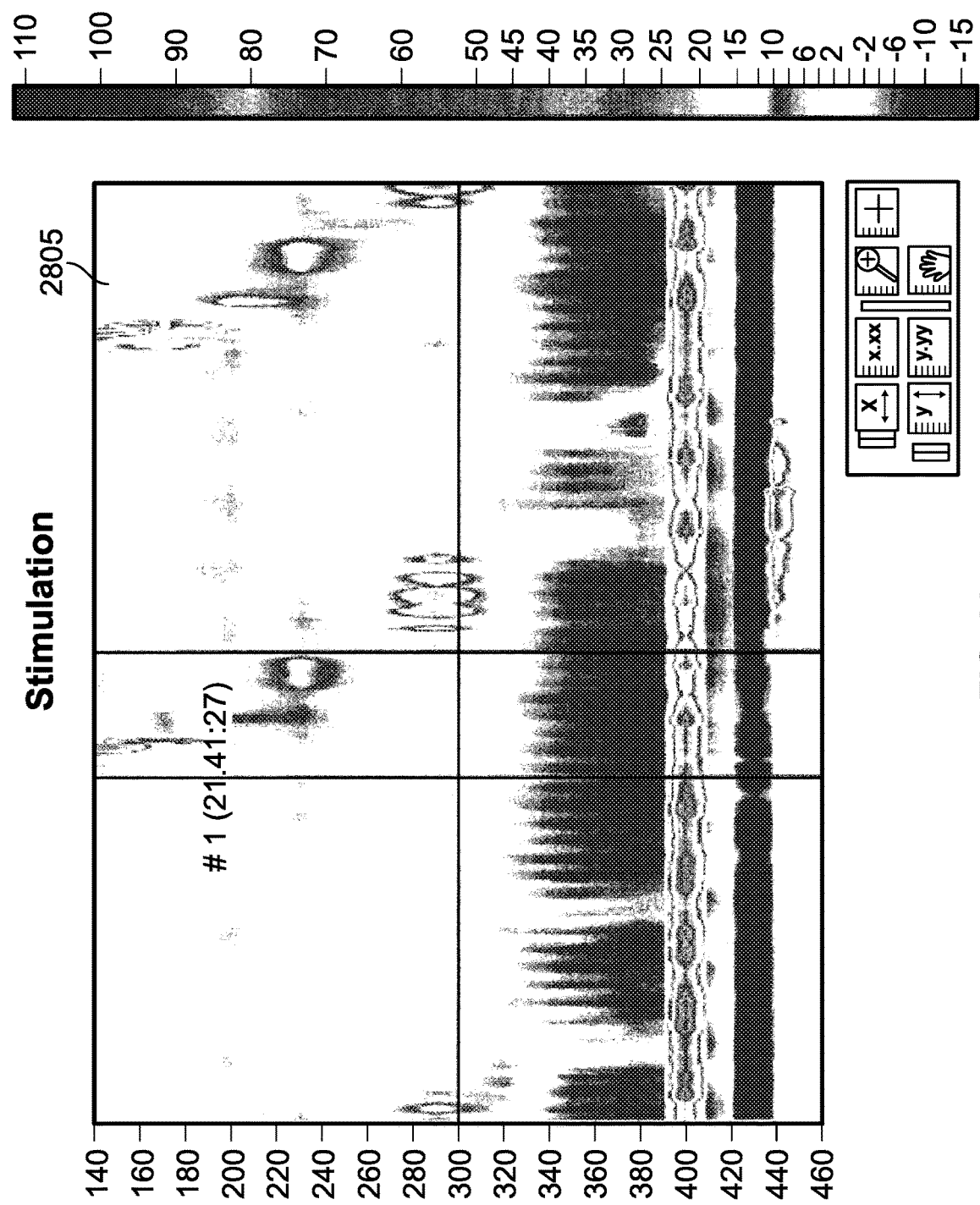
FIG. 28 is a graph showing LES pressures during stimulation, in accordance with one embodiment of the present specification.
Figure 29:
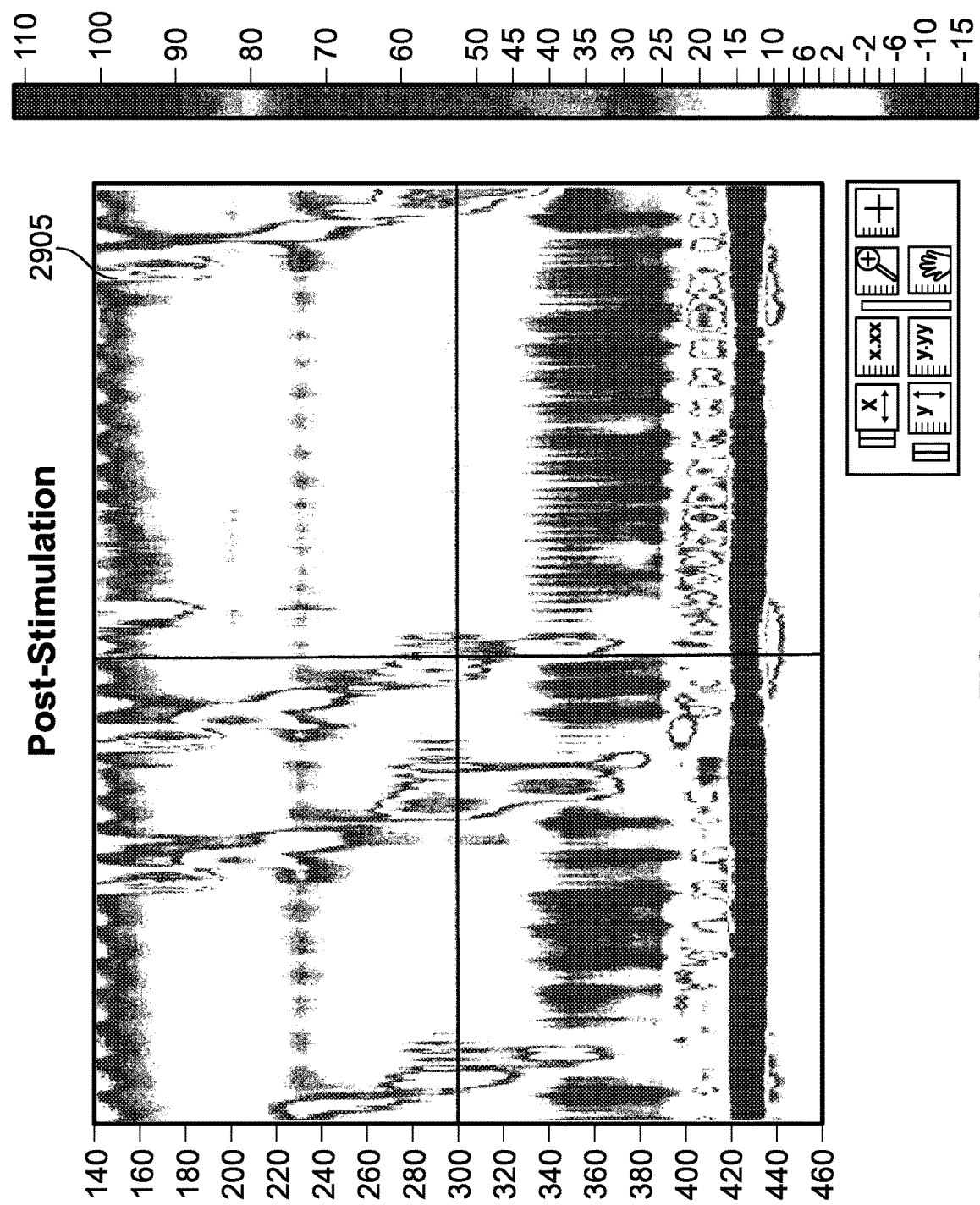
FIG. 29 is a graph showing LES pressures post-stimulation, in accordance with one embodiment of the present specification.
Figure 30:
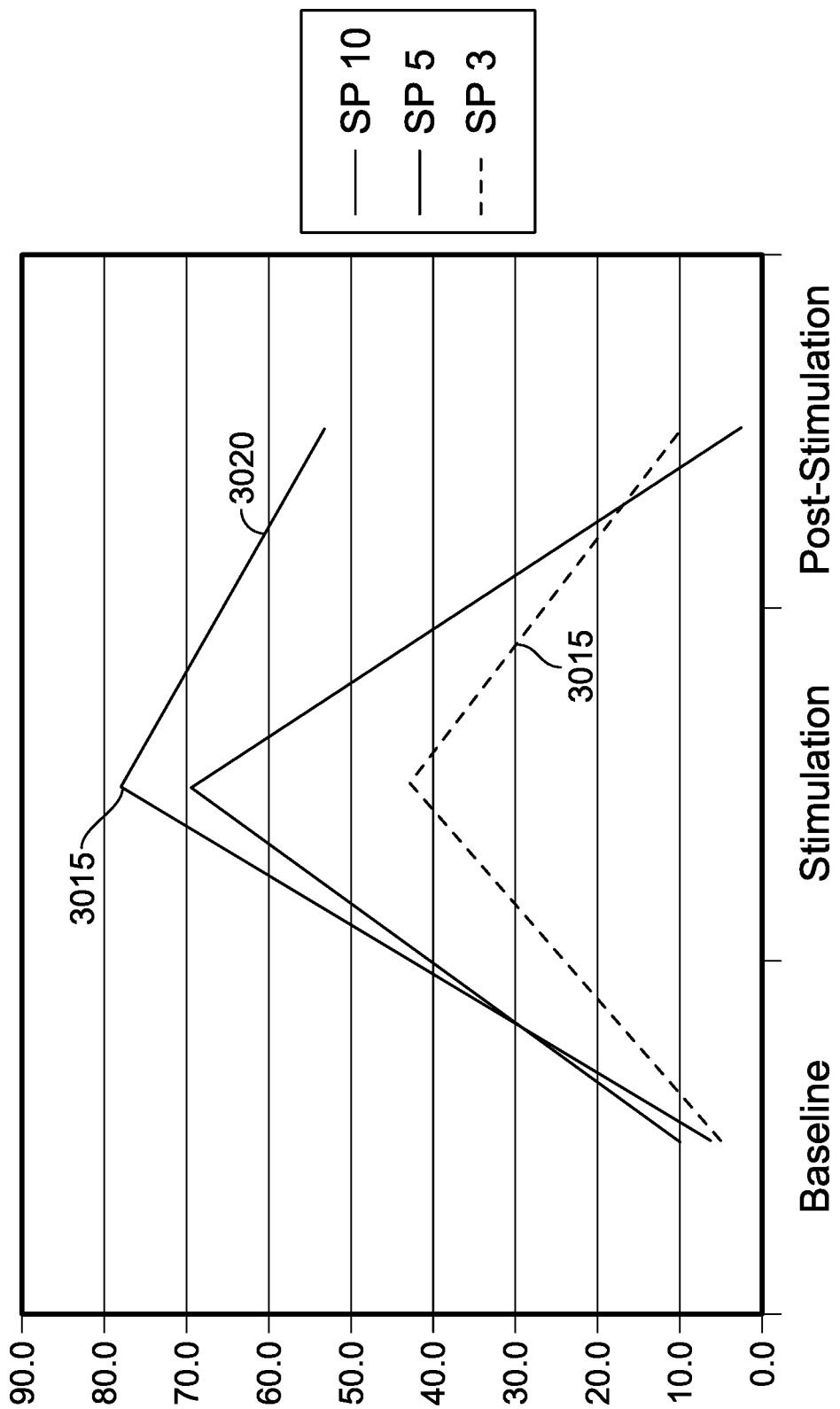
FIG. 30 is another graph showing an improved LES pressure profile over time.

Additionally, as shown in FIGS. 25 and 26, using a short or intermediate pulse, a patient's LES pressure can be reliably maintained within or above a normal pressure range, 15-25 mmHg 2505, 2605, for weeks after LES stimulation is initiated. As a result, a patient's esophageal acid exposure can be brought within a normal pH range within one week after initiating treatment and maintained for several weeks thereafter. Similarly, a patient's adverse symptoms, associated with GERD, can be brought within a normal range, as measured by GERD HRQL evaluations, within one week after initiating treatment and maintained for several weeks thereafter. The benefits of the present therapy can also be obtained within hours after initiating and terminating stimulation. As shown in FIGS. 27, 28, and 29, relative to a pre-stimulation LES pressure profile 2705, a greater LES pressure profile 2805 can be attained during stimulation and an improved LES pressure profile 2905 can be reliably maintained for hours after LES stimulation is terminated. FIG. 30 is another graph showing an improved LES pressure profile over time. LES pressure increases 3010 over a baseline pressure 3015 and remains elevated 3520 after stimulation is terminated.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A system for modifying a characteristic of a high pressure zone of a lower esophageal sphincter (LES) of a patient, said system comprising:
at least one electrically stimulating electrode in electrical communication with the LES and adapted to be located in at least one of the LES, a gastric cardia of the patient, within 3 cm of the LES, or a stomach of the patient;
a waveform generator coupled to said at least one electrode; and,
a controller configured to control the waveform generator to repeatedly generate and apply an electrical pulse train through the at least one electrically stimulating electrode, wherein said electrical pulse train comprises a pulse width having a range of 30 µsec to 5 msec and a pulse amplitude and wherein values for each of said pulse width and pulse amplitude are selected such that the characteristic of said high pressure zone is modified thereby reducing at least one of a frequency of occurrence or an intensity of gastroesophageal reflux symptoms in said patient while a maximum pressure of the LES is not increased.

2. The system of claim 1, wherein said characteristic is a length of the high pressure zone.

3. The system of claim 2, wherein said modification is increasing the length of the high pressure zone above the threshold level.

4. The system of claim 1, comprising at least two electrodes wherein at least one first electrode is positioned within said LES and at least one second electrode is positioned within a gastric cardia of said patient.

5. The system of claim 1, comprising at least two electrodes wherein at least one first electrode is positioned within said LES and at least one second electrode is positioned in an area within 3 cm of said LES.

6. The system of claim 1, comprising at least two electrodes wherein at least one first electrode is positioned within a gastric cardia of said patient and at least one second electrode is positioned in an area within 3 cm of said LES.

7. The system of claim 1, comprising at least three electrodes wherein at least one first electrode is positioned within said LES, at least one second electrode is positioned within a gastric cardia of said patient, and at least one third electrode is positioned in an area within 3 cm of said LES.

8. The system of claim 1, wherein said high pressure zone has a baseline length prior to stimulation and said threshold level defines a length of said high pressure zone which is at least 10% greater than said baseline length.

9. The system of claim 1 wherein the pulse amplitude is in a range of 1 mA to 15 mA.

10. A system for increasing a length of a high pressure zone of a lower esophageal sphincter (LES) of a patient, said system comprising:
at least one electrically stimulating electrode in electrical communication with the LES and adapted to be located in at least one of the LES, a gastric cardia of the patient, within 3 cm of the LES, or a stomach of the patient;
a waveform generator coupled to said at least one electrode;
a controller configured to control the waveform generator to repeatedly generate and apply an electrical pulse train through the at least one electrically stimulating electrode, wherein said electrical pulse train comprises a pulse width having a range of 30 µsec to 5 msec and a pulse amplitude and wherein values for each of said pulse width and pulse amplitude are selected to increase the length of said high pressure zone above a threshold level which reduces at least one of a frequency of occurrence or an intensity of gastroesophageal reflux symptoms in said patient; wherein an average pressure within said high pressure zone is greater than 5 mm Hg and wherein said high pressure zone has a baseline length prior to stimulation and said threshold level defines a length of said high pressure zone which is at least 10% greater than said baseline length.

11. The system of claim 10, further comprising at least one sensor for sensing at least one physiological parameter of said patient.

12. The system of claim 11, wherein said at least one sensor is configured to measure any one or combination of LES high pressure zone length, LES pressure, esophageal pH, inclinometer data, temperature, or accelerometer data.

13. The system of claim 12, wherein said controller is configured to electrically stimulate said area proximate said LES based on data sensed by said at least one sensor.

14. The system of claim 10 wherein the pulse amplitude is in a range of 1 mA to 15 mA.

* * * * *